US007700090B2

(12) United States Patent
Heidaran et al.

(10) Patent No.: US 7,700,090 B2
(45) Date of Patent: Apr. 20, 2010

(54) CO-CULTURE OF PLACENTAL STEM CELLS AND STEM CELLS FROM A SECOND SOURCE

(75) Inventors: Mohammad Heidaran, Chatham, NJ (US); Jia-Lun Wang, Cherry Hill, NJ (US); Qian Ye, Livingston, NJ (US); Andrew Zeitlin, Basking Ridge, NJ (US); Colleen Suzanne Dulaney, Seattle, WA (US)

(73) Assignee: Anthrogenesis Corporation, Warren, NJ (US)

( * ) Notice: Subject to any disclaimer, the term of this patent is extended or adjusted under 35 U.S.C. 154(b) by 178 days.

(21) Appl. No.: 11/648,802

(22) Filed: Dec. 28, 2006

(65) Prior Publication Data
US 2007/0292399 A1 Dec. 20, 2007

Related U.S. Application Data

(63) Continuation-in-part of application No. 10/366,671, filed on Feb. 13, 2003, now Pat. No. 7,311,905, which is a continuation-in-part of application No. 10/076, 180, filed on Feb. 13, 2002, now abandoned.

(60) Provisional application No. 60/437,292, filed on Dec. 13, 2002, provisional application No. 60/754,692, filed on Dec. 29, 2005.

(51) Int. Cl.
*A01N 63/00* (2006.01)
*A61K 35/50* (2006.01)

(52) U.S. Cl. .................... 424/93.1; 424/93.2; 424/582; 424/583; 435/325; 435/366

(58) Field of Classification Search .................... None
See application file for complete search history.

(56) References Cited

U.S. PATENT DOCUMENTS

| 3,862,002 | A | 1/1975 | Sanders |
| 4,829,000 | A | 5/1989 | Kleinman et al. |
| 5,004,681 | A | 4/1991 | Boyse et al. |
| 5,192,553 | A | 3/1993 | Boyse et al. |
| 5,197,985 | A | 3/1993 | Caplan et al. |
| 5,226,914 | A | 7/1993 | Caplan et al. |
| 5,372,581 | A | 12/1994 | Anderson |
| 5,415,665 | A | 5/1995 | Hessel et al. |
| 5,437,994 | A | 8/1995 | Emerson et al. |
| 5,460,964 | A | 10/1995 | McGlave et al. |
| 5,464,764 | A | 11/1995 | Capecchi et al. |
| 5,486,359 | A | 1/1996 | Caplan et al. |
| 5,487,992 | A | 1/1996 | Capecchi et al. |
| 5,516,532 | A | 5/1996 | Atala et al. |
| 5,591,625 | A | 1/1997 | Gerson et al. |
| 5,605,822 | A | 2/1997 | Emerson et al. |
| 5,627,059 | A | 5/1997 | Capecchi et al. |
| 5,635,386 | A | 6/1997 | Palsson et al. |
| 5,635,387 | A | 6/1997 | Fei et al. |
| 5,643,741 | A | 7/1997 | Tsukamoto et al. |
| 5,646,043 | A | 7/1997 | Emerson et al. |
| 5,654,186 | A | 8/1997 | Cerami et al. |
| 5,654,381 | A | 8/1997 | Hrkach et al. |
| 5,665,557 | A | 9/1997 | Murray et al. |
| 5,668,104 | A | 9/1997 | Nakahata et al. |
| 5,670,147 | A | 9/1997 | Emerson et al. |
| 5,670,351 | A | 9/1997 | Emerson et al. |
| 5,672,346 | A | 9/1997 | Srour et al. |
| 5,673,346 | A | 9/1997 | Iwano et al. |
| 5,709,854 | A | 1/1998 | Griffith-Cima et al. |
| 5,716,616 | A | 2/1998 | Prockop et al. |
| 5,716,794 | A | 2/1998 | Tjota et al. |
| 5,716,827 | A | 2/1998 | Tsukamoto |
| 5,733,541 | A | 3/1998 | Taichman et al. |
| 5,733,542 | A | 3/1998 | Haynesworth et al. |
| 5,736,396 | A | 4/1998 | Bruder et al. |
| 5,744,361 | A | 4/1998 | Hoffman et al. |
| 5,750,397 | A | 5/1998 | Tsukamoto et al. |
| 5,763,197 | A | 6/1998 | Tsukamoto et al. |
| 5,763,266 | A | 6/1998 | Palsson et al. |

(Continued)

FOREIGN PATENT DOCUMENTS

CN        1548529        5/2003

(Continued)

OTHER PUBLICATIONS

Kadereit et al. Stem Cell 2002;20:573-82.*

(Continued)

*Primary Examiner*—Q. Janice Li
(74) *Attorney, Agent, or Firm*—Jones Day

(57) ABSTRACT

The present invention relates to a combination of placental stem cells and stem or progenitor cells derived from a second source, wherein the combination shows improved engraftment as compared to placental stem cells or stem cells from a second source, alone. The combination is referred to as a combined stem cell population. The invention also provides in vitro and in vivo methods for identifying and producing combined stem cell populations, and models of engraftment. In accordance with the present invention, the placental stem cells may be combined with, e.g., umbilical cord blood-derived stem or progenitor cells, fetal or neonatal stem cells or progenitor cells, adult stem cells or progenitor cells, hematopoietic stem cells or progenitor cells, stem or progenitor cells derived from bone marrow, etc.

49 Claims, 2 Drawing Sheets

U.S. PATENT DOCUMENTS

Figures 1A, 1B, 1C, 1D:
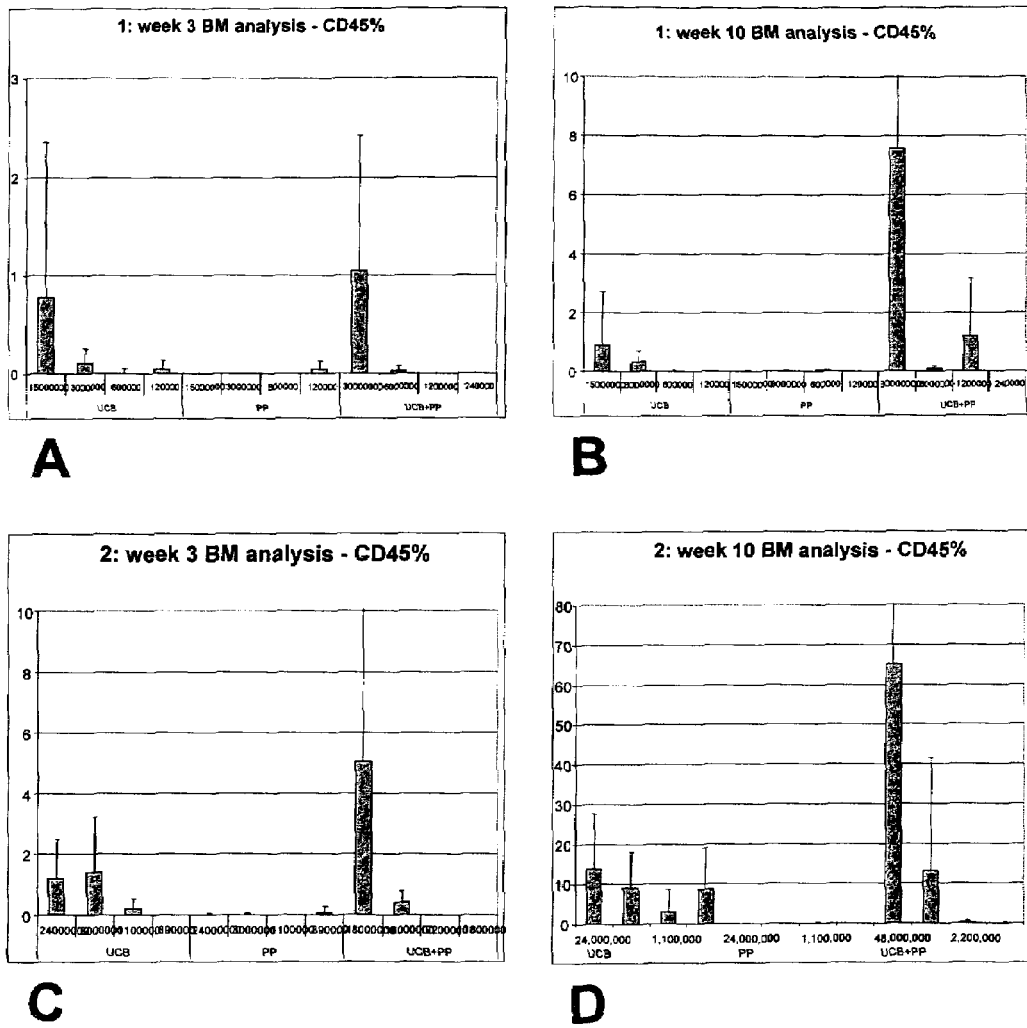

| Patent | | Date | Inventor |
|---|---|---|---|
| 5,806,529 | A | 9/1998 | Reisner et al. |
| 5,807,686 | A | 9/1998 | Wagner et al. |
| 5,811,094 | A | 9/1998 | Caplan et al. |
| 5,827,735 | A | 10/1998 | Young et al. |
| 5,827,740 | A | 10/1998 | Pittenger |
| 5,827,742 | A | 10/1998 | Scadden |
| 5,837,539 | A | 11/1998 | Caplan et al. |
| 5,849,553 | A | 12/1998 | Anderson et al. |
| 5,851,984 | A | 12/1998 | Matthews et al. |
| 5,855,619 | A | 1/1999 | Caplan et al. |
| 5,858,782 | A | 1/1999 | Long et al. |
| 5,861,315 | A | 1/1999 | Nakahata |
| 5,866,414 | A | 2/1999 | Badylak et al. |
| 5,874,301 | A | 2/1999 | Keller et al. |
| 5,877,299 | A | 3/1999 | Thomas et al. |
| 5,879,318 | A | 3/1999 | Van Der Heiden et al. |
| 5,879,940 | A | 3/1999 | Torok-Storb et al. |
| 5,905,041 | A | 5/1999 | Beug et al. |
| 5,906,934 | A | 5/1999 | Grande et al. |
| 5,908,782 | A | 6/1999 | Marshak et al. |
| 5,908,784 | A | 6/1999 | Johnstone et al. |
| 5,914,108 | A | 6/1999 | Tsukamoto et al. |
| 5,914,268 | A | 6/1999 | Keller et al. |
| 5,916,202 | A | 6/1999 | Haswell |
| 5,919,176 | A | 7/1999 | Kuypers et al. |
| 5,919,702 | A | 7/1999 | Purchio et al. |
| 5,922,597 | A | 7/1999 | Verfaille et al. |
| 5,925,567 | A | 7/1999 | Kraus et al. |
| 5,928,214 | A | 7/1999 | Rubinstein et al. |
| 5,928,947 | A | 7/1999 | Anderson et al. |
| 5,942,225 | A | 8/1999 | Bruder et al. |
| 5,942,496 | A | 8/1999 | Bonadio et al. |
| 5,958,767 | A | 9/1999 | Snyder et al. |
| 5,962,325 | A | 10/1999 | Naughton et al. |
| 5,968,829 | A | 10/1999 | Carpenter |
| 5,969,105 | A | 10/1999 | Feng et al. |
| 5,993,429 | A | 11/1999 | Kuypers et al. |
| 5,997,860 | A | 12/1999 | Brauer et al. |
| 6,001,654 | A | 12/1999 | Anderson et al. |
| 6,010,696 | A | 1/2000 | Caplan et al. |
| 6,011,000 | A | 1/2000 | Perrine et al. |
| 6,020,469 | A | 2/2000 | Hershenson |
| 6,022,540 | A | 2/2000 | Bruder et al. |
| 6,022,743 | A | 2/2000 | Naughton et al. |
| 6,022,848 | A | 2/2000 | Kozlov et al. |
| 6,030,836 | A | 2/2000 | Thiede et al. |
| 6,057,123 | A | 5/2000 | Craig et al. |
| 6,059,968 | A | 5/2000 | Wolf, Jr. |
| 6,077,708 | A | 6/2000 | Collins et al. |
| 6,087,113 | A | 7/2000 | Caplan et al. |
| 6,093,531 | A | 7/2000 | Bjornson et al. |
| 6,102,871 | A | 8/2000 | Coe |
| 6,110,739 | A | 8/2000 | Keller et al. |
| 6,127,135 | A | 10/2000 | Hill et al. |
| 6,146,888 | A | 11/2000 | Smith et al. |
| 6,174,333 | B1 | 1/2001 | Kadiyala et al. |
| 6,179,819 | B1 | 1/2001 | Haswell |
| 6,184,035 | B1 | 2/2001 | Csete et al. |
| 6,190,368 | B1 | 2/2001 | Kuypers et al. |
| 6,214,369 | B1 | 4/2001 | Grander et al. |
| 6,224,860 | B1 | 5/2001 | Brown |
| 6,225,119 | B1 | 5/2001 | Qasba et al. |
| 6,227,202 | B1 | 5/2001 | Mataparkar |
| 6,231,880 | B1 | 5/2001 | Perrine |
| 6,239,157 | B1 | 5/2001 | Mbalaviele et al. |
| 6,248,587 | B1 | 6/2001 | Rodgers et al. |
| 6,251,383 | B1 | 6/2001 | Upadhyay et al. |
| 6,255,112 | B1 | 7/2001 | Thiede et al. |
| 6,261,549 | B1 | 7/2001 | Fernandez et al. |
| 6,280,718 | B1 | 8/2001 | Kaufman et al. |
| 6,281,012 | B1 | 8/2001 | McIntosh et al. |
| 6,300,314 | B1 | 10/2001 | Wallner et al. |
| 6,306,575 | B1 | 10/2001 | Thomas et al. |
| 6,312,950 | B1 | 11/2001 | Ohmura et al. |
| 6,322,784 | B1 | 11/2001 | Pittenger et al. |
| 6,326,019 | B1 | 12/2001 | Tseng |
| 6,326,198 | B1 | 12/2001 | Emerson et al. |
| 6,328,765 | B1 | 12/2001 | Hardwick et al. |
| 6,328,960 | B1 | 12/2001 | McIntosh et al. |
| 6,335,195 | B1 | 1/2002 | Rodgers et al. |
| 6,337,387 | B1 | 1/2002 | Sakano et al. |
| 6,338,942 | B2 | 1/2002 | Kraus et al. |
| 6,355,239 | B1 | 3/2002 | Bruder et al. |
| 6,368,636 | B1 | 4/2002 | McIntosh et al. |
| 6,387,367 | B1 | 5/2002 | Davis-Sproul et al. |
| 6,387,369 | B1 | 5/2002 | Pittenger et al. |
| 6,461,645 | B1 | 10/2002 | Boyse et al. |
| 6,497,875 | B1 | 12/2002 | Sorrell et al. |
| 6,541,024 | B1 | 4/2003 | Kadiyala et al. |
| 6,685,936 | B2 | 2/2004 | McIntosh et al. |
| 6,709,864 | B1 | 3/2004 | Pittenger et al. |
| 6,797,269 | B2 | 9/2004 | Mosca et al. |
| 6,835,377 | B2 | 12/2004 | Goldberg et al. |
| 6,863,900 | B2 | 3/2005 | Kadiyala et al. |
| 6,875,430 | B2 | 4/2005 | McIntosh et al. |
| 7,029,666 | B2 | 4/2006 | Bruder et al. |
| 7,045,148 | B2 | 5/2006 | Hariri |
| 7,147,626 | B2 | 12/2006 | Goodman et al. |
| 7,255,879 | B2 | 8/2007 | Hariri |
| 7,311,904 | B2 | 12/2007 | Hariri |
| 7,311,905 | B2 | 12/2007 | Hariri |
| 7,498,171 | B2 | 3/2009 | Hariri et al. |
| 2001/0005591 | A1 | 6/2001 | Qasba et al. |
| 2001/0038836 | A1 | 11/2001 | During et al. |
| 2002/0028510 | A1 | 3/2002 | Sanberg et al. |
| 2002/0086005 | A1 | 7/2002 | Chiu et al. |
| 2002/0123141 | A1 | 9/2002 | Hariri |
| 2002/0132343 | A1 | 9/2002 | Lum |
| 2002/0160510 | A1 | 10/2002 | Hariri |
| 2003/0032179 | A1 | 2/2003 | Hariri |
| 2003/0044977 | A1 | 3/2003 | Sakuragawa et al. |
| 2003/0161818 | A1 | 8/2003 | Weiss et al. |
| 2003/0180269 | A1 | 9/2003 | Hariri |
| 2003/0235563 | A1 | 12/2003 | Strom et al. |
| 2003/0235909 | A1 | 12/2003 | Hariri |
| 2004/0018617 | A1 | 1/2004 | Hwang |
| 2004/0028660 | A1 | 2/2004 | Hariri |
| 2004/0048372 | A1 | 3/2004 | Hariri |
| 2004/0048796 | A1 | 3/2004 | Hariri |
| 2004/0107453 | A1 | 6/2004 | Furcht et al. |
| 2004/0136967 | A1 | 7/2004 | Weiss et al. |
| 2004/0161419 | A1 | 8/2004 | Strom et al. |
| 2004/0171147 | A1 | 9/2004 | Hariri |
| 2004/0180040 | A1 | 9/2004 | Phillips et al. |
| 2004/0219136 | A1 | 11/2004 | Hariri |
| 2004/0229351 | A1 | 11/2004 | Rodriguez et al. |
| 2004/0241144 | A1 | 12/2004 | Kaps et al. |
| 2005/0019865 | A1 | 1/2005 | Kihm et al. |
| 2005/0019908 | A1 | 1/2005 | Hariri |
| 2005/0032209 | A1 | 2/2005 | Messina et al. |
| 2005/0037491 | A1 | 2/2005 | Mistry et al. |
| 2005/0042595 | A1 | 2/2005 | Haas |
| 2005/0054093 | A1 | 3/2005 | Haas |
| 2005/0054098 | A1 | 3/2005 | Mistry et al. |
| 2005/0058629 | A1 | 3/2005 | Harmon et al. |
| 2005/0058630 | A1 | 3/2005 | Harris et al. |
| 2005/0058631 | A1 | 3/2005 | Kihm et al. |
| 2005/0085543 | A1 | 4/2005 | Wallimann et al. |
| 2005/0089513 | A1 | 4/2005 | Sakuragawa et al. |
| 2005/0112104 | A1 | 5/2005 | Pittenger et al. |
| 2005/0118712 | A1 | 6/2005 | Tsai |
| 2005/0118715 | A1 | 6/2005 | Hariri |
| 2005/0124003 | A1 | 6/2005 | Atala et al. |
| 2005/0143420 | A1 | 6/2005 | Moutouh-de Parseval |

| | | | |
|---|---|---|---|
| 2005/0148034 A1 | 7/2005 | Hariri | |
| 2005/0148074 A1 | 7/2005 | Davies et al. | |
| 2005/0176139 A1 | 8/2005 | Chen et al. | |
| 2005/0181502 A1 | 8/2005 | Furcht et al. | |
| 2005/0186182 A1 | 8/2005 | Deisher et al. | |
| 2005/0233452 A1 | 10/2005 | Ho et al. | |
| 2005/0239897 A1 | 10/2005 | Pittenger et al. | |
| 2005/0272148 A1 | 12/2005 | Hariri | |
| 2005/0276792 A1 | 12/2005 | Kaminski | |
| 2005/0283844 A1 | 12/2005 | Furcht et al. | |
| 2006/0008450 A1 | 1/2006 | Verfaillie et al. | |
| 2006/0078993 A1 | 4/2006 | Phan et al. | |
| 2006/0153816 A1 | 7/2006 | Brown et al. | |
| 2006/0153817 A1 | 7/2006 | Kihm et al. | |
| 2006/0153818 A1 | 7/2006 | Dhanaraj et al. | |
| 2006/0154366 A1 | 7/2006 | Brown et al. | |
| 2006/0154367 A1 | 7/2006 | Kihm et al. | |
| 2006/0166361 A1 | 7/2006 | Seyda et al. | |
| 2006/0171930 A1 | 8/2006 | Seyda et al. | |
| 2006/0188983 A1 | 8/2006 | Harris et al. | |
| 2006/0222634 A1 | 10/2006 | Clarke et al. | |
| 2006/0233765 A1 | 10/2006 | Messina et al. | |
| 2006/0233766 A1 | 10/2006 | Messina et al. | |
| 2006/0234376 A1 | 10/2006 | Mistry et al. | |
| 2006/0263337 A1 | 11/2006 | Maziarz et al. | |
| 2006/0281178 A1 | 12/2006 | Sakuragaw et al. | |
| 2007/0020225 A1 | 1/2007 | Abramson et al. | |
| 2007/0021704 A1 | 1/2007 | Hariri et al. | |
| 2007/0021762 A1 | 1/2007 | Liu et al. | |
| 2007/0031384 A1 | 2/2007 | Atala | |
| 2007/0036767 A1 | 2/2007 | Mistry | |
| 2007/0038298 A1 | 2/2007 | Sulner et al. | |
| 2007/0043328 A1 | 2/2007 | Goodman et al. | |
| 2007/0053888 A1 | 3/2007 | Hariri | |
| 2007/0077652 A1 | 4/2007 | Peled | |
| 2007/0092497 A1 | 4/2007 | Hariri | |
| 2007/0134210 A1 | 6/2007 | Heidaran | |
| 2007/0160588 A1 | 7/2007 | Kihm | |
| 2007/0190034 A1 | 8/2007 | Paludan | |
| 2007/0190042 A1 | 8/2007 | Edinger | |
| 2007/0275362 A1 | 11/2007 | Edinger | |
| 2007/0292910 A1 | 12/2007 | Heidaran | |
| 2008/0032401 A1 | 2/2008 | Edinger | |
| 2008/0044848 A1 | 2/2008 | Heidaran | |
| 2008/0069895 A1 | 3/2008 | Liu et al. | |
| 2008/0131410 A1 | 6/2008 | Hariri | |
| 2008/0131522 A1 | 6/2008 | Liu et al. | |
| 2008/0131966 A1 | 6/2008 | Hariri | |
| 2008/0152624 A1 | 6/2008 | Paludan | |
| 2008/0152629 A1 | 6/2008 | Edinger | |
| 2008/0175824 A1 | 7/2008 | Heidaran et al. | |
| 2008/0181935 A1 | 7/2008 | Bhatia et al. | |
| 2008/0181967 A1 | 7/2008 | Liu et al. | |
| 2008/0206343 A1 | 8/2008 | Edinger et al. | |
| 2008/0208158 A1 | 8/2008 | Goodman et al. | |
| 2008/0226595 A1 | 9/2008 | Edinger et al. | |
| 2009/0053805 A1 | 2/2009 | Hariri | |

FOREIGN PATENT DOCUMENTS

| | | | |
|---|---|---|---|
| EP | 1288293 A1 | 3/2003 | |
| EP | 1384775 A1 | 1/2004 | |
| EP | 1535994 A1 | 6/2005 | |
| EP | 1775341 | 4/2007 | |
| JP | 2003235549 | 12/2002 | |
| JP | 2005151907 | 11/2003 | |
| WO | WO90/11354 | 10/1990 | |
| WO | WO91/01140 | 2/1991 | |
| WO | WO91/06667 A1 | 5/1991 | |
| WO | WO93/04169 | 3/1993 | |
| WO | WO95/22611 A2 | 8/1995 | |
| WO | WO96/34035 | 10/1996 | |
| WO | WO96/39101 A1 | 12/1996 | |
| WO | WO98/37903 A1 | 9/1998 | |
| WO | WO99/64566 A2 | 12/1999 | |
| WO | WO00/17325 A1 | 3/2000 | |
| WO | WO00/27999 A3 | 5/2000 | |
| WO | WO00/73421 A2 | 12/2000 | |
| WO | WO01/21767 | 3/2001 | |
| WO | WO01/93909 A2 | 12/2001 | |
| WO | WO02/46373 | 6/2002 | |
| WO | WO02/063962 | 8/2002 | |
| WO | WO02/064755 | 8/2002 | |
| WO | WO03/042405 | 5/2003 | |
| WO | WO03/068937 | 8/2003 | |
| WO | WO03/087392 | 10/2003 | |
| WO | WO03/089619 | 10/2003 | |
| WO | WO2004/087896 | 10/2004 | |
| WO | WO2005/042703 | 5/2005 | |
| WO | WO2005/105992 | 11/2005 | |
| WO | WO2006/015214 | 2/2006 | |
| WO | WO2007/024441 | 3/2007 | |
| WO | WO2007/056578 | 5/2007 | |
| WO | WO2007071048 | 6/2007 | |
| WO | WO2007089293 | 8/2007 | |

OTHER PUBLICATIONS

Majumdar et al. J Cell Physiol 2000;176:57-66.*
Devine et al. Exp Hematol 2001;29:244-55.*
Verfaillie, Stem Cells 1994;12:466-76.*
Delvin et al. J Clin Endocrinol Metab 1985;60:880-5.*
U.S. Appl. No. 11/580,588, filed Oct. 13, 2006, Pauludan.
U.S. Appl. No. 11/580,625, filed Oct. 13, 2006, Heidaran.
U.S. Appl. No. 11/648,802, filed Dec. 28, 2006, Heidaran.
U.S. Appl. No. 11/648,804, filed Dec. 28, 2006, Edinger.
U.S. Appl. No. 11/648,812, filed Dec. 28, 2006, Heidaran.
U.S. Appl. No. 11/648,813, filed Dec. 28, 2006, Edinger.
U.S. Appl. No. 11/648,824, filed Dec. 28, 2006, Heidaran.
Abbott, Hematol Oncol 2003; 21: 115-130.
Abkowitz, "Can Human Hematopoietic Stem Cells Become Skin, Gut, or Liver Cells?" N. Engl. Med. 346(10):770-2 (2002).
Ashihara, et al., "Successful Peripheral blood Stem Cell Transplation for Myelodysplastic Syndrome." Bone Marrow Transplantation, 24 (12:1343-1345) (1999).
Belvedere, et al., "Increased lood Volume and CD34(+)CD38(-) Progenitor Cell Recovery Using a Novel Umbilical Cord Blood Collection System." Stem Cells 18(4): 245-251 (2000).
Bersinger, et al., Reproduct. Fertil. Dev. 4:585-588 (1992).
Cardoso, et al., "Release from Quiescence of CD34+ CD38- Human Umbilical Cord Blood Cells Reveals Their Potentiality to Engraft Adults," Proc. Nat'l, Acad. Sc. USA 90(18): 8707-8711 (1993).
Chao, et al., "Stern Cell Transplantation (Cord Blood Transplants)." American Society of Hematololgy, Hematology 2004, p. 354-71.
Chen, et al. "Intravenous Administration of Human Umbilical Cord Blood Reduces Behavioral Deficits After Stroke in Rats." Stroke 32(11):2682-2688 (2001).
Chen, R. et al., "The Potential for the Use of Mononuclear Cells from Human Umbilical Cord Blood in the Treatment of Amyotrophic Lateral Sclerosis is SOD1 Mice." J. Med. 31(1-2):21-30 (2000).
Chin, et al., "Enhanced Interferon Production and Lymphokine-Activated Cytotoxicty of Human Placental Cells." Cellular Immunology 113, 1-9 (1988).
Cord Blood Stem Cell Transplantation, Medline Mesh Database, 2003.
Cosma, et al., "Use and Application of Stem Cells in Toxicology." SOT 2003 Annual Meeting, p. 4, Abstract 19.
Czarneski, J. et al., "Effects of Cord Blood Transfer on the Hematopoietic Recovery Following Sublethal Irradiation in MRL lpr/lpr Mice." Proc. Soc. Exp. Biol. Med. 220(2):79-87 (1999).
Davila, et al., "Use and Application of Stem Cells in Toxicology." Toxicological Sciences 79, 214-223 (2004).
De Coppi, et al., "Amniotic Fluid and Chorionic Villi Derived Human Stem Cells for the Engineering of Tissues in Vivo." The Journal of Urology, vol. 171, No. 4, Supplement, Saturday, May 8, 2004, p. 21, Abstract 81.

De Coppi, et al., "Human Embryonic and Fetal Stem-Cell Isolation From Amniotic Fluid and Placenta for Tissue Reconstruction." Urology and Reproductive Surgery, vol. 195, No. 3S, Sep. 2002, p. S93.

De Coppi, et al., "Human Fetal Stem Cell Isolation from Amniotic Fluid for Tissue Reconstruction." The Journal of Urology, vol, 167, No, 4, Supplement, Abstract 338 Sunday, May 26, 2002.

De Coppi, et al., "Pluripotent Stem Cells Derived from Human Chorionic Villi and Amniotic Fluid for Tissue Engineering Applications." Experimental Biology/IUPS 2005: Meeting Abstracts, A1366, Abstract 781.7.

De Filippo, et al., "Total Penile Urethra Replacement with Autologous Cell-Seeded Collagen Matrices" Urology and Reproductive Surgery, vol. 195, No. 3S, Sep. 2002, p. S95.

Dorrel, "Expansion of Human Cord Blood CD34+CD38− Cells in Ex Vivo Culture During Retroviral Transduction Without a Corresponding Increase in SCID Repopulation Cell (SRC) Frequency: Dissocation of SRC Phenotype and Function." Blood, 95(1):102-110.

Elchalal, et al., "Postpartum Unbilical Cord Blood Collection for Transplantation: A Comparison of Three Methods." Am.J. of Obstetrics & Gyn. 182(1Pt 1):227-232 (2000).

Emerson, "Ex Vivo Expansion of Hematopoietic Precursors, Progenitors and Stem Cells. The Next Generation of Cellular Therapeutics." Blood 87(8): 3082-3088.

Ende, N., "Berashis Cells in Human Umbilical Cord Blood vs. Embryonic Stem Cells." Journal of Medicine 33(1-4): 167-171 (2002).

Ende, et al, "Collection of Umbilical Cord Blood for Transplantation." Blood (80(6): 1623-1624 (1992).

Ende, N. & Chen, R., "Parkinson's Disease Mice and Human Umbilical Cord Blood." Journal of Medicine 33(1-4):173-180 (2002).

Ende, N. et al., "Human Umbilical Cord Blood Cells Ameliorate Alzheimer's Disease in Transgenic Mice." J. Med., 32(3-4):241-7 (2001).

Ende, N. et al., "Human Umbilical Cord Blood Cells Ameliorate Huntington's Disease in Transgenic Mice." J. Med., 32(3-4):231-40 (2001).

Ende, N. et al. "Human Umbilical Cord Blood Effect on SOD Mice (Amyotrophic Lateral Sclerosis)" Life Sci. 67(1):53-9 (2000).

Ende, N. et al., "Pooled Umbilical Cord Blood as a Possible Universal Donor for Marrow Reconstruction and Use in Nuclear Accidents." Life Sci. 69(13):1531-9 (2001).

Ende, N. et al. "The Effect of Human Cord Blood on SJL/J Mice After Chemoablation and Irradiation and Its Possible Clinical Significance," Immunol. Invest. 24(6):999-1012 (1995).

Ende, N. et al., "The Feasibility of Using Blood Bank-Stored (4 Degrees C) Cord Blood, Unmatched for HLA for Marrow Transplantation." Am. J. Clin. Pathol. 111(6):773-81 (1999).

Erices, et al., Brit. J. Haematol. 2000; 109:235-42.

Gluckman, et al., "Cord Blood Hematopoietic Stem Cells: Biology and Transplantation." In: Hematology, American Society of Hematology Education program book, 1998, p. 1-14.

Gluckman, et al., "Results of Unrelated Umbilical Cord Blood Hematipoietic Stem Cell Transplant." Transfusion Clinique et Biologique 8(3):146-154 (2001).

Hows. "Status of Umbilical Cord Blood Transplantation in the Year 2001." J. Clin. Pathol. 54(6): 428-434 (2001).

Huss, "Isolation of Primary Immortalized CD34- Hematopoietic and Mesenchymal Stem Cells from Various Sources." Stem Cells 2000; 18:1-9.

Huss, "Perspectives on the Morphology and Biology of CD34-Negative Stem Cells." Journal of Hematotherapy & Stem Cell Research 9:783-793 (2000).

Koh, et al., "Parthenolgenetically Derived Stem Cells for Urologic Reconstruction." The Journal of Urology, vol. 171, No. 4, Supplement, Saturday, May 8, 2004, p. 21, Abstract 81.

Kondo, et al., "Reduced Interferon Gamma Production by Antigen-Stimulated Cord Blood Monoclear Cells is a Risk Factor of Allergic Disorders—6-Year Follow-up Study." Clin. Exp. Allergy 28(11)1340-1344 (1998).

Korbling, et al., "Hepatocytes and Epithelial Cells of Donor Origin in Recipients of Peripheral-Blood Stem Cells." N. Engl. J. Med. 346(10):738-46.

Korbling et al. "Peripheral Blood Stem Cell Versus Bone Marrow Allotransplantation; Does the Source of Hematopoietic Stem Cells Matter?" Blood 98(10):2900-2908 (2001).

Kurtzberg, et al., New Eng. J. Med. 335:157-166 (1996).

Larsson, et al., Angiogenesis 5,107-110 (2002).

Liu, et al., Bone Marrow Transplant 1999; 24:247-52.

Ma, et al., Tissue engineering 5:91-102 (1999).

MacLaren, et al., J. Comp. Pathol. 106:279-297 (1992).

Madri, et al., J. Cell Biol. 97:153-165 (1983).

Melchner, et al., "Human Placental Conditioned Medium Reverses Apparent Commitment to Differentiation of Human Promyeloctic Lekemia Cells (HL60)."Blood. (66(6):1469-72 (1985).

Miki, et al., "Isolation of Multipotent Stem Cells from Placenta." AASLD Abstracts, Hepatology, Oct. 2003, Abstract 279, p. 290A.

Miki, et al., "Production of Hepatocytes from Human Amniotic Stem Cells." Hepatology, Abstract 20, vol. 36, No. 4, Pt. 2, 2002.

Miki, et al., "Stem Cell Characteristics of Amniotic Epithelial Cells." Stem Cells Express, published online Aug. 9, 2005; doi:10. 1634/ stemcells.2004-0357.

Minguel, et al., Exp. Biol. Med. 226:507-520 (2001).

Muhlemann, et al., Placenta 16:367-373 (1995).

Oppenheim, et al., Theriogenology 55:1657-1581 (2001).

Ordi, et al., Am. J. Surg. Pathol. 8:1006-1011 (1998).

Papaioannou, et al., Stem Cell Handbook 2004, 19-31.

Pesce, et al., Stem Cells 2001; 19:271-8.

Rameshwar, P. et al, "Endogenous Hematopoietic Reconstruction Induced by Human Umbilical Cord Blood Cells in Immunocompromised Mice: Implications for Adoptive Therapy." Exp. Hematol. 27(1):176-85 (1999).

Reyes, et al. "Origin of Endothelial Progenitors in Human Postnatal Bone Marrow." J. Clin. Invest. 109(3):337-46.

Sakabe, et al., "Functional Difference Between Subpopulations of Mobilized Peripheral Blood-Derived CD34+ Cells Expressing different Levels of HLA-DR, CD33, CD38 and C-Kit Antigens." Stem Cells 15(11): 73-81 (1997).

Sakuragawa et al., "Expression of Markers for Both Neuronal and Glial Cells in Human Amniotic Epithelial Cells," Neuroscience Letters 209 (1996), 9-12.

Sakuragawa, et al., "Human Amniotic Epithelial Cells are Promising Transgene Carriers for Allogeneic Cell Transplantation into Liver." J. Hum. Genet. (2000) 45: 171-176.

ScienCell—Human Amniotic Epithelial Cells. http://www.sciencel-lonline.corn/products/7100.htm.

Shamblott, et al., "Derivation of pluripotent stem cells from cultured human primordial germ cells." Proc. Natl. Acad. Sci. U S A 95:13726-13731 (1998). Erratum in: Proc. Natl. Acad. Sci. U S A 96:1162 (1999).

Srour, "Ex Vivo Expansion of Hematopoietic Stem and Progenitor Cells. Are We There Yet?" The Journal of Hematotherapy 8:93-102 (1999).

Stromberg, et al., Methods in Cell Biol. 21: 227-252 (1980).

Turner, et al., "A Modified Harvest Technique for Cord Blood Hematopoietic Stern Cells." Bone Marrow Transplantation 10:89-91 (1992).

Van Bekkum, "The Pluripotent Hemopoietic Stem Cell: Its Identification and Applications." Verh, Dtsch, Ges. Pathol. 74: 19-24 (1990).

Viacord, "Umblicical Cord Blood Can Save Lives." (Information Brochure), Boston: ViaCell CENTR-BRO R1 Oct. 2001.

Vilmer, et al., "HLA-Mismatched Cord Blood Transplantation: Immunological Studies," Blood Cells 20(2-3):242-244 (1994).

Wang, et al., "Enhanced recovery of hematopoietic progenitor and stem cells from cultivated postpartum human placenta." Blood 98(11/1):183a, abstract No. 769 (2001).

Wobus, et al., Physiol. Rev. 2005; 85:635-78.

Ye, et al., "Recovery of Placental-Derived Adherent Cells with Mesenchymal Stem Cell Characteristics." Blood 98(11/1):147b Abstracts No. 4260.

U.S. Appl. No. 11/877,475, filed Oct. 23, 2007, Edinger.

U.S. Appl. No. 11/982,211, filed Oct. 31, 2008, Heidaran.

U.S. Appl. No. 12/030,161, filed Feb. 12, 2008, Edinger.

U.S. Appl. No. 12/030,170, filed Feb. 12, 2008, Edinger.

Office Action dated May 7, 2003 in U.S. Appl. No. 10/004,942, now U.S. Patent No. 7,045,148.

Office Action dated Dec. 5, 2003 in U.S. Appl. No. 10/004,942, now U.S. Patent No. 7,045,148.
Office Action dated Jun. 15, 2004 in U.S. Appl. No. 10/004,942, now U.S. Patent No. 7,045,148.
Office Action dated Dec. 16, 2004 in U.S. Appl. No. 10/004,942, now U.S. Patent No. 7,045,148.
Office Action dated Jun. 20, 2005 in U.S. Appl. No. 10/004,942, now U.S. Patent No. 7,045,148.
Notice of Allowance in U.S. Appl. No. 10/004,942, now U.S. Patent No. 7,045,148.
Office Action dated Sep. 23, 2004 in U.S. Appl. No. 10/074,976, now U.S. Patent No. 7,311,904.
Office Action dated Jan. 5, 2006 in U.S. Appl. No. 10/074,976, now U.S. Patent No. 7,311,904.
Office Action dated Sep. 20, 2006 in U.S. Appl. No. 10/074,976, now U.S. Patent No. 7,311,904.
Office Action dated Mar. 27, 2007 in U.S. Appl. No. 10/074,976, now U.S. Patent No. 7,311,904.
Notice of Allowance in U.S. Appl. No. 10/074,976, now U.S. Patent No. 7,311,904.
Office Action dated Jan. 19, 2006 in U.S. Appl. No. 10/366,671, now U.S. Patent No. 7,311,905.
Office Action dated Oct. 10, 2006 in U.S. Appl. No. 10/366,671, now U.S. Patent No. 7,311,905.
Office Action dated May 14, 2007 in U.S. Appl. No. 10/366,671, now U.S. Patent No. 7,311,905.
Notice of Allowance in U.S. Appl. No. 10/366,671, now U.S. Patent No. 7,311,905.
Office Action dated Jan. 19, 2006 in U.S. Appl. No. 10/640,428, now U.S. Patent No. 7,255,879.
Office Action dated Oct. 18, 2006 in U.S. Appl. No. 10/640,428, now U.S. Patent No. 7,255,879.
Notice of Allowance in U.S. Appl. No. 10/640,428, now U.S. Patent No. 7,255,879.
Office Action dated Oct. 4, 2005 in U.S. Appl. No. 10/721,144.
Office Action dated Jan. 11, 2006 in U.S. Appl. No. 10/721,144.
Office Action dated Jun. 14, 2006 in U.S. Appl. No. 10/721,144.
Office Action dated Dec. 28, 2006 in U.S. Appl. No. 10/721,144.
Office Action dated Jun. 27, 2007 in U.S. Appl. No. 10/721,144.
Office Action dated Feb. 5, 2008 in U.S. Appl. No. 10/721,144.
Office Action dated Apr. 20, 2007 in U.S. Appl. No. 11/187,400.
Office Action dated Jan. 4, 2008 in U.S. Appl. No. 11/187,400.
Office Action dated Dec. 13, 2007 in U.S. Appl. No. 10/874,828.
Office Action dated Apr. 6, 2007 in U.S. Appl. No. 10/874,828.
Office Action dated Jun. 12, 2006 in U.S. Appl. No. 10/874,828.
Office Action dated Sep. 9, 2008 in U.S. Appl. No. 10/874,828.
Addison, et al., "Metabolism of Prednisolone by the Isolated Perfused Human Placental Lobule." J. Ster. Biochem. Mol. Biol., vol. 39, No. 1, pp. 83-90 (1991).
Anker In'T P et al, "Isolation of Mesenchymal Stem Cells of Fetal or Maternal Origin from Human lacenta," Stem Cells, Alphamed Press, Dayton, OH, US, vol. 22, No. 7, 004, pp. 1338-1345.
Campagnoli et al., Blood Oct. 15, 2001; 98(8):2396-402.
Caplan, "The Mesengenic Process," Clin Plast Surg (1994) 21(3):429-435.
Clark David A et al, "Placental trophoblast from successful human pregnancies expresses the tolerance signaling molecule, CD200 (OX-2)" American Journal of Reproductive immunology, Munksgaard International Publishers, Copenhagen, DK, vol. 50, No. 3, Sep. 2003, pp. 187-195, XP002430047 ISSN: 1046-7408.
Contractor, et al., "A Comparison of the Effects of Different Perfusion Regimes on the Structure of the Isolated Human Placental Lobule." Cell Tissue Res. 237: 609-617 (1984).
Drake, P.M. et al., "Human Placental Cytotrophoblasts Attract Monocytes and CD56 (bright) Natural Killer Cells Via the Actions of Monocyte Inflammatory Protein 1alpha," The Journal of Experimental Medicine (2001) 193(10):1199-1212.
Ende, M. et al., "Hemapoetic Transplantation By Means of Fetal (Cord) Blood: A New Method," Va Med Mon 99:276-280 (1972).
Fasouliotis et al., "Human umbilical cord blood banking and transplantation: a state of the art," Eur. J. Obstet. Gynecol. Reprod. Biol. 90(1):13-25 (2000).

Frank H G, et al., "Cell culture models of human trophoblast: primary culture of trophoblast—a workshop report." Placent APR 2001, vol. 22 Suppl A, Apr. 2001, pp. S107-S109, XP002443188 ISSN: 0143-4004.
Harbacheuski, et al., "Placenta Derived Adherent Cells (PDACs) Suppress Tumor Cells of Diverse Origin." Blood, vol. 108, No. 11, Part 2, Nov. 2006, p. 288b.
Igura, K., et al., "Isolation and Characterization of Mesencymal Progenitor Cells from Chorionic Villi of Human Placenta," Cytotherapy (2004) 6(6): 543-553.
Kawata et al., "Transcriptional Control of HLA-A,B,C Antigen in Human Placental Cytotrophoblast Isolated Using Trophoblast- and HLA-Specific Monoclonal Antibodies and the Fluorescence-Activated Cell Sorter," J. Exp. Med. 160(3):633-51 (1984).
Lebkowski, Cancer J. Nov.-Dec. 7, 2001 Suppl. 2:S83-93.
Leonard et al., "The Role of ABC Transporters in Clinical Practice," Oncologist. (2003) 8:411-424.
Li Chang Dong et al, "Mesenchymal stem cells derived from human placenta suppress allogeneic umbilical cord blood lymphocyte proliferation," Cell Research—XIBAO YANJIU Beijing, CN, vol. 15, No. 7, Jul. 2005, pp. 539-547, XP009080356 ISSN: 1001-0602.
Ma et al., "Development of an in vitro human placenta model by the cultivation of human ytophoblasts in a fier-based bioreactor system," Tissue Engineering (1995) 5:91-102.
McMaster, M. et al., "Human Placental HLA-G Expression is Restricted to Differentiated Cytotrophoblasts," Journal of Immunology, The Williams and Wilkins Co. (1995) 154(8): 3771-3778.
Moore, et al., "A Simple Perfusion Technique for Isolation of Maternal Intervillous Blood Mononuclear Cells from Human Placentae." J. Immunol. Methods, 209: 93-104 (1997).
Myllynen "In Search of Models for Hepatic and Placental Pharmacokinetics," [Dissertation] University of Oulu, 2003.
Paludan, et al., "Immune Suppression by Placenta Derived Adherent Cells (PDAC) Correlate with Monocyte Chemoattractant Protein-1 and IL-2 Secretion." Blood 108: abstract only (2006).
Pera et al., j. Cell. Sci. (2000) 113:5-10.
Pittenger, M. F., et al. "Multilineage Potential of Adult Human Mesenchymal Stem Cells." Science (1999) U.S. vol. 284, No. 5411, pp. 143-147.
Reyes et al., "Purification and Ex Vivo Expansion of Postnatal Human marrow Mesodermanl Progenitor Cells," Blood (2001) 98(9):2615-2625.
Roth, I., et al. "Human Placental Cytotrophoblats Produce the Immunosuppressive Cytokine Interliukin 10," The Journal of Experimental Medicine (1996) 184(2): 539-548.
Schutz et al., 1996, Isolation and cultivation of endothelial cells derived from human placenta. EJCB 71, 395-401.
Sirchia et al., Haematologica 1999; 84:738-747.
Thomson, et al., "Embryonic Stem Cell Lines Derived from Human Blastocysts." Science 282(5391):1145-47 (1998).
Woods et al., "Osomometric and permeability characteristics of human placental/umbilical cord blood CD34+ cells and their application to cryopreservation," J. Hemaother. Stem Cell Res. 9(2):161-173 (2000).
Yen B. Linju et al, "Isolation of multipotent cells from human term placenta" Stem Cells (Dayton, Ohio) 2005, vol. 23, No. 1, Jan. 2005, pp. 3-9, XP002143187 ISSN: 1065-5099.
Zhang Yi et al. "Human placenta-derived mesenchymal progenitor cells support culture expansion of long-term culture-initiating cells from cord blood CD34+ Cell" Experimental Hematology, New, NY, US, vol. 32, No. 7, Jul. 2004, pp. 657-664, XP002389863 ISSN: 03101-472X.
U.S. Appl. No. 09/659,904, filed Sep. 12, 2000, Hariri.
U.S. Appl. No. 12/187,337, filed Aug. 6, 2008, Heidaran et al.
U.S. Appl. No. 12/240,956, filed Sep. 29, 2008, Zhang et al.
U.S. Appl. No. 12/267,499, Nov. 7, 2008, Heidaran et al.
U.S. Appl. No. 12/341,961, filed Dec. 22, 2008, Hariri.
U.S. Appl. No. 12/396,397, filed Mar. 2, 2009, Hariri et al.
Advisory Action dated Jul. 12, 2004 in U.S. Appl. No. 10/076,180.
Advisory Action dated Feb. 2, 2007 in U.S. Appl. No. 10/366,671, now U.S. Patent No. 7,311,905.
Office Action dated May 18, 2006 in U.S. Appl. No. 10/411,655, now U.S. Patent No. 7,498,171.

Office Action dated Nov. 20, 2006 in U.S. Appl. No. 10/411,655, now U.S. Patent No. 7,498,171.
Office Action dated Jul. 11, 2007 in U.S. Appl. No. 10/411,655, now U.S. Patent No. 7,498,171.
Office Action dated Feb. 28, 2008 in U.S. Appl. No. 10/411,655, now U.S. Patent No. 7,498,171.
Notice of Allowance dated Oct. 30, 2008 in U.S. Appl. No. 10/411,655, now U.S. Patent No. 7,498,171.
Office Action dated Aug. 29, 2006 in U.S. Appl. No. 10/449,248.
Office Action dated Apr. 26, 2007 in U.S. Appl. No. 10/449,248.
Office Action dated Feb. 7, 2008 in U.S. Appl. No. 10/449,248.
Office Action dated Dec. 5, 2007 in U.S. Appl. No. 10/511,354.
Office Action dated Jun. 2, 2008 in U.S. Appl. No. 10/511,354.
Advisory Action dated Nov. 14, 2008 in U.S. Appl. No. 10/511,354.
Office Action dated Feb. 17, 2008 in U.S. Appl. No. 10/511,354.
Office Action dated Dec. 6, 2005 in U.S. Appl. No. 10/511,355.
Office Action dated Aug. 4, 2006 in U.S. Appl. No. 10/511,355.
Advisory Action dated Jan. 29, 2007 in U.S. Appl. No. 10/511,355.
Office Action dated Sep. 5, 2007 in U.S. Appl. No. 10/511,355.
Advisory Action dated Feb. 20, 2007 in U.S. Appl. No. 10/640,428, now U.S. Patent No. 7,255,879.
Advisory Action dated Feb. 6, 2006 in U.S. Appl. No. 10/721,144.
Office Action dated Sep. 9, 2008 in U.S. Appl. No. 10/874,828, now U.S. Patent No. 7,468,276.
Notice of Allowance dated Oct. 14. 2008 in U.S. Appl. No. 10/874,828, now U.S. Patent No, 7,468,276.
Office Action dated May 22, 2008 in U.S. Appl. No. 11/187,400.
Office Action dated Feb. 20, 2009 in U.S. Appl. No. 11/187,400.
Advisory Action dated Sep. 8, 2008 in U.S. Appl. No. 11/187,400.
Office Action dated Jan. 26, 2009 in U.S. Appl. No. 11/648,813.

* cited by examiner

CO-CULTURE OF PLACENTAL STEM CELLS AND STEM CELLS FROM A SECOND SOURCE

This application is a continuation-in-part of U.S. application Ser. No. 10/366,671, filed Feb. 13, 2003, now U.S. Pat. No. 7,311,905 which is a continuation-in-part of U.S. application Ser. No. 10/076,180, filed Feb. 13, 2002, now abandoned, and which claims benefit of U.S. Provisional Application No. 60/437,292 filed Dec. 13, 2002; and claims benefit of U.S. Provisional Application No. 60/754,692, filed Dec. 29, 2005, the disclosures of each of which are hereby incorporated by reference herein.

1. INTRODUCTION

The present invention provides in vitro and in vivo methods for optimizing the ratio of a placenta-derived stem cell population to a stem and/or progenitor cell population from a second source to create a combined stem cell population having improved engraftment potential over populations of placental stem cells, or stem cells from the second source, alone. The present invention also provides combined stem cell populations comprising placenta-derived stem cells and stem or progenitor cells derived from a second source, wherein the combination shows improved engraftment as compared to placental stem cells or the stem cells from a second source, alone. In accordance with the present invention, placenta-derived stem cells may be combined with, e.g., umbilical cord blood-derived stem or progenitor cells, fetal or neonatal stem cells or progenitor cells, adult stem cells or progenitor cells, hematopoietic stem cells or progenitor cells, stem or progenitor cells derived from bone marrow, etc. The combined stem cell populations may be transplanted into an individual in need of a transplantation of stem cells, for example, an individual who has undergone myeloablative therapy and requires re-establishment of an immune and hematopoietic system, or an individual having a disease, disorder or condition treatable by the introduction to said individual of stem cells. The combined stem cell populations may be used to treat any condition that would benefit from administration of stem cells, including blood disorders such as anemia, neurological disorders, immune disorders, and the like.

2. BACKGROUND OF THE INVENTION

Human stem cells are totipotential, pluripotential or multipotential precursor cells capable of generating a variety of mature human cell lineages. Stem cells can be employed to repopulate many, if not all, tissues and restore physiologic and anatomic functionality. For example, cell populations containing stem cells have been used in transplants to restore partial or full hematopoietic function in patients who have undergone ablative therapy.

Recently, Hariri has reported the isolation of stem cells from mammalian placentas, and the characterization of those stem cells. See Hariri, U.S. Application Publication No. 2002/0123141 "Method of Collecting Placental Stem Cells," Hariri, U.S. Application Publication No. 2002/0160510 "Renovation and Repopulation of Decellularized Tissues and Cadaveric Organs by Stem Cells," Hariri, U.S. Application Publication No. 2003/0032179 "Post-partum Mammalian Placenta, Its Use and Placental Stem Cells Therefrom," and Hariri, U.S. Application Publication No. 2003/0180269 "Embryonic-like Stem Cells Derived From Post-partum Mammalian Placenta, and Uses and Methods of Treatment Using Said Cells".

Many different types of mammalian stem cells have been characterized. See, e.g., Caplan et al., U.S. Pat. No. 5,486,359 (human mesenchymal stem cells); Hu et al., WO 00/73421 (methods of isolation, cryopreservation, and therapeutic use of human amniotic epithelial cells); Boyse et al., U.S. Pat. No. 5,004,681 (fetal and neonatal hematopoietic stem and progenitor cells); Boyse et al., U.S. Pat. No. 5,192,553 (same); Beltrami et al., Cell 114(6):763-766 (2003) (cardiac stem cells); Forbes et al., J. Pathol. 197(4):510-518 (2002) (hepatic stem cells).

The success of transplantation of stem cells is significantly related to the numbers of engraftable cells administered. The number of engraftable cells in, for example, a unit of cord blood, and the amount of cord blood, that may be obtained from a single donor can vary by two orders of magnitude. See, e.g., Gluckman, Hematology, American Society of Hematology Education Program Book, 1-14 (1998). Therefore, a need exists for a method for improvement of the engraftment potential of units of cord blood, cord blood-derived nucleated cells, or other stem cells, especially prior to transplantation.

3. SUMMARY OF THE INVENTION

The present invention provides a method of determining ratios of placenta-derived stem cells to stem cells from a second source to produce stem cell populations that produce greater numbers of colony-forming units, or improved engraftment in vivo, compared to placental stem cells or stem cells from a second source, alone. The present invention provides methods for enhancing and/or accelerating the engraftment potential of cultures or units of stem cells, progenitor cells, or tissues containing stem or progenitor cells, e.g., cord blood, and combinations thereof. In particular, the invention provides methods and compositions for enhancing and/or accelerating the engraftment potential of a combination of placental stem cells and stem cells from a second source, e.g., umbilical cord blood or placental blood, or of stem cells derived therefrom. Such populations are referred to herein as "combined stem cell populations". The invention further provides in vivo uses for the combined stem cell populations. In a preferred embodiment, the placental stem cells are placental stem cells contained within a population of cells obtained from placental perfusate.

In one embodiment, the invention provides a method of identifying a ratio of placental stem cells to stem cells from a second source, comprising identifying a ratio of placental stem cells to stem cells from a second source in a total number of cells that, when said placental stem cells and stem cells from a second source are cultured together for a time and under conditions sufficient to allow the formation of colony-forming units, produces a greater number of colony-forming units than a number of placental stem cells or a number of stem cells from a second source, equivalent to said total number of cells, alone, thereby identifying said combination as a combined stem cell population. In a specific embodiment, said combined stem cell population improves engraftment in an individual in need of stem cells when said combined stem cell population is transplanted into said individual, compared to the transplantation of a number of placental stem cells equivalent to said number of cells, or stem cells from a second source equivalent to said number of cells, alone.

In another embodiment, the invention provides a method of identifying a combined stem cell population comprising contacting in vitro placental stem cells with stem cells from a second source in a plurality of ratios, for a time and under conditions that allow the formation of colony-forming units, and identifying a ratio within said plurality of ratios that produces the greatest number of colony-forming units, wherein said placental stem cells and said stem cells from a second source, when combined in said ratio, are identified as a combined stem cell population. In a specific embodiment, said combined stem cell population improves engraftment in an individual in need of stem cells when said combined stem cell population is transplanted into said individual.

In more specific embodiments, said combined stem cell population improves engraftment in an individual in need of stem cells at least, or at, 1, 2, 3, 4, 5, 6, 7, 8, 9, 10, 11, 12, 13, 14, 15, 16, 17, 18, 19, 20 or 21 days post-transplant. In another more specific embodiment, said combined stem cell population improves engraftment in an individual in need of stem cells at least, or at, more than 21 days post-transplant. In specific embodiments, said combined stem cell population improves engraftment in an individual in need of stem cells at least, or at, more than 25, 30, 35, 40, 45, 50, 55 weeks, or 1 year or longer post-transplant.

In another specific embodiment, said contacting comprises culturing said placental stem cells and said stem cells from a second source in the same physical space. In another specific embodiment, said contacting comprises culturing said placental stem cells and said stem cells from a second source in separate physical spaces in shared culture medium.

In another embodiment, said stem cells from a second source are stem cells derived from cord blood. In another embodiment, placental stem cells comprise $CD34^+$ cells, for example, $CD34^+CD38^+$ cells and/or $CD34^+CD38^-$ cells. In another embodiment, placental stem cells comprise cells that express one or more of markers CD10, CD29, CD44, CD54, CD90, CD73 or CD105, and lack one or more of markers CD34, CD38, CD45, SSEA3 and SSEA4. In another embodiment, placental stem cells comprise cells that are positive for CD10, CD29, CD44, CD54, CD90, CD73 or CD105, and negative for CD34, CD38, CD45, SSEA3 and SSEA4. In another embodiment, placental stem cells comprise cells that comprise one or more of markers CD10, CD29, CD44, CD54, CD90, CD73 and CD105, and lack one or more of markers CD34, CD38, CD45, SSEA3 and SSEA4. In another embodiment, placental stem cells comprise cells that are positive for CD10, CD29, CD44, CD54, CD90, CD73 and CD105, and negative for CD34, CD38, CD45, SSEA3 and SSEA4. In another embodiment, said placental stem cells comprise $CD34^-$ cells. In a specific embodiment, said placental stem cells are $CD34^-CD38^-$ placental stem cells. In another embodiment, said placental stem cells are $OCT-4^+$ or $ABC-p^+$. In a more specific embodiment, said placental stem cells are $OCT-4^+$ and $ABC-p^+$. In another embodiment, said placental stem cells comprise cells that are positive for CD10, CD29, CD33, CD44, CD73, CD105, CD117, and CD133, and negative for CD34 or CD45. In a more specific embodiment, said placental stem cells comprise cells that are $HLA-ABC^+$. In a more specific embodiment, said placental stem cells comprise cells that are $HLA-ABC^-$. In a more specific embodiment, said placental stem cells comprise cells that are $HLA-DR^+$. In a more specific embodiment, said placental stem cells comprise cells that are $HLA-DR^-$. In another specific embodiment, the placental stem cells comprise cells that are $CD200^+$ and $HLA-G^+$. In another specific embodiment, the placental stem cells comprise cells that are $CD73^+$, $CD105^+$ and $CD200^+$. In another specific embodiment, the placental stem cells comprise cells that are $CD200^+$ and $OCT-4^+$. In another specific embodiment, the placental stem cells comprise cells that are $CD73^+$, $CD105^+$ and facilitate the formation of embryoid-like bodies in a population of isolated placental cells comprising said stem cells, when said population is cultured under conditions that allow the formation of embryoid-like bodies. In another specific embodiment, the placental stem cells comprise cells that are $CD73^+$, $CD105^+$ and $HLA-G^+$. In another specific embodiment, the placental stem cells comprise cells that are $OCT-4^+$ and facilitate the formation of embryoid-like bodies in a population of isolated placental cells comprising said stem cells, when said population is cultured under conditions that allow the formation of embryoid-like bodies.

In a specific embodiment, said placental stem cells are obtained from a single placenta. In another specific embodiment, said placental stem cells are obtained from a plurality of placentas. In another specific embodiment, said placental stem cells are obtained from placental perfusate. In another specific embodiment, said placental stem cells are obtained from said placenta by perfusion of said placenta with a perfusion solution. In a more specific embodiment, said perfusion solution comprises a protease or a mucolytic enzyme. In another specific embodiment, said placental stem cells are obtained by physical disruption of the placenta, or a part of the placenta. In a more specific embodiment, said physical disruption comprises contacting said placenta with a protease or mucolytic enzyme. In an even more specific embodiment, said protease is a collagenase (e.g., collagenase I, collagenase IV), trypsin (e.g., trypsin-EDTA), elastase, dispase, or a combination thereof. In another even more specific embodiment, said mucolytic enzyme is hyaluronidase.

In another specific embodiment, said stem cells from a second source are cord blood-derived stem cells. In a more specific embodiment, said cord blood-derived cells are hematopoietic stem cells. In another more specific embodiment, said cord blood-derived cells are non-hematopoietic stem cells. In another specific embodiment, said placental stem cells and stem cells from a second source are combined in suspension. In another specific embodiment, the method additionally comprises adding to said combination a bioactive molecule. In a more specific embodiment, said bioactive molecule is a cytokine or growth factor.

The present invention also provides a combined stem cell population comprising a number of cells in vitro, said number of cells comprising placental stem cells and stem cells from a second source, wherein said combined stem cell population, when cultured for a time and under conditions that allow the formation of colony-forming units, produces more colony-forming units than a number of placental stem cells equivalent to the number of cells in the combined stem cell population or a number of stem cells from a second source equivalent to the number of cells in the combined stem cell population, alone. The present invention further provides a combined stem cell population comprising a number of placental stem cells and stem cells from a second source in vitro, wherein transplantation of said combined stem cell population enhances engraftment of said stem cells compared to transplantation of a number of said placental stem cells equivalent to the number of cells in the combined stem cell population or a number of stem cells from a second source equivalent to the number of cells in the combined stem cell population, alone. In another specific embodiment, the combined stem cell population comprises said placental stem cells and said stem cells from a second source in a ratio, out a plurality of ratios, that, when cultured under conditions allowing the formation of colony forming units, produces the most colony forming units. In a specific embodiment, said stem cells from a second source are cord blood stem cells, bone marrow stem cells, hematopoietic stem cells, or mesenchymal stem cells. In a more specific embodiment, said hematopoietic stem cells are cord blood hematopoietic stem cells. In another more specific embodiment, said hematopoietic stem cells are CD34$^+$ cells. In another specific embodiment, said placental stem cells comprise CD34$^+$ cells. In another specific embodiment, said placental stem cells comprise CD34$^-$ cells. In another specific embodiment, said placental stem cells comprise cells that are OCT4$^+$ or ABC-p$^+$. In another specific embodiment, said placental stem cells comprise cells that are CD34$^+$ and cells that are OCT4$^+$ or ABC-p$^+$. In another specific embodiment, said placental stem cells are contained within placental perfusate substantially lacking red blood cells and cellular debris. In another specific embodiment, the placental stem cells comprise, or are, placental stem cells isolated from placental perfusate. In another specific embodiment, the placental stem cells are contained within total nucleated cells from placental perfusate. In another specific embodiment, said placental stem cells are contained within a population of cells obtained from placental perfusate. In another specific embodiment, said composition comprises placental cells isolated from enzyme-digested placental tissue. In another specific embodiment, said placental stem cells and said stem cells from a second source are obtained from the same individual. In another specific embodiment, said placental stem cells and said stem cells from a second source are obtained from different individuals. In another specific embodiment, said placental stem cells are derived from a plurality of placentas. In another specific embodiment, said stem cells from a second source are obtained from a plurality of individuals.

In another embodiment, placental stem cells in said combined stem cell population comprise CD34$^+$ cells, for example, CD34$^+$CD38$^+$ cells and/or CD34$^+$CD38$^-$ cells. In another embodiment, placental stem cells comprise cells that express one or more of markers CD10, CD29, CD44, CD54, CD90, CD73 or CD105, and lack one or more of markers CD34, CD38, CD45, SSEA3 and SSEA4. In another embodiment, placental stem cells comprise cells that are positive for CD10, CD29, CD44, CD54, CD90, CD73 or CD105, and negative for CD34, CD38, CD45, SSEA3 and SSEA4. In another embodiment, placental stem cells comprise cells that comprise one or more of markers CD10, CD29, CD44, CD54, CD90, CD73 and CD105, and lack one or more of markers CD34, CD38, CD45, SSEA3 and SSEA4. In another embodiment, placental stem cells comprise cells that are positive for CD10, CD29, CD44, CD54, CD90, CD73 and CD105, and negative for CD34, CD38, CD45, SSEA3 and SSEA4. In another embodiment, said placental stem cells comprise CD34$^-$ cells. In a specific embodiment, said placental stem cells are CD34$^-$CD38$^-$ placental stem cells. In another embodiment, said placental stem cells are OCT-4$^+$ or ABC-p$^+$. In a more specific embodiment, said placental stem cells are OCT-4$^+$ and ABC-p$^+$. In another embodiment, said placental stem cells comprise cells that are positive for CD10, CD29, CD33, CD44, CD73, CD105, CD117, and CD133, and negative for CD34 or CD45. In a more specific embodiment, said placental stem cells comprise cells that are HLA-ABC$^+$. In a more specific embodiment, said placental stem cells comprise cells that are HLA-ABC$^-$. In a more specific embodiment, said placental stem cells comprise cells that are HLA-DR$^+$. In a more specific embodiment, said placental stem cells comprise cells that are HLA-DR$^-$. In another specific embodiment, the placental stem cells comprise cells that are CD200$^+$ and HLA-G$^+$. In another specific embodiment, the placental stem cells comprise cells that are CD73$^+$, CD105$^+$ and CD200$^+$. In another specific embodiment, the placental stem cells comprise cells that are CD200$^+$ and OCT-4$^+$. In another specific embodiment, the placental stem cells comprise cells that are CD73$^+$, CD105$^+$ and facilitate the formation of embryoid-like bodies in a population of isolated placental cells comprising said stem cells, when said population is cultured under conditions that allow the formation of embryoid-like bodies. In another specific embodiment, the placental stem cells comprise cells that are CD73$^+$, CD105$^+$ and HLA-G$^+$. In another specific embodiment, the placental stem cells comprise cells that are OCT-4$^+$ and facilitate the formation of embryoid-like bodies in a population of isolated placental cells comprising said stem cells, when said population is cultured under conditions that allow the formation of embryoid-like bodies.

In another embodiment, placental stem cells, or stem cells from a second source, in said combined stem cell population comprise CD34$^+$ cells that are positive for aldehyde dehydrogenase (ALDH). Such cells demonstrate detectable levels of ALDH activity in an ALDH assay. Thus, in various embodiments, a combined stem cell population of the invention comprises CD34+ stem cells, where at least about 5%, 10%, 15%, 20%, 25%, 30%, 35%, 40%, 45%, 50%, 55%, 60%, 65%, 70%, 75%, 80%, 85%, 90%, or at least 95% of the CD34$^+$ stem cells are ALDH$^+$.

The present invention also provides pharmaceutical compositions that comprise combined stem cell populations, e.g., placental perfusate, placental enzymatic digestate, or placental stem cells derived therefrom, combined with umbilical cord blood or umbilical cord blood-derived stem cells, in a pharmaceutically-acceptable carrier. In various specific embodiments, the placental stem cells in said combined stem cell population can be derived from a single donor, or from a plurality of donors; the stem cells from a second source may be derived from a single donor, or from a plurality of donors; or both the placental stem cells and the stem cells from a second source may be derived from single donor, or from a plurality of donors. The combined stem cell populations useful in the methods of the invention may comprise stem cell populations that are partially or completely non-HLA matched to an intended recipient, as well as stem or progenitor cell populations that are completely HLA-matched to an intended recipient.

Combined stem cell populations, e.g., umbilical cord blood supplemented with placental perfusate or placental perfusate-derived stem and/or progenitor cells in an optimum ratio, have a multitude of uses, including prophylactic, therapeutic and diagnostic uses. In one embodiment of the invention, the combined stem cell populations comprising placental stem cells and stem cells from a second source are used to renovate and repopulate tissues and organs, thereby replacing or repairing diseased tissues, organs or portions thereof. In another embodiment, the combination stem cell populations comprising placental stem cells and stem cells from a second source are used to promote re-establishment of hematopoiesis in individuals that have undergone partial or complete myeloablation. In another embodiment, the combination stem cell populations are used to promote re-establishment of hematopoiesis in an individual that has been exposed to a lethal or sub-lethal dose of radiation.

The present invention also provides methods of transplantation, and of treating an individual in need thereof, by administration of a combined stem cell population, comprising transplanting to said individual a number of placental stem cells and stem cells from a second source in a ratio, wherein said combined stem cell population exhibits improved engraftment as compared to transplanting a number of placental stem cells equivalent to the number of cells in the combined stem cell population or a number of stem cells from a second source equivalent to the number of cells in the combined stem cell population, alone. In more specific embodiments, transplantation of said combined stem cell population improves engraftment in an individual in need of stem cells at least, or at, 1, 2, 3, 4, 5, 6, 7, 8, 9, 10, 11, 12, 13, 14, 15, 16, 17, 18, 19, 20 or 21 days post-transplant, compared to transplantation of a number of placental stem cells equivalent to the number of cells in the combined stem cell population or stem cells from a second source equivalent to the number of cells in the combined stem cell population, alone. In another more specific embodiment, said combined stem cell population improves engraftment in an individual in need of stem cells more than 21 days post-transplant.

In a more specific embodiment, said ratio is a ratio in a total number of cells that produces in vitro more colony-forming units than either a number of placental stem cells or stem cells from a second source, equivalent to said total number of cells, alone, under conditions that allow the formation of colony-forming units. In another more specific embodiment, said ratio is the ratio in a plurality of ratios of placental stem cells and stem cells from a second source that, when combined in vitro under conditions that allow the formation of colony-forming units, produces the greatest number of colony-forming units. That is, if X is the number of placental stem cells plus the stem cells from a second source, in such an embodiment, the ratio of placental stem cells to stem cells from a second source produces in vitro more colony-forming units than either X placental stem cells alone, or X stem cells from a second source, alone.

The invention further provides for the assembly of a bank of HLA-characterized placenta-derived stem cells for use in producing combined stem cell populations of the invention. In one embodiment, the invention provides a stem cell bank comprising a plurality of units of placenta-derived stem cells, wherein said placenta-derived stem cells are identified by at least one HLA marker. In a specific embodiment, said placenta-derived stem cells are isolated from placental perfusate. In another specific embodiment, said placenta-derived stem cells are contained within a population of nucleated cells isolated from placental perfusate. In another specific embodiment, said placenta-derived stem cells are CD34$^+$ stem cells. In another specific embodiment, said placenta-derived stem cells are positive for CD73 or CD105, or are bound by antibodies SH2, SH3 or SH4. In another specific embodiment, said stem cell bank additionally comprises a plurality of units of placental blood or umbilical cord blood. In another specific embodiment, at least one unit of said plurality of units of placental blood or umbilical cord blood is identified by an HLA marker shared by one of said plurality of units of placenta-derived stem cells. In another specific embodiment, a majority of units within said plurality of units of placental blood or umbilical cord blood is identified by an HLA marker shared by a majority of units within said plurality of units of placenta-derived stem cells.

3.1 Definitions

As used herein, the term "exsanguinated" or "exsanguination," when used with respect to the placenta, refers to the removal and/or draining of substantially all cord blood from the placenta.

As used herein, "passage," with respect to cell culture, means the aliquoting of a plurality of cells from one culture into a separate container to start a new culture of cells. Typically, passaging comprises the aliquoting of, e.g., $10^4$-$10^5$ cells from one culture in one container into fresh medium in a separate container. Cells are typically passaged when a culture of cells approaches confluency, that is, when a monolayer of adherent cells forms a single layer over the entire area available for growth.

As used herein, the term "perfuse" or "perfusion" refers to the act of passing a fluid through the vasculature of a placenta with a force sufficient to collect a plurality of placental cells. As used herein, the term "placental perfusate" refers to the fluid collected following its passage through a placenta, including cells that have been collected from the placenta during perfusion.

As used herein, the terms "placental blood" and "umbilical cord blood" are equivalent.

As used herein, the terms "placental stem cell" and "placenta-derived stem cell" are equivalent.

As used herein, the term "placental stem cell" refers to a stem cell that is obtained from or derived from a mammalian placenta, or a portion thereof (e.g., amnion, chorion, and the like) regardless of morphology, cell surface markers, etc., but does not encompass a trophoblast. The phrase encompasses a stem cell obtained directly from a placenta, e.g., as part of a population of placental cells in placental perfusate or digested placental tissue (digestate), or a stem cell that is part of a population of placental cells that has been expanded and/or passaged one or more times. The term does not, however, encompass stem cells derived solely from another tissue, e.g., placental blood or umbilical cord blood. The placenta comprises stem cell populations having, and distinguishable from each other by, for example, distinct sets of markers.

As used herein, the term "positive," in reference to a stem cell marker, means that the marker is present in a detectably higher amount, or detectably higher level, than the amount or level of said marker in a reference non-stem cell, e.g., a fibroblast. More generally, a cell is "positive" for a marker when the cell can be differentiated from one or more other cell types on the basis of the presence of that marker in or on the cell.

As used herein, "stem cell from a second source" means any mammalian stem cell (including progenitor cells) from a source other than a mammalian placenta.

As used herein, the term "stem cell" encompasses stem cells and progenitor cells.

As used herein, the term "unit," when applied to cord blood or placental blood, indicates a single collection of blood from a single donor, or the nucleated cells, or the stem cells, obtainable from such a collection. Typically, the volume of blood from a single donor ranges from about 50 to about 150 ml of blood. The term "unit," when applied to placental perfusate, means the volume of perfusion fluid used to collect placental stem and progenitor cells from a single placenta, or the nucleated cells, or the stem cells, obtainable from such a volume of perfusion solution. The volume of placental perfusate in a unit is typically from about 100-500 ml to about 1000 ml.

4. BRIEF DESCRIPTION OF THE FIGURES

FIGS. 1A-1D: Summary of FACS analysis of engrafted human cells in mice bone marrow using CD45 antibodies in two independent experiments. (A): First experiment, CD45+ cells present in bone marrow at 3 weeks for umbilical cord blood cells only (UCB), placental perfusate cells only (PP) or umbilical cord cells combined with placental perfusate cells (UCB+PP). X-axis: numbers of cells per transplantation. (B): First experiment, CD45$^+$ cells at 10 weeks post-transfusion. (C): Second experiment, CD45$^+$ cells in bone marrow at 3 weeks post-transfusion. (D): Second experiment, CD45$^+$ cells in bone marrow at 10 weeks post-transfusion.

Figure 2:
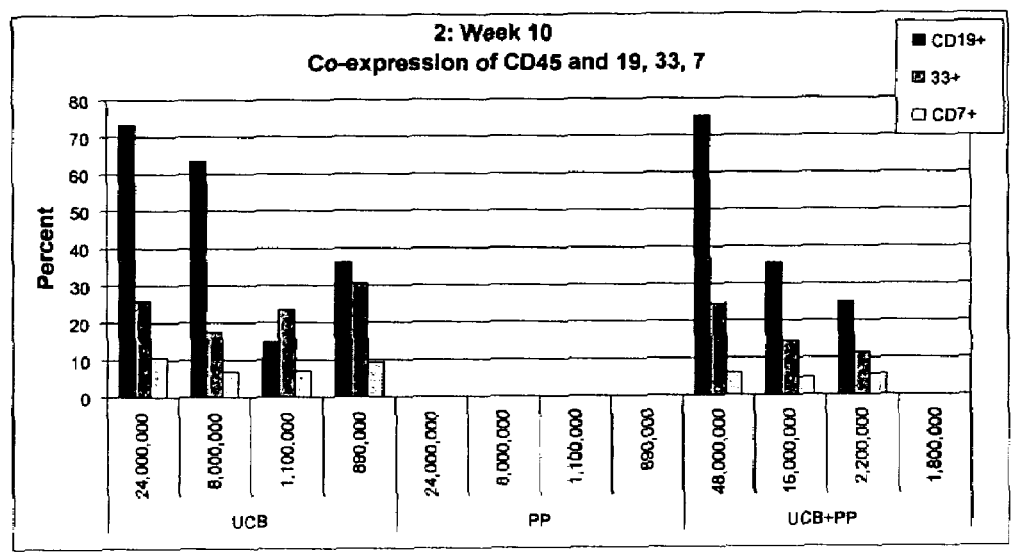

FIG. 2: FACS analysis of engrafted human cells expressing lymphomyeloid cell markers in NOD/SCID mice. Co-expression of CD45$^+$ with CD19 (left bar in each category); CD33 (middle bar); or CD7 (right bar). X-axis: numbers of cells per transplantation. UCB=transplantation of umbilical cord blood cells only; PP=transplantation of placental perfusate cells only. UCB+PP=transplantation of umbilical cord cells combined with placental perfusate cells.

5. DETAILED DESCRIPTION OF THE INVENTION

The present invention provides combinations of (1) placental stem cells, e.g., placental stem cells in human placental perfusate, placental stem cells in placental enzymatic digestate, isolated placental stem and/or progenitor cells, and the like; and (2) stem cells from a second source, in a total number of cells, wherein the placental stem cells and stem cells from the second source are present in the combination in a ratio that produces a greater number of colony-forming units compared to a number of colony-forming units produced by placental stem cells or by stem cells from a second source, equivalent to said total number of cells, alone. The invention further provides combinations of placental stem cells and stem cells from a second source that enhance engraftment in vivo compared to the number of colony-forming units produced by a number of placental stem cells equivalent to the number of cells in said combination, or a number of stem cells from a second source equivalent to the number of cells in said combination, alone. The present invention further provides methods of identifying such ratios, and such combinations, and methods of using the combined stem cell populations.

5.1 Optimizing Combinations of Placental Stem Cells and Stem Cells from a Second Source

5.1.1 In Vitro Assay

The invention provides in vitro co-culture methods for identifying a combination of placental stem cells and stem cells from a second source that has improved engraftment potential as compared to a number of either placental stem cells or stem or progenitor cells from a second source, equivalent to the number of cells in said combination, alone. The in vitro co-culture assay thus identifies ratios of placental stem cells to stem cells from a second source that improve the number of colony-forming units, and engraftment, in a non-cell number-dependent manner.

In one embodiment, for example, the invention provides a method of identifying a ratio of placental stem cells to stem cells from a second source, comprising identifying a ratio of placental stem cells to stem cells from a second source in a total number of cells that, when said placental stem cells and stem cells from a second source are cultured together for a time and under conditions that allow the formation of colony-forming units, produces a greater number of colony-forming units than a number of placental stem cells or stem cells from a second source, equivalent to the number of cells in said total number of cells, alone. In another embodiment, where several ratios are compared, the invention provides a method of identifying a ratio of placental stem cells and stem cells or progenitor cells from a second source in a total number of cells, comprising contacting a population of said placental stem cells in vitro with a population of said stem cells from a second source in a plurality of ratios for a time and under conditions sufficient to allow the formation of colony-forming units, and identifying a ratio within said plurality of ratios that yields the greatest number of colony-forming units. In a specific embodiment, said ratio improves engraftment into a recipient as compared to engraftment by a number of placental stem cells or stem cells from a second source, equivalent to the number of cells in said total number of cells, alone. In more specific embodiments, said combined stem cell population improves engraftment in an individual in need of stem cells for at least 1, 2, 3, 4, 5, 6, 7, 8, 9, 10, 11, 12, 13, 14, 15, 16, 17, 18, 19, 20 or 21 days post-transplant. In another more specific embodiment, said combined stem cell population improves engraftment in an individual in need of stem cells at a time more than 21 days post-transplant.

5.1.1.1 Placenta-Derived Stem Cells

Placenta-derived stem cells useful in the methods and compositions of the invention include, for example, embryonic-like cells, pluripotent cells, multipotent cells, committed progenitor cells, hematopoietic progenitor cells, and mesenchymal-like stem cells from placenta. In one embodiment, the placenta-derive stem cells are contained within, or are derived from, placental perfusate.

Placenta-derived stem cells used in the methods of the invention can be derived from a single placenta, or from a plurality of placentas, and may be obtained by any method. Placenta-derived stem cells can be obtained by, for example, perfusion, as disclosed in U.S. Application Publication Nos. 2002/0123141 and 2003/0032179, the disclosures of each of which are incorporated herein by reference. Such perfusion can be perfusion by the pan method, wherein perfusion liquid is forced through the placental vasculature and perfusion fluid that exudes from the placenta, typically the maternal side, is collected in a pan containing the placenta. Perfusion can also be a closed-circuit perfusion, wherein perfusion fluid is passed through, and collected from, only the fetal vasculature of the placenta. In a specific embodiment, such perfusion can be continuous, that is, perfusion fluid that has been passed through the placenta, and which comprises a plurality of placental cells, is passed through a second time, or a plurality of times, prior to isolation of placental cells.

Placenta-derived stem cells may also be obtained by physical or enzymatic disruption of the placenta using, e.g., proteases and/or other tissue-disruptive enzymes to disrupt the multicellular structure of the placenta. Such proteases may include neutral proteases or metalloproteases, e.g., collagenase, dispase, trypsin, elastase, and the like. Placental stem cells may also be obtained by physical disruption of the placenta using, e.g., mucolytic enzymes, for example, hyaluronidase.

The isolated perfused placenta of the invention provides a source of large quantities of stem cells enriched for $CD34^+$ stem cells, e.g., $CD34^+CD38^-$ stem cells, e.g., $CD34^+$, $CD38^-$, $lin^-$ stem cells, and $CD34^-$ stem cells, e.g., $CD34^-CD38^+$ stem cells. The first collection of blood from the placenta is referred to as cord blood which contains predominantly $CD34^+CD38^+$ hematopoietic progenitor cells. Within the first twenty-four hours of post-partum perfusion, high numbers (e.g., $1 \times 10^5$ to about $2 \times 10^7$) of $CD34^+CD38^-$ hematopoietic progenitor cells may be isolated from the placenta, along with high concentrations of $CD34^-CD38^+$ cells. After about twenty-four hours of perfusion, high numbers (e.g., 1-10 million) of $CD34^-CD38^-$ cells can be isolated from the placenta along with the aforementioned cells. An isolated placenta that has been perfused for twenty-four hours or more provides a source of large quantities of stem cells enriched for $CD34^-CD38^-$ stem cells.

In another embodiment, the combined stem cell populations of the invention comprise $CD34^+$ placental stem cells that are positive for aldehyde dehydrogenase (ALDH). Such cells demonstrate detectable levels of ALDH activity in an ALDH assay. Such assays are known in the art (see, e.g., Bostian and Betts, *Biochem. J.,* 173, 787, (1978)). In a specific embodiment, said ALDH assay uses ALDEFLUOR® (Aldagen, Inc., Ashland, Oreg.) as a marker of aldehyde dehydrogenase activity. Thus, in various embodiments, a combined stem cell population of the invention comprises CD34+ stem cells, where at least about 5%, 10%, 15%, 20%, 25%, 30%, 35%, 40%, 45%, 50%, 55%, 60%, 65%, 70%, 75%, 80%, 85%, 90%, or at least 95% of the CD34$^+$ stem cells are ALDH$^+$.

At least one class of human placental stem cells has characteristics of embryonic stem or germ cells. For example, stem cells of this class are SSEA3$^-$ (stage-specific embryonic antigen 3), SSEA4$^-$, OCT-4$^+$ (a stem cell transcription factor) and ABC-p$^+$ (ATP-binding cassette (ABC) transporter protein), a marker profile exhibited by pluripotent stem cells that have not yet undergone differentiation. Thus, the methods and compositions of the invention can use or comprise non-embryonic, placental stem cells that are, e.g., SSEA3$^-$, SSEA4$^-$, OCT-4$^+$ or ABC-p$^+$. Preferably, the placental stem cells are OCT-4$^+$ABC-p$^+$, and, even more preferably, are SSEA3$^-$SSEA4$^-$OCT-4$^+$ABC-p$^+$. In another embodiment, the invention encompasses the use of placental stem cells positive for at least one of CD10, CD29, CD44, CD54, CD90, CD73 or CD105, or negative for at least one of CD34, CD38, or CD45. In another embodiment, the methods and compositions of the invention can use or comprise placental stem cells having or positive for CD10, CD29, CD44, CD54, CD90, CD73 or CD105, and lacking or negative for CD34, CD38, or CD45. In another embodiment, the methods and compositions of the invention can use or comprise placental stem cells positive for at least one of CD10, CD29, CD44, CD54, CD90, CD73 or CD105, or negative for at least one of CD34, CD38, or CD45. In another embodiment, the invention encompasses the use of placental stem cells having or positive for CD10, CD29, CD44, CD54, CD90, CD73 or CD105, and lacking or negative for CD34, CD38, or CD45.

In one embodiment, placental stem cells used in the methods and compositions of the invention are identified by the presence of the markers CD10, CD29, CD44, CD54, CD90, CD105 (SH2), CD73 (SH3, SH4), OCT-4, and/or ABC-p, and/or the absence of the markers CD34, CD38, CD45, SSEA3, or SSEA4. In a specific embodiment, the placental stem cells are CD10$^+$, CD29$^+$, CD34$^-$, CD38$^-$, CD44$^+$, CD45$^-$, CD54$^+$, CD73$^+$, CD90$^+$, CD105$^+$, SH2$^+$, SH3$^+$, SH4$^+$, SSEA3$^-$, SSEA4$^-$, OCT-4$^+$, and ABC-p$^+$. In another specific embodiment, the placental stem cells are CD200$^+$ and HLA-G$^+$. In this context, "SH2$^+$", "SH3$^+$" and "SH4$^+$" mean that a stem cell is bound by antibody SH2, SH3, or SH4, respectively. In another specific embodiment, the placental stem cells are CD73$^+$, CD105$^+$ and CD200$^+$. In another specific embodiment, the placental stem cells are CD200$^+$ and OCT-4$^+$. In another specific embodiment, the placental stem cells are CD73$^+$, CD105$^+$ and facilitate the formation of embryoid-like bodies in a population of isolated placental cells comprising said stem cells, when said population is cultured under conditions that allow the formation of embryoid-like bodies. In another specific embodiment, the placental stem cells are CD73$^+$, CD105$^+$ and HLA-G$^+$. In another specific embodiment, the placental stem cells are OCT-4$^+$ and facilitate the formation of embryoid-like bodies in a population of isolated placental cells comprising said stem cells, when said population is cultured under conditions that allow the formation of embryoid-like bodies. As used herein, "embryoid-like bodies" refers to three-dimensional clusters of differentiating, and differentiated, cells that emerge from the adherent stem cell layer.

In another embodiment, the human placental stem cells do not express MHC Class 2 antigens.

Populations of placental perfusate-derived stem cells, in one embodiment, comprise trophoblasts.

Cell markers, e.g., stem cell markers and cell surface markers, can be routinely determined according to methods well known in the art, e.g. by flow cytometry or fluorescence-activated cell sorting (FACS) analysis by washing and staining with an anti-cell surface marker antibody labeled with an appropriate fluorophore. For example, to determine the presence of CD34 or CD38, cells may be washed in PBS and then double-stained with anti-CD34 phycoerythrin and anti-CD38 fluorescein isothiocyanate (Becton Dickinson, Mountain View, Calif.). The cells would then be analyzed using a standard flow cytometer. Alternatively, intra-cellular markers can also be examined via standard methodology. Antibody/fluorophore combinations to specific markers include, but are not limited to, fluorescein isothiocyanate (FITC) conjugated monoclonal antibodies against HLA-G (available from Serotec, Raleigh, N.C.), CD10 (available from BD Immunocytometry Systems, San Jose, Calif.), CD44 (available from BD Biosciences Pharmingen, San Jose, Calif.), and CD105 (available from R&D Systems Inc., Minneapolis, Minn.); phycoerythrin (PE) conjugated monoclonal antibodies against CD44, CD200, CD117, and CD13 (BD Biosciences Pharmingen); phycoerythrin-Cy7 (PE Cy7) conjugated monoclonal antibodies against CD33 and CD10 (BD Biosciences Pharmingen); allophycocyanin (APC) conjugated streptavidin and monoclonal antibodies against CD38 (BD Biosciences Pharmingen); and Biotinylated CD90 (BD Biosciences Pharmingen). Other antibody/label combinations that can be used include, but are not limited to, CD133-APC (Miltenyi), KDR-Biotin (CD309, Abcam), CytokeratinK-Fitc (Sigma or Dako), HLA ABC-Fitc (BD), HLA DRDQDP-PE (BD), β-2-microglobulin-PE (BD), CD80-PE (BD) and CD86-APC (BD), CD45-PerCP (peridin chlorophyll protein); CD44-PE; CD19-PE; CD10-F (fluorescein); HLA-G-F and 7-amino-actinomycin-D (7-AAD); HLA-ABC-F; and the like.

Placental stem cells, e.g., placental stem cells contained in placental perfusate, can be used immediately after collection, or can be cultured for a period of time prior to assaying or administration to an individual in a combined stem cell population. For example, in one embodiment, the stem cells can be cultured in medium comprising Notch agonist, e.g., a deletion form of a Notch protein consisting essentially of the intracellular domain of the Notch protein, or a Delta protein. See U.S. 2004/0067583.

5.1.1.2 Stem Cells from a Second Source

The methods and compositions described herein use placental stem cells in combination with stem cells from a second source, that is, stem cells from any source other than a mammalian placenta. Stem cells from a second source can comprise one or more types of stem cells, such as embryonic stem cells, embryonic germ cells, adult stem cells, mesenchymal stem cells, hematopoietic stem cells, non-hematopoietic stem cells, bone marrow-derived stem cells, neural stem cells, cardiac stem cells, ocular stem cells, epithelial stem cells, endothelial stem cells, hepatic stem cells, pulmonary stem cells, muscle stem cells, intestinal stem cells, and the like. Stem cells from a second source can be stem cells isolated from the second, non-placental source, or can be tissue comprising the stem cells. As for the placenta, stem cells can be isolated by perfusion of the organ(s) comprising the stem cells, or by tissue disruption and/or enzymatic digestion of the organ(s) comprising the stem cells. Stem cells from a second source can be, e.g., stem cells derived solely from umbilical cord, or solely from amniotic fluid.

Stem cells from a second source may be obtained by providing a sample of a relevant tissue, and isolating stem cells from the tissue using one or more cell surface markers. For example, hematopoietic stem cells may be obtained from blood (e.g., peripheral blood, placental blood, umbilical cord blood) or from bone marrow by obtaining a sample of blood or bone marrow, isolating mononuclear cells from the blood or bone marrow, and separating $CD34^+$ cells from the isolated mononuclear cells. Such separation may be accomplished by methods routine in the art, e.g. using apherisis, followed by separation using magnetic beads or a column comprising one or more antibodies to the cell surface marker, e.g., CD34 or CD200; fluorescence-activated cell sorting (FACS), and the like. For blood, the stem cells can be provided in a population of total nucleated cells (TNC) from the blood, e.g., total nucleated cells from peripheral blood, placental blood, umbilical cord blood, and the like.

Stem cells from other tissues may be isolated in a similar manner. Mesenchymal stem cells may be isolated from, e.g., bone marrow by isolation of cells positive for CD73, CD105 and/or CD45 (see, e.g., U.S. Pat. No. 6,387,367). Ocular (limbal) stem cells may be obtained from the cornea by obtaining corneal cells and isolating $SSEA-4^+$ cells (see, e.g., U.S. Application Publication No. 2005/0186672). Hepatic stem cells may be obtained from liver, particularly fetal liver, samples, by selecting cells expressing CD14, CD34, CD38, ICAM, CD45, CD117, glycophorin A, connexin 32, osteopontin, bone sialoprotein, collagen I, collagen II, collagen III, collagen IV, or combinations thereof (see, e.g., U.S. Application Publication No. 2005/0148072). Muscle stem cells may be obtained from muscle tissue by selecting $CD34^+$ $CD45^-$ cells that do not express other hematopoietic cell markers (see, e.g., U.S. Application Publication No. 2005/0079606). Cardiac stem cells may be isolated from cardiac tissue by selecting $c-kit^-CD31^+CD38^+$ cells (see, e.g., U.S. Application Publication No. 2004/0126879). Isolation of stem cells may be accomplished using other known characteristics or markers, as well.

In one embodiment, said stem cells from a second source are cord blood stem cells. In specific embodiments, the cord blood stem cells are $CD34^+$ stem cells, e.g., $CD34^+$, $CD38^+$ stem cells, $CD34^+$, $CD38^-$ stem cells, $CD34^+$, $CD38^-$, $lin^-$ stem cells, and the like. In a specific embodiment, the $CD34^+$ stem cells from a second source are $ALDH^+$. Cord blood itself, or stem and/or progenitor cells obtained from cord blood, can be used in the methods of the invention. In a specific embodiment, said cord blood-derived cells comprise hematopoietic stem cells, where the combined stem cell population is to be used for hematopoietic engraftment. The stem cells from a second source may be derived from a single donor, or from a plurality of donors in equal or unequal amounts. Stem cells from a plurality of second (that is, non-placental) sources may be combined with placental stem cells, and used for the methods and compositions of the present invention.

Stem cells from a second source, e.g., hematopoietic stem cells from a second source, can be used immediately after collection, or can be cultured for a period of time prior to assaying or administration to an individual in a combined stem cell population. For example, in one embodiment, the stem cells can be cultured in medium comprising Notch agonist, e.g., a deletion form of a Notch protein consisting essentially of the intracellular domain of the Notch protein, or a Delta protein. See U.S. 2004/0067583

5.1.1.3 Assay Parameters

Once a population of placental stem cells and a population of stem cells from a second source are obtained, the cells can be combined in an in vitro co-culture, or colony-forming, assay to determine if the number of stem cells in a particular combination produces more colony-forming units than a number of placental stem cells or stem cells from a second source, equivalent to the number of cells in said combination, alone. Any such combination of placental stem cells and stem cells from a second source in a ratio that produces more colony forming units than either placental stem cells or stem cells from a second source alone, for equivalent numbers of cells, is identified as a combined stem cell population of the invention.

The identification of a combined stem cell population can use any colony forming unit assay commonly used and known in the art, provided the assay allows for the proliferation and differentiation of stem cells from placenta and from a second source, for example, colony forming assays provided by StemCell Technologies, Inc. Such an assay may use, e.g., MESENCULT™ medium (Stem Cell Technologies, Inc., Vancouver British Columbia). The identification of combined stem cell populations can use cells that are freshly-prepared, or thawed from frozen stocks, or both. Preferably, both the placental stem cells and stem cells from a second source are in suspension when combined for co-culture. Placental stem cells, and stem cells from a second source, may be assessed for viability, proliferation potential, and longevity using standard techniques known in the art, such as trypan blue exclusion assay, fluorescein diacetate uptake assay, propidium iodide uptake assay (to assess viability); and thymidine uptake assay, MTT (3-(4,5-dimethylthiazol-2-yl)-2,5-diphenyltetrazolium bromide) cell proliferation assay (to assess proliferation). Longevity may be determined by methods well known in the art, such as by determining the maximum number of population doublings in an extended culture.

In one embodiment of the in vitro method, a colony forming unit assay using placental stem cells and cord blood-derived stem cells is performed as follows. Fresh or thawed HLA/donor matched placental perfusate and cord blood units are obtained, and the number of total nucleated cells in each is determined with a hemacytometer. Where thawed units are used, cord blood samples can be hetastarch-separated, and placental perfusate units are preferably Ficoll-separated. Small samples of nucleated cells from each source are seeded together in suspension in two or more ratios in a co-culture, and expanded. The co-culture can be performed in, e.g., triplicate for one or more ratios of placental stem cells to stem cells from a second source, in, for example, 35 mm dishes in an appropriate cell culture medium (e.g., RPMI 1640 medium supplemented with 2-10% fetal calf serum and, optionally, 1% Stemspan cytokine cocktail; Methocult $GF^+$ H4435 medium, etc.). Hematopoietic stem cells may be expanded in culture medium comprising GM-CSF, IL-3, IL-6, SCF and flt-3 ligand.

The container used for the co-culture assay is preferably appropriate for tissue culture of stem cells. For example, co-cultures may be performed in glass or plastic Petri dishes, 16-well plates, 32-well plates, 96-well plates, 128-well plates, and the like. Typically, the total number of nucleated cells from each source in each co-culture varies from $1 \times 10^4$ to $1 \times 10^6$. Cells may also be co-cultured in a micropatterned configuration. See U.S. Pat. No. 6,221,663.

When determining the ratio of placental stem cells to stem cells from a second source in a cell population that comprises a number of placental stem cells and stem cells from a second source, the preferred ratio is any ratio that generates more colony forming units than that generated by said number of placental stem cells or said number of stem cells from a second source under the same conditions. More preferably, the ratio is a ratio that generates a higher number of colony-forming units than all other ratios tested. Statistical significance between ratios tested is desirable, but not necessary. The higher number of colony-forming units may be attributable to, or be derived from, both placental stem cells and stem cells from a second source; from predominantly or only the placental stem cells; or predominantly or only the stem cells from a second source.

The combined stem cell population is cultured for a time sufficient for colony forming units to form, typically 10-20 days. Cell culture during expansion follows standard protocols known in the art of stem or progenitor cell culture, and includes, for example, daily or semi-daily changes of medium; culture at about 37° C. at 5% $CO_2$ in a humidified incubator, and the like. After 10-20 days, the number and morphology of colony forming units in the co-culture is determined (e.g., for hematopoietic stem cells, the number of CFU-GM, CFU-L, CFU-M, CFU-G, CFU-DC, CFU-GEMM, CFU-E).

In a specific example of the co-culture assay, nucleated cells from placenta perfusate, and nucleated cells from cord blood are combined a ratio of 1:1, 1:3 and 3:1 (where 1 equals, e.g., $1 \times 10^5$ cells) in Methocult $GF^+$ H4435 medium. The co-culture is then expanded in tissue culture for about 14 days. The morphology of the co-cultured cells, and the number of colony forming units, is determined. The ratio of the nucleated cell samples from the two sources that provides the highest number of colony-forming units is designated an optimum ratio, and the two units, or stem and/or progenitor cells from one or both of the units, are combined in the optimum ratio for administration to a recipient in need of a stem cell transplant. Such an optimum ratio provides superior engraftment in vivo over the administration of either unit, or stem and/or progenitor cells from either unit, alone, where equivalent numbers of cells are administered.

The placental stem cells and stem cells from a second source are contacted with each other during the co-culturing, either directly or indirectly. At a minimum, this comprises contacting one of the types of stem cells with culture medium in which the other type of stem cell has cultured for a period of time, e.g., contacting one of the types of stem cells with medium that has been conditioned by the other type of stem cell. For example, the placental stem cells, and stem cells from a second source may be cultured together in the same physical space during culture for colony-forming unit formation, e.g., in the same culture dish or well in a multi-well plate. The placental stem cells and stem cells from a second source may also be contacted with each other by culturing in separate physical spaces, but in common culture medium (e.g., separated by a membrane, or in two wells of a multiwell plate wherein culture medium may move actively or passively between the wells, but cells cannot mix). In another embodiment, placental stem cells and stem cells from a second source may be cultured in separate physical spaces with no common culture medium, and the stem cells brought into contact with each other by an exchange of part or all of the culture medium from one stem cell culture with that of the other. In another embodiment, the cells in the co-culture are cultured in a manner that physically separates the cells, but allows biomolecules to diffuse between the two cultures. See, e.g., U.S. Pat. No. 5,665,596 "Device for Cell Co-culture and Method for Its Use in Culturing Cells". Where the stem cell cultures are separate, the number of colony-forming units in the separate, paired cultures is totaled for each replicate of ratio, and an optimum ratio determined, as above.

In another embodiment of the method, a bioactive molecule is added to the placental stem cells and stem cells from a second source during the assay, and a ratio of placental stem cells to stem cells from a second source is identified that, for a total number of cells, results in more colony-forming units, or enhanced engraftment, compared to a number of placental stem cells or stem cells from a second source, equivalent to said total number of cells in said combination, alone. Such a bioactive molecule may be a small organic molecule of less than 50 kDa, 30 kDa, 20 kDa, 10 kDa, 5 kDa, 3 kDa, 2 kDa, 1 kDa, 500 Da, 300 Da, 200 Da, 100 Da or smaller. In a specific embodiment, said small organic molecule is synthetic or non-natural, that is, not derived from a natural source. In another specific embodiment, said bioactive molecule is a cytokine or growth factor. Bioactive molecules that can be added to the co-culture include differentiation-inducing agents such as, but are not limited to, $Ca^{2+}$, EGF, α-FGF, β-FGF, PDGF, keratinocyte growth factor (KGF), TGF-β, cytokines (e.g., IL-1α, IL-1β, IFN-γ, TFN), retinoic acid, transferrin, hormones (e.g., androgen, estrogen, insulin, prolactin, triiodothyronine, hydrocortisone, dexamethasone), sodium butyrate, TPA, DMSO, NMF, DMF, matrix elements (e.g., collagen, laminin, heparan sulfate, MATRIGEL™), or combinations thereof. Bioactive molecules that are differentiation suppressants may also be added, such as, but not limited to, human Delta-1 and human Serrate-1 polypeptides (see, Sakano et al., U.S. Pat. No. 6,337,387 entitled "Differentiation-suppressive polypeptide", issued Jan. 8, 2002), leukemia inhibitory factor (LIF), and stem cell factor.

Where a bioactive molecule is added to the co-culture, the co-culture assay may be used to identify a positive effector of engraftment. In one embodiment, therefore, the invention provides a method of identifying a bioactive molecule that is a positive effector of engraftment comprising contacting a combined stem cell population with said bioactive molecule, wherein said bioactive molecule is identified as a positive effector of engraftment if engraftment by said combined stem cell population is detectably enhanced compared to engraftment by a combined stem cell population not contacted with said bioactive molecule. In another embodiment, the invention provides a method of identifying a positive effector of engraftment comprising combining placental stem cells and stem cells from a second source in vitro in one or more ratios in the presence of said bioactive molecule; culturing said placental stem cells and stem cells from a second source for a time sufficient for colony forming units to form; determining the number of colony-forming units for each of said one or more ratios; and determining, for at least one of said one or more ratios, whether the number of colony forming units in the presence of said bioactive molecule is greater than the number of colony forming units in the absence of said bioactive molecule, and, if so, identifying said bioactive molecule as a positive effector of engraftment.

The in vitro assay may be performed on any placental stem cell population and stem cell population from a second source to determine an optimum ratio for engraftment. In this aspect, the in vitro co-culture assay can be used as a standard, routine procedure to characterize stem cell populations prior to transplantation.

5.1.2 In Vivo Assay

The results of the above in vitro assay may be confirmed using an in vivo engraftment assay. The in vivo assay may also be performed in the absence of the in vitro assay to determine an optimum ratio of placental stem cells, and stem cells from a second source, to maximize engraftment.

In one embodiment of the in vivo assay, placental stem cells and stem cells from a second source are transplanted into a plurality of model animals and given sufficient time to engraft (typically 6-10 weeks). The animals are subsequently sacrificed, and the degree of engraftment in each animal is determined for at least one tissue. Thus, in one embodiment, the invention provides a method of identifying a ratio of placental stem cells and stem cells or progenitor cells from a second source for engraftment into a recipient, comprising identifying a ratio of placental stem cells to stem cells from a second source in a total number of cells that, when transplanted into an animal, results in enhanced engraftment compared to transplantation of a number of placental stem cells or stem cells from a second source, equivalent to the number of cells in said total number of cells, alone. In another embodiment, said identifying a ratio of placental stem cells to stem cells from a second source comprises transplanting a number of placental stem cells and stem cells from a second source in a plurality of animals, in a plurality of ratios; determining the number of engrafted cells in at least one tissue of said animals for each of said plurality of ratios; and identifying the ratio in said plurality of ratios that yields the highest number of engrafted cells.

As in the in vitro assay, the placental stem cells can be placental stem cells obtained by any means or present in any usable form. For example, the placental stem cells may be contained in placental perfusate, or may be contained within isolated total nucleated cells from the placental perfusate, or may be a population of stem cells isolated from the total nucleated cells, or may be placental stem cells contained within enzyme-digested placental tissue, or may be placental stem cells isolated from enzyme-digested placental tissue, or may be placental stem cells that have been expanded and/or passaged in culture, etc.

Any standard model animal may be used in the in vivo co-culture assay. Preferably, the model animal is one in which engraftment of xenografts may be readily accomplished. Small mammals such as standard laboratory rodents such as mice and rats are preferred because they require fewer administered stem cells to show engraftment. It is highly preferable that the model animal be immune-compromised. Animal models that may be used in the in vivo assay include, but are not limited to, NOD/SCID (non-obese diabetic/severe combined immune deficiency) mice (see Hogan et al., *Blood* 90(1):85-96 (1997)); beige/nude/x-linked immunodeficiency (BNX) mice (see, e.g., Kamal-Reid et al., *Science* 242:1706 (1988)); SCID mice (see, e.g., Kamal-Reid et al., *Science* 246:1597 (1989). Engraftment may be accomplished in other animal models, such as sheep fetuses (see, e.g., Shimizu et al., *Blood* 91(10):3688-3692 (1998); Zanjani et al., *Int'l J. Hematol* 63(3): 179-182 (1996)).

The determination of the number of engrafted cells in tissues from the recipient animal may be accomplished by any means known in the art. For example, detection of engrafted cells may be accomplished by detection of engrafted cell-specific nucleic acids, e.g., by the polymerase chain reaction, or by detection of proteins specific for engrafted cells, e.g., by immunohistochemistry. Identification of engraftment in vivo may be determined through the use of a sample, e.g., biopsy specimen, taken at one or more locations on, and at one or more post-transplantation times from, a recipient.

In one embodiment, demonstration of engraftment of placental stem cells and/or cord blood-derived stem cells can be accomplished by taking a biopsy (e.g., bone marrow aspirate or peripheral blood sample) and performing PCR to determine whether any non-recipient genetic markers are present, which would indicate engraftment. In another embodiment, identification of engrafted cells is accomplished by selection of one or more antibodies that recognize markers expressed by the engrafted cells. In a specific embodiment, the engrafted cells are human, and the one or more antibodies specifically recognize one or more human cell markers. Antibodies can be used to detect the markers by any art-accepted method, e.g., immunohistochemical methods. For example, determination of the presence of a cell surface marker can comprise sacrifice of a non-human host animal, obtaining a desired tissue, fixing and embedding the tissue in paraffin or a similar matrix; thin sectioning the tissue, optionally followed by staining; and contacting the tissue with one or more antibodies that recognize the marker. In the same manner, one may use antibodies that recognize markers expressed by cells into which the engrafted stem cells can differentiate. For example, placental stem cells or cord blood-derived stem cells differentiate into cells that express CD45 and vimentin; thus, antibodies to CD45 and vimentin may be used to determine the number of engrafting, and differentiating, stem cells. Antibodies that recognize, e.g., human cell surface markers in preference to host cell markers, e.g., mouse cell surface markers, are well-known in the art.

In a non-limiting example of the in vivo method, a plurality of model animals, e.g., a plurality of mice of the species *Mus musculus*, are transplanted with human placental stem cells and, e.g., human nucleated cells isolated from cord blood, including hematopoietic stem cells, in a plurality of ratios. After several days to several weeks (i.e., sufficient time to allow engraftment), the host animals are sacrificed, and tissues (e.g., spleen, lung, etc.) are examined to determine the approximate number of human cells that have engrafted, as evidenced by the number of cells staining for CD45 and/or vimentin. CD45 is a marker specific for leukocytes, including T- and B-lymphocytes, granulocytes, monocytes and macrophages. Certain CD45 antibodies, such as clone T29/33 (BioDesign, Saco, Me.), do not cross-react with mouse antigens. Vimentin is a marker for mesenchymal cells, such as fibroblasts, smooth muscle cells, lipocytes, Schwann cells, vascular endothelial cells, and the like. Certain vimentin antibodies, such as clone V9 (BioDesign, Saco, Me.), do not cross-react with mouse antigens. Staining with antibodies to these two markers, therefore, can establish generally the extent of engraftment of placental stem cells, and stem cells from a second source, in a variety of tissues. This example is not limiting; different antibodies may be used to determine the extent of engraftment of other cell types. In a long-term engraftment model, bone marrow cells isolated from a primary engrafted animal, e.g., a mouse, can be transplanted into a second engraftment model animal. Assays for secondary engraftment are as listed above and include methods well known to those of skill in the art.

5.2 Combined Stem Cell Populations

The invention further provides combined stem cell compositions comprising placental stem cells, e.g., cells from placental perfusate, e.g., nucleated cells from placental perfusate, comprising placental stem cells and stem cells from a second source that, for a particular number of cells, results in a greater number of colony-forming units in a colony-forming unit assay, or enhanced engraftment in a transplant recipient, than the number of either placental stem cells or stem cells from a second source, alone. Combined stem cell populations identified by the above methods represent engraftment-enhanced combinations of stem cells based on the characteristics of the stem cell sources, that is, the number of engraftable cells contained in, e.g., a unit of placenta perfusate, a unit of cord blood, etc.

Thus, in one embodiment, the invention encompasses a combined stem cell composition comprising a number of placental stem cells and stem cells from a second source in a ratio, wherein the stem cells from the composition show improved engraftment compared to a number of either the placental stem cells or the stem cells from a second source, equivalent to the number of cells in said composition, alone. In a specific embodiment, the ratio is identified by combining placental stem cells and stem cells from a second source in vitro in a plurality of ratios for a time and under conditions sufficient to allow the formation of colony-forming units; and identifying a ratio in said plurality of ratios that yields the highest number of colony forming units. In a more specific embodiment, said stem or progenitor cells from a second source are cord blood stem or progenitor cells, bone marrow stem or progenitor cells, hematopoietic stem or progenitor cells, or mesenchymal stem or progenitor cells. In another more specific embodiment, said stem cells or progenitor cells from a second source are hematopoietic progenitor cells. In an even more specific embodiment, said hematopoietic stem cells are cord blood hematopoietic stem cells. In another even more specific embodiment, said hematopoietic cells are $CD34^+$ cells.

In another more specific embodiment, said placental stem cells comprise $CD34^+$ cells, for example, $CD34^+CD38^+$ cells and/or $CD34^+CD38^-$ cells. In a specific embodiment, said $CD34^+CD38^-$ cells comprise $CD34^+CD38^-lin^-$ stem cells. In another specific embodiment, said CD34+ placental stem cells comprise cells that are ALDH+, that is, $CD34^+, ALDH^+$ placental stem cells.

In another more specific embodiment, said placental stem cells are $OCT-4^+$ or $ABC-p^+$. In another more specific embodiment, said placental stem cells comprise cells that are $OCT4^+ABC-p^+$. In another more specific embodiment, said placental stem cells comprise cells that are $CD34^+$ and cells that are $OCT4^+ABC-p^+$. In another more specific embodiment, said placental stem cells are contained within placental perfusate substantially lacking red blood cells and cellular debris. In another more specific embodiment, said composition comprises placental stem cells isolated from placental perfusate.

In another embodiment, placental stem cells comprise cells that express one or more of markers CD10, CD29, CD44, CD54, CD90, CD73 or CD105, and lack one or more of markers CD34, CD38, CD45, SSEA3 and SSEA4. In another embodiment, placental stem cells comprise cells that are positive for CD10, CD29, CD44, CD54, CD90, CD73 or CD105, and negative for CD34, CD38, CD45, SSEA3 and SSEA4. In another embodiment, placental stem cells comprise cells that comprise one or more of markers CD10, CD29, CD44, CD54, CD90, CD73 and CD105, and lack one or more of markers CD34, CD38, CD45, SSEA3 and SSEA4. In another embodiment, placental stem cells comprise cells that are positive for CD10, CD29, CD44, CD54, CD90, CD73 and CD105, and negative for CD34, CD38, CD45, SSEA3 and SSEA4. In another embodiment, said placental stem cells comprise $CD34^-$ cells. In a specific embodiment, said placental stem cells are $CD34^-CD38^-$ placental stem cells. In another embodiment, said placental stem cells comprise cells that are positive for at least one of CD10, CD29, CD33, CD44, CD73, CD105, CD117, and CD133, and negative for at least one of CD34 or CD45. In another embodiment, said placental stem cells comprise cells that are positive for CD10, CD29, CD33, CD44, CD73, CD105, CD117, and CD133, and negative for CD34 or CD45. In a more specific embodiment, said placental stem cells comprise cells that are $HLA-ABC^+$. In a more specific embodiment, said placental stem cells comprise cells that are $HLA-ABC^-$. In a more specific embodiment, said placental stem cells comprise cells that are $HLA-DR^+$. In a more specific embodiment, said placental stem cells comprise cells that are $HLA-DR^-$. In another specific embodiment, said placental stem cells comprise cells that are $CD200^+$ or $HLA-G^+$. In another specific embodiment, the placental stem cells comprise cells that are $CD200^+$ and $HLA-G^+$. In another specific embodiment, the placental stem cells comprise cells that are $CD73^+, CD105^+$ and $CD200^+$. In another specific embodiment, the placental stem cells comprise cells that are $CD200^+$ and $OCT-4^+$. In another specific embodiment, the placental stem cells comprise cells that are $CD73^+, CD105^+$ and facilitate the formation of embryoid-like bodies in a population of isolated placental cells comprising said stem cells, when said population is cultured under conditions that allow the formation of embryoid-like bodies. In another specific embodiment, the placental stem cells comprise cells that are $CD73^+, CD105^+$ and $HLA-G^+$. In another specific embodiment, the placental stem cells comprise cells that are $OCT-4^+$ and facilitate the formation of embryoid-like bodies in a population of isolated placental cells comprising said stem cells, when said population is cultured under conditions that allow the formation of embryoid-like bodies.

In another embodiment, said stem cells from a second source are stem cells derived from cord blood.

In the combined stem cell populations of the invention, the placental stem cells and the stem cells from a second source may be identically-HLA-matched, that is, they may be derived from the same individual. In another embodiment, the placental stem cells and the stem cells from a second source may be HLA-mismatched, that is, they may be derived from different individuals. For combined stem cell populations comprising cord blood or cord blood-derived stem cells, the combination may also comprise stem cells that are either HLA-matched, partially HLA-matched, or HLA-mismatched to an intended recipient. For combined stem cell populations comprising non-cord blood stem cells, it is preferred that at least the stem cells from a second source be HLA-matched or partially HLA-matched to the intended recipient.

In various embodiments, the ratio of placental stem cells to stem cells from a second source can be about 100,000,000:1, 50,000,000:1, 20,000,000:1, 10,000,000:1, 5,000,000:1, 2,000,000:1, 1,000,000:1, 500,000:1, 200,000:1, 100,000:1, 50,000:1, 20,000:1, 10,000:1, 5,000:1, 2,000:1, 1,000:1, 500:1, 200:1, 100:1, 50:1, 20:1, 10:1, 5:1, 2:1, 1:1; 1:2; 1:5; 1:10; 1:100; 1:200; 1:500; 1:1,000; 1:2,000; 1:5,000; 1:10,000; 1:20,000; 1:50,000; 1:100,000; 1:500,000; 1:1,000,000; 1:2,000,000; 1:5,000,000; 1:10,000,000; 1:20,000,000; 1:50,000,000; or about 1:100,000,000, comparing numbers of total nucleated cells in each population, or comparing total numbers of stem cells in each population. In a preferred embodiment, the ratio of placental stem cells to stem cells from a second source can be about 1:10 to about 10:1. In other preferred embodiments, the ratio of placental stem cells to stem cells from a second source can be about 3:1 to about 1:3.

The combined stem cell populations of the invention can comprise a therapeutically-effective amount of placental stem cells, stem cells from a second source, or both. The combined stem cell populations of the invention, and pharmaceutical compositions comprising a combined stem cell population, can comprise at least $1 \times 10^4$, $5 \times 10^4$, $1 \times 10^5$, $5 \times 10^5$, $1 \times 10^6$, $5 \times 10^6$, $1 \times 10^7$, $5 \times 10^7$, $1 \times 10^8$, $5 \times 10^8$, $1 \times 10^9$, $5 \times 10^9$, $1 \times 10^{10}$, $5 \times 10^{10}$ or $1 \times 10^{11}$ placental stem cells, stem cells from a second source, or both, or no more than $1 \times 10^4$, $5 \times 10^4$, $1 \times 10^5$, $5 \times 10^5$, $1 \times 10^6$, $5 \times 10^6$, $1 \times 10^7$, $5 \times 10^7$, $1 \times 10^8$, $5 \times 10^8$, $1 \times 10^9$, $5 \times 10^9$, $1 \times 10^{10}$, $5 \times 10^{10}$ or $1 \times 10^{11}$ placental stem cells, stem cells from a second source, or both.

In other embodiments, said combined stem cell population improves engraftment in an individual in need of stem cells at least, or at, 1, 2, 3, 4, 5, 6, 7, 8, 9, 10, 11, 12, 13, 14, 15, 16, 17, 18, 19, 20 or 21 days post-transplant. In another more specific embodiment, said combined stem cell population improves engraftment in an individual in need of stem cells at least, or at, more than 21 days post-transplant. In specific embodiments, said combined stem cell population improves engraftment in an individual in need of stem cells at least, or at, more than 25, 30, 35, 40, 45, 50, 55 weeks, or 1 year or longer post-transplant.

The combined stem cell populations of the invention can be preserved, for example, cryopreserved for later use. Methods for cryopreservation of cells, such as stem cells, are well known in the art, for example, cryopreservation using the methods of Boyse et al. (U.S. Pat. No. 5,192,553, issued Mar. 9, 1993) or Hu et al. (WO 00/73421, published Dec. 7, 2000). Placenta-derived stem cells, and stem cells from a second source, which make up a combined stem cell population, can be combined prior to cryopreservation, or can be cryopreserved separately, and combined in the appropriate ratio upon thawing, e.g., within hours of use.

The combined stem cell populations of the invention can be prepared in a form that is easily administrable to an individual. For example, a combined stem cell population can be contained within a container suitable for medical use. Such a container can be, for example, a sterile plastic bag, flask, jar, or other container from which the combined stem cell population can be easily dispensed. Preferably, the container is a container that allows, or facilitates, intravenous administration of a combined stem cell population. The container, e.g., bag, can hold the placenta-derived stem cells and stem cells from a second source together, e.g., as a mixed cell population, or can hold the two stem cell populations separately. In the latter embodiment, the bag preferably comprises multiple lumens or compartments that are interconnected to allow mixing of the placenta-derived stem cells and stem cells from a second source prior to, or during, administration. The container is preferably one that allows for cryopreservation of the combined stem cell population. The combined stem cell population in said container can comprise placenta-derived stem cells, stem cells from a second source, or both, that have been passaged at least, or at most, 1, 2, 3, 4, 5, 6, 7, 8, 9, 10, 11, 12, 13, 14, 15, 16, 17, 18, 19, 20 times, or 25, 30, 35, 40 or more times.

The invention also provides for combined stem cell populations that comprise, e.g., that are stored or maintained as, separate stem cell populations, e.g., a population of placenta-derived stem cells and a population of stem cells from a second source, in combination with information on combining the two populations in an appropriate ratio prior to use, e.g., prior to administration to an individual in need of stem cells. In this embodiment, a combined stem cell population would comprise a population of placenta-derived stem cells in a first container, a population of stem cells from a second source in a second container, and instructions for combining the two populations either before or during administration to an individual in need of stem cells.

Thus, in one embodiment, the invention provides a composition comprising a combined stem cell population in a container, wherein said combined stem cell population comprises placenta-derived stem cells and stem cells from a second source. In a specific embodiment, the container is a bag, flask, or jar. In a more specific embodiment, said placenta-derived stem cells and said stem cells from a second source are contained together in said bag. In another more specific embodiment, said placenta-derived stem cells and said stem cells from a second source are contained separately within said bag. In another specific embodiment, the composition comprises one or more compounds that facilitate cryopreservation of the combined stem cell population. In another specific embodiment, said combined stem cell population is contained within a physiologically-acceptable aqueous solution. In a more specific embodiment, said physiologically-acceptable aqueous solution is a 0.9% NaCl solution. In another more specific embodiment, said bag is a sterile plastic bag. In a more specific embodiment, said bag allows or facilitates intravenous administration of said combined stem cell population. In another specific embodiment, said combined stem cell population comprises placental cells that are HLA-matched to said stem cells from a second source. In another specific embodiment, said combined stem cell population comprises placental cells that are at least partially HLA-mismatched to said stem cells from a second source. In another specific embodiment, said placenta-derived stem cells are derived from a plurality of donors. In another specific embodiment, said stem cells from a second source are derived from a plurality of donors.

Combined stem cell populations can be cultured for a period of time prior to administration to an individual. For example, in one embodiment, the stem cells in a combined stem cell population can be cultured in medium comprising Notch agonist, e.g., a deletion form of a Notch protein consisting essentially of the intracellular domain of the Notch protein, or a Delta protein. See U.S. 2004/0067583

5.3 Pharmaceutical Compositions

The present invention encompasses pharmaceutical compositions that comprise combined stem cell populations of the invention, and a pharmaceutically-acceptable carrier.

In accordance with this embodiment, the combined stem cell populations of the invention may be formulated as an injectable (e.g., WO 96/39101, incorporated herein by reference in its entirety). In another embodiment, the combined stem cell populations of the present invention may be formulated using polymerizable or cross linking hydrogels as described, e.g., in U.S. Pat. Nos. 5,709,854; 5,516,532; 5,654,381.

In another embodiment, the invention provides for the maintenance of each stem cell population of the combined stem cell populations, prior to administration to an individual, as separate pharmaceutical compositions to be administered sequentially or jointly to create the combined stem cell population in vivo. Each component may be stored and/or used in a separate container, e.g., one bag (e.g., blood storage bag from Baxter, Becton-Dickinson, Medcep, National Hospital Products, Terumo, etc.) or separate syringe, which contains a single type of cell or cell population. In a specific embodiment, cord blood, or cord blood-derived nucleated or stem cells, are contained in one bag, and placental perfusate, or placental stem cells from placental perfusate, are contained in a second bag.

A population of placental stem cells can be enriched. In a specific embodiment, a population of cells comprising placental stem cells is enriched by removal of red blood cells and/or granulocytes according to standard methods, so that the remaining population of nucleated cells is enriched for placental stem cells relative to other cell types in placental perfusate. Such an enriched population of placental stem cells may be used unfrozen, or may be frozen for later use. If the population of cells is to be frozen, a standard cryopreservative (e.g., DMSO, glycerol, EPILIFE™ Cell Freezing Medium (Cascade Biologics)) is added to the enriched population of cells before it is frozen.

The pharmaceutical compositions of the invention may comprise one or more agents that induce cell differentiation. In certain embodiments, an agent that induces differentiation includes, but is not limited to, $Ca^{2+}$, EGF, $\alpha$-FGF, $\beta$-FGF, PDGF, keratinocyte growth factor (KGF), TGF-$\beta$, cytokines (e.g., IL-1$\alpha$, IL-1$\beta$, IFN-$\gamma$, TFN), retinoic acid, transferrin, hormones (e.g., androgen, estrogen, insulin, prolactin, triiodothyroxine, hydrocortisone, dexamethasone), sodium butyrate, TPA, DMSO, NMF, DMF, matrix elements (e.g., collagen, laminin, heparan sulfate, MATRIGEL™), or combinations thereof.

In another embodiment, the pharmaceutical composition of the invention may comprise one or more agents that suppress cellular differentiation. In certain embodiments, an agent that suppresses differentiation includes, but is not limited to, human Delta-1 and human Serrate-1 polypeptides (see, Sakano et al., U.S. Pat. No. 6,337,387), leukemia inhibitory factor (LIF), stem cell factor, or combinations thereof.

The pharmaceutical compositions of the present invention may be treated prior to administration to an individual with a compound that modulates the activity of TNF-α. Such compounds are disclosed in detail in, e.g., U.S. Application Publication No. 2003/0235909, which disclosure is incorporated herein in its entirety. Preferred compounds are referred to as IMiDs (immunomodulatory compounds) and SelCIDs (Selective Cytokine Inhibitory Drugs), and particularly preferred compounds are available under the trade names ACTIMID™, REVIMID™ and REVLIMID™.

5.4 Methods of Transplanting Stem Cells
5.4.1 Transplantation Methods

The above method of identifying combined stem cell populations (see Section 5.1) may be performed on paired units of, for example, placental perfusate or placental stem cells, and stem cells from a second source, e.g., cord blood, cord blood stem cells, and the like, to produce combined stem cell populations for the treatment of an individual in need of stem cells. In one embodiment, the individual is contacted with one or more combined stem cell populations. In a specific embodiment, said contacting is the introduction, e.g., transplantation, of said combined stem cell population into said individual. Thus, the method of producing combined stem cell populations may be performed as a first step in a procedure for introducing stem cells into any individual needing stem cells. Such a procedure can comprise use of pharmaceutical compositions comprising the combined stem cell populations, as described above.

In a specific embodiment, a population of placental stem cells of the invention is combined with a population of stem cells from a second source prior to administration to an individual in need thereof in a ratio that provides improved or enhanced engraftment over a number of said placental stem cells or said stem cells from a second source, equivalent to said total number of cells, alone. In another specific embodiment, a population of placental stem cells of the invention is combined with a population of stem cells from a second source during, or simultaneously with, administration to a patient in need thereof, in an optimum ratio, wherein said ratio is identified by identifying a ratio of placental stem cells to stem cells from a second source, in a plurality of ratios, that yields the highest number of said colony-forming units when said placental stem cells and stem cells from a second source are cultured for a time and under conditions sufficient to allow the formation of colony-forming units. In another specific embodiment, a population of placental stem cells of the invention and a population of umbilical cord blood cells are administered sequentially to a patient in need thereof to a final optimum ratio. In one embodiment, the population of placental stem cells is administered first and the population of stem cells from a second source is administered second. In another embodiment, the population of stem cells from a second source is administered first and the population of placental stem cells is administered second.

In a specific embodiment, said combined stem cell population is contained within one bag or container. In another embodiment, the invention provides for use in transplantation of a population of placental stem cells, and stem cells from a second source, that are contained within separate bags or containers. In certain embodiments, stem cell populations contained in two bags may be mixed prior, in particular immediately prior, to or at the time of administration to a patient in need thereof. In other embodiments, the contents of each bag may be administered separately to a patient, wherein two cell populations are used adjunctively in vivo.

Combined populations of placental stem cells, and stem cells from a second source, e.g., cord blood-derived stem or progenitor cells, or cord blood, including banked or cryopreserved cord blood may be mixed, prior to transplantation, by any medically-acceptable means. In one embodiment, the two populations are physically mixed. In another embodiment of the method, said placental stem cells and stem cells from a second source are mixed immediately prior to (i.e., within 1, 2, 3, 4, 5, 7, 10 minutes of) administration to said individual. In another embodiment, said placental stem cells and stem cells from a second source are mixed at a point in time more than five minutes prior to administration to said individual. In another embodiment of the method, the placental stem cells, and/or stem cells from a second source, are cryopreserved and thawed prior to administration to said individual. In another embodiment, said placental stem cells and stem cells from a second source are mixed to form a combined stem cell population at a point in time more than 1, 2, 3, 4, 5, 6, 7, 8, 9, 10, 11, 12, 13, 14, 15, 16, 17, 18, 19, 20, 21, 22, 23, or 24 hours prior to administration to said individual, wherein either or both of said placental stem cells and stem cells from a second source have been cryopreserved and thawed prior to said administration. In another embodiment, the combined stem cell populations may be administered more than once.

In another embodiment, the stem cells contained within the combined stem cell population are preconditioned prior to transplantation. In a preferred embodiment, preconditioning comprises storing the cells in a gas-permeable container generally for a period of time at about −5° C. to about 23° C., about 0° C. to about 10° C., or preferably about 4° C. to about 5° C. The cells may be stored between 18 hours and 21 days, between 48 hours and 10 days, preferably between 3-5 days. The cells may be cryopreserved prior to preconditioning or, may be preconditioned immediately prior to administration.

Once an appropriate ratio of placental stem cells to stem cells from a second source is established, either or both of the placental stem cells, or stem cells from a second source, may be differentiated prior to introduction to an individual in need of stem cells. For example, for introduction for the purpose of hematopoietic engraftment, the stem cells may be differentiated to cells in the hematopoietic lineage. The combination of stem cells and differentiated cells, or combination of cells differentiated from both sources of stem cells, is encompassed within the term "combined stem cell population." Thus, the invention provides a method of introducing stem cells into an individual comprising determining a ratio of placental stem cells and stem cells from a second source in a total number of cells, wherein the ratio improves engraftment as compared to introduction of a number of placental stem cells or stem cells from a second source, equivalent to said total number of cells, alone; differentiating one or both of said placental stem cells or stem cells from a second source into cells of another cell type; and introducing said stem cells and/or differentiated cells to an individual. In certain embodiments of the invention, the method of transplantation of combined stem cell populations comprises (a) induction of differentiation of placental stem cells, (b) mixing the placental stem cells with a population of stem cells from a second source, e.g., cord blood stem cells, to form a combined cell population, and (c) administration of the combined cell population to an individual in need thereof. In another embodiment the method of transplantation comprises (a) induction of differentiation of stem cells from a second source; (b) mixing the differentiated cells with placental stem cells to form a combined cell population; and (c) administration of the combined cell population to an individual in need thereof. In another embodiment of the invention, the method of transplantation of combined stem cell populations comprises (a) mixing placental stem cells with a population of cord blood cells; (b) induction of differentiation of the mixture of the cord blood cells and placental stem cells and (c) administration of the mixture to a patient in need thereof.

The combined stem cell populations of the invention may be transplanted into a patient in any pharmaceutically or medically acceptable manner, including by injection, e.g., intravenous injection, intramuscular injection, intraperitoneal injection, intraocular injection, direct injection into a particular tissue, transfusion, etc. For example, combined stem cell populations, e.g., placental stem cells in combination with cord blood-derived stem cells) may be transplanted by intravenous infusion. In another embodiment, a combined stem cell population comprising placental stem cells and cardiac stem cells, in suspension, may be injected directly into cardiac tissue, e.g., an ischemic area in a heart. The combined stem cell populations may comprise, or be suspended in, any pharmaceutically-acceptable carrier. The combined stem cell populations may be carried, stored, or transported in any pharmaceutically or medically acceptable container, for example, a blood bag, transfer bag, plastic tube or vial.

After transplantation, engraftment in a human recipient may be assessed using, e.g., nucleic acid or protein detection or analytical methods. For example, the polymerase chain reaction (PCR), STR, SSCP, RFLP analysis, AFLP analysis, and the like, may be used to identify engrafted cell-specific nucleotide sequences in a tissue sample from the recipient. Such nucleic acid detection and analysis methods are well-known in the art. In one embodiment, engraftment may be determined by the appearance of engrafted cell-specific nucleic acids in a tissue sample from a recipient, which are distinguishable from background. The tissue sample analyzed may be, for example, a biopsy (e.g., bone marrow aspirate) or a blood sample.

In one embodiment, a sample of peripheral blood is taken from a patient immediately prior to a medical procedure, e.g., myeloablation. After the procedure, a combined stem cell population of the invention is administered to the patient. At least once post-administration, a second sample of peripheral blood is taken. An STR profile is obtained for both samples, e.g., using PCR primers for markers (alleles) available from, e.g., LabCorp (Laboratory Corporation of America). A difference in the number or characteristics of the markers (alleles) post-administration indicates that engraftment has taken place.

Engraftment can also be demonstrated by detection of re-emergence of neutrophils.

In another example, engrafted cell-specific markers may be detected in a tissue sample from the recipient using antibodies directed to markers specific to either the transplanted stem cells, or cells into which the transplanted stem cells would be expected to differentiate. In one embodiment, engraftment of a combination of placental stem cells and cord blood-derived stem cells may be assessed by FACS analysis to determine the presence of $CD45^+$, $CD19^+$, $CD33^+$, $CD7^+$ and/or $CD3^+$ cells by adding the appropriate antibody and allowing binding; washing (e.g., with PBS); fixing the cells (e.g., with 1% paraformaldehyde); and analyzing on an appropriate FACS apparatus (e.g., a FACSCalibur flow cytometer (Becton Dickinson)). In another embodiment, engraftment of a combination of placental stem cells and cord blood-derived stem cells may be assessed by FACS analysis to determine the presence of $CD200^+$ or $HLA-G^+$ cells. Where placental stem cells and/or stem cells from a second source are from an individual of a different sex than a recipient, e.g., male donor and female recipient, engraftment can be determined by detection of sex-specific markers, e.g., Y-chromosome-specific markers. Placental stem cells and/or stem cells from a second source may also be genetically modified to express a unique marker or nucleic acid sequence that facilitates identification, e.g., an RFLP marker, expression of β-galactosidase or green fluorescent protein, or the like.

The degree of engraftment may be assessed by any means known in the art. In one embodiment, the degree of engraftment is assessed by a grading system as follows, which uses a thin section of fixed and antibody-bound tissue from the transplant recipient. In this example grading system, engraftment is graded as follows: 0=no positive cells (that is, no cells bound by an antibody specific to an engrafted cell); 0.5=one or two positive cells, perhaps positive, but difficult to differentiate from background or non-specific staining; 1=2-20 scattered positive cells; 2=approximately 20-100 scattered or clustered positive cells throughout the tissue; 3=more than 100 positive cells comprising less than 50% of the tissue; 4=more than 50% of cells are positive. In specific embodiments, engraftment is determined where greater than 0.5%, 1%, 2%, 3%, 4%, 5%, 7.5%, 10%, 15%, 20% or greater of the cells are positively stained.

In another embodiment, the degree of engraftment is determined by analysis of the gain of one or more biological functions carried out by the engrafted cells. For example, where a recipient, who has undergone myeloablative therapy, receives a transplant of a combined stem cell population comprising placental stem cells and cord blood-derived stem cells, the degree of engraftment may be determined by the degree to which normal hematopoiesis, blood cell populations and blood function return to normal.

Where the combined stem cell population in whole or in part is HLA-mismatched to an intended recipient, it may be necessary to treat the recipient to reduce immunological rejection of the donor cells. Methods for reducing immunological rejection are disclosed in, e.g., U.S. Pat. Nos. 5,800,539 and 5,806,529, both of which are incorporated herein by reference.

5.4.2 Dosages

Typically, a patient receiving a stem cell infusion, for example for a bone marrow transplantation, receives one unit of nucleated cells, where a unit is approximately $1 \times 10^9$ nucleated cells (corresponding to $1-2 \times 10^6$ $CD34^+$ stem cells). Transplantation of a combined stem cell population into an individual comprises, in various embodiments, transplantation of at least one hundred thousand, 1 million, 10 million, 100-200 million, 1 billion, 3 billion, 5 billion, 10 billion, 15 billion, 20 billion, 30 billion, 40 billion, 50 billion or more, or, alternatively, 3, 5, 10, 20, 30, 40, or 50 units or more, of total nucleated cells, from both the placental stem cell population and the stem cell population from a second source. Transplantation of a combined stem cell population into an individual comprises, in other embodiments, transplantation of at least 10-20 million, 100 million, 300 million, 500 million, 1 billion, 1.5 billion, 2 billion, 3 billion, 4 billion, 5 billion, 6 billion, 7 billion, 8 billion, 9 billion, 10 billion or more stem cells. In another embodiment, the number of nucleated cells administered to an individual is at least five times the number of cells normally administered in a bone marrow replacement. In another specific embodiment of the method, the number of nucleated cells administered to an individual is at least ten times the number of cells normally administered in a bone marrow replacement. In another specific embodiment, the number of nucleated cells administered to an individual is at least fifteen times the number of cells normally administered in a bone marrow replacement. In another embodiment of the method, the total number of nucleated cells, which includes stem cells, administered to an individual is between $1-1000 \times 10^8$ per kilogram of body weight.

5.5 Methods of Treatment Using Combined Stem Cell Populations

The combined stem cell populations of the invention can be used to treat an individual in need of engraftable stem cells. Such an individual, for example, may require a transplantation of stem cells to effect hematopoietic reconstitution. In various other embodiments, the combined stem cell populations may be used to treat an individual having a blood cancer, a lysosomal storage disease, an inflammatory disorder, or an autoimmune disorder. In other embodiments, the combined stem cell populations may be used to facilitate organ regeneration or repair, or may be used as a transgene carrier.

Thus, in one embodiment, the invention provides a method of treating an individual, comprising contacting (e.g., administering to) an individual with a combined stem cell population of the invention. In another embodiment, the invention provides a method of treating an individual comprising identifying a combined stem cell population, and contacting said individual with said combined stem cell population. In a specific embodiment, the combined stem cell populations comprise placental stem cells and stem cells from a second source in a ration, in a total number of cells, that improves or enhances engraftment compared to a number of placental stem cells or stem cells from a second source, equivalent to said total number of cells, alone. In another embodiment, the invention provides a method of treating an individual, comprising introducing to said individual a composition comprising placental stem cells and stem cells from a second source in a ratio, wherein said ratio is selected by identifying a ratio in a plurality of ratios of numbers of placental stem cells to stem cells from a second source that, when cultured in vitro for a time and under conditions sufficient to allow the formation of colony-forming units, produces the greatest number of colony forming units, the numbers of cells in the colony-forming unit being equivalent in each condition, wherein said individual has a disease, disorder or condition treatable with stem cells. In a specific embodiment, said stem cells from a second source are umbilical cord blood or placental blood stem cells. In another specific embodiment, said stem cells from a second source are hematopoietic stem cells. In another specific embodiment, said stem cells from a second source are bone marrow-derived stem cells. In another specific embodiment, said treating is prophylactic. In another specific embodiment, said treating is therapeutic. In various embodiments, said disease, disorder or condition is one of the diseases, disorders or conditions listed below. The list of diseases, disorders, and conditions provided herein is not intended to be limiting.

One use of combined stem cell populations, particularly stem cell populations comprising placental stem cells and umbilical cord blood, or umbilical cord blood-derived stem cells, is hematopoietic reconstitution in, e.g., patients who have undergone partial or complete myeloablative therapy as part of an anticancer regimen. Typically bone marrow stem cells are transplanted to effect hematopoietic reconstitution, at a dosage of approximately $1 \times 10^8$ to $2 \times 10^8$ bone marrow mononuclear cells per kilogram of patient weight must be infused for engraftment in a bone marrow transplantation, or about $1-8 \times 10^6$ $CD34^+$ stem cells (i.e., about 70 ml of marrow for a 70 kg donor). Hematopoietic reconstitution may be accomplished by introduction to an individual of an equivalent number of total nucleated cells in a combined stem cell population comprising, e.g., placental stem cells and stem cells from a second source, e.g., placental blood or cord blood.

Placental stem cells and stem cells from a second source can be fully or partially immunologically matched to a recipient, or can be from a completely unrelated individual. In one embodiment, individuals receiving a combined stem cell population receive $\geq 3.5 \times 10^7$ total nucleated cells (TNC), e.g., from umbilical cord blood, per kg body weight for 5/6 HLA matched cells, or $\geq 5.0 \times 10^7$ total nucleated cells (TNC)/kg body weight for 4/6 HLA matched cells. Infusion of TNC, e.g., from UCB, is followed, e.g., immediately, by an infusion of about 5 to about $30 \times 10^6$ TNC from placental perfusate per kg body weight. An individual can receive a single of such doses, or multiple such doses.

In one embodiment, therefore, combined stem cell populations comprising hematopoietic stem cells can be used to treat patients having a blood cancer, such as a lymphoma, leukemia (such as chronic or acute myelogenous leukemia, acute lymphocytic leukemia, Hodgkin's disease, etc.), myelodysplasia, myelodysplastic syndrome, and the like. In another embodiment, the disease, disorder or condition is chronic granulomatous disease.

Because hematopoietic reconstitution can be used in the treatment of anemias, the present invention further encompasses the treatment of an individual with a stem cell combination of the invention, wherein the individual has an anemia or disorder of the blood hemoglobin. The anemia or disorder may be natural (e.g., caused by genetics or disease), or may be artificially-induced (e.g., by accidental or deliberate poisoning, chemotherapy, and the like). In another embodiment, the disease or disorder is a marrow failure syndrome (e.g., aplastic anemia, Kostmann syndrome, Diamond-Blackfan anemia, amegakaryocytic thrombocytopenia, and the like), a bone marrow disorder or a hematopoietic disease or disorder.

In another embodiment, the combined stem cell populations of the invention can be introduced into a damaged organ for organ neogenesis and repair of injury in vivo. Such injury may be due to conditions and disorders including, but not limited to, myocardial infarction, seizure disorder, multiple sclerosis, stroke, hypotension, cardiac arrest, ischemia, inflammation, age-related loss of cognitive function, cerebral palsy, neurodegenerative disease, Alzheimer's disease, Parkinson's disease, Leigh disease, AIDS dementia, memory loss, amyotrophic lateral sclerosis, ischemic renal disease, brain or spinal cord trauma, heart-lung bypass, glaucoma, retinal ischemia, or retinal trauma.

In other embodiments, the disease, disorder or condition treatable using the combined stem cell populations include, but are not limited to lysosomal storage diseases, such as Tay-Sachs, Niemann-Pick, Fabry's, Gaucher's disease (e.g., glucocerebrosidase deficiency), Hunter's, and Hurler's syndromes, Maroteaux-Lamy syndrome, fucosidosis (fucosidase deficiency), Batten disease (CLN3), as well as other gangliosidoses, mucopolysaccharidoses, and glycogenoses.

The combined stem cell populations can also be used to treat severe combined immunodeficiency disease, including, but not limited to, combined immunodeficiency disease (e.g., Wiskott-Aldrich syndrome, severe DiGeorge syndrome, and the like).

In other embodiments, combined stem cell populations may be used as autologous or heterologous transgene carriers in gene therapy to correct, for example, inborn errors of metabolism, adrenoleukodystrophy (e.g., co-A ligase deficiency), metachromatic leukodystrophy (arylsulfatase A deficiency) (e.g., symptomatic, or presymptomatic late infantile or juvenile forms), globoid cell leukodystrophy (Krabbe's disease; galactocerebrosidase deficiency), acid lipase deficiency (Wolman disease), cystic fibrosis, glycogen storage disease, hypothyroidism, sickle cell anemia, thalassemia (e.g., beta thalassemia), Pearson syndrome, Pompe's disease, phenylketonuria (PKU), porphyrias, maple syrup urine disease, homocystinuria, mucoplysaccharidosis, chronic granulomatous disease and tyrosinemia and Tay-Sachs disease or to treat solid tumors or other pathological conditions.

In other embodiments, the disease, disorder or condition is a disease, disorder or condition requiring replacement or repair of one or more tissues. For example, the combined stem cell populations of the invention can be used in therapeutic transplantation protocols, e.g., to augment or replace stem or progenitor cells of the liver, pancreas, kidney, lung, nervous system, muscular system, bone, bone marrow, thymus, spleen, mucosal tissue, gonads, or hair. The combined stem cell populations of the invention can also be used for augmentation, repair or replacement of, e.g., cartilage, tendon, or ligaments. For example, in certain embodiments, prostheses (e.g., hip prostheses) are coated with replacement cartilage tissue constructs grown from combined stem cell populations of the invention. In other embodiments, joints (e.g., knee) are reconstructed with cartilage tissue constructs grown from combined stem cell populations. Cartilage tissue constructs can also be employed in major reconstructive surgery for different types of joints (for protocols, see e.g., Resnick, D., and Niwayama, G., eds., 1988, DIAGNOSIS OF BONE AND JOINT DISORDERS, 2D ED., W. B. Saunders Co.). The combined stem cell populations of the invention can be used to repair damage of tissues and organs resulting from trauma, metabolic disorders, or disease. In one embodiment, a patient can be administered a combined stem cell population to regenerate or restore tissues or organs which have been damaged as a consequence of disease, e.g., to repair heart tissue following myocardial infarction.

In another embodiment, the combined stem cell populations of the invention may be used to treat an individual who has received a lethal or sub-lethal dose of radiation. Such radiation may be accidentally received, for example in a nuclear incident, whether work- or aggression-related, or therapeutic, for example, as part of a medical procedure. The particular type of radiation (e.g., alpha, beta, gamma) is not critical. The combined stem cell populations of the invention may be used to ameliorate one or more symptoms of radiation sickness, for example, nausea, loss of appetite, lethargy, dyspnea, decreased white blood cell count, chronic anemia, fatigue, weakness, paleness, difficulty breathing, feelings of malaise, and the like, whether such symptoms are indicative of recoverable or fatal radiation sickness. In another embodiment, the individual has one or more symptoms associated with acute radiation syndrome (ARS). The combined stem cell populations of the invention may also be used to partially or fully reconstitute the hematopoietic system of an individual that has received a lethal or sub-lethal dose of radiation, such that the individual becomes partially or fully chimeric. Such chimerism may be temporary or permanent (e.g., may persist for 1, 2, 3 weeks, or 1, 2, 3, 4, 5, 6, 7, 8, 9, 10, 11 months or longer). In a preferred embodiment, a combined stem cell population of the invention is provided to the individual within the first 24 hours after exposure. The individual may be administered a combined stem cell population within the first hour, 2 hours, 3 hours, 4 hours, 5 hours, 6 hours, 9 hours, 12 hours, 15 hours, 18 hours, or 21 hours after exposure to radiation. A combined stem cell population of the invention may also be administered within 2 days, 3 days, 4 days, 5 days, 6 days, one week, 2 weeks, 3 weeks, 4 weeks or 5 weeks after exposure to radiation.

The combined stem cell populations are expected to have an anti-inflammatory effect when administered to an individual experiencing inflammation. In a preferred embodiment, the combined stem cell populations of the invention may be used to treat any disease, condition or disorder resulting from, or associated with, inflammation. The inflammation may be present in any organ or tissue, for example, muscle; nervous system, including the brain, spinal cord and peripheral nervous system; vascular tissues, including cardiac tissue; pancreas; intestine or other organs of the digestive tract; lung; kidney; liver; reproductive organs; endothelial tissue, or endodermal tissue.

The combined stem cell populations may also be used to treat autoimmune or immune system-related disorders, including those associated with inflammation. Thus, in certain embodiments, the invention provides a method of treating an individual having an autoimmune disease or condition, comprising administering to such individual a therapeutically effective amount of the cells or supplemented cell populations of the invention, wherein said disease or disorder can be, but is not limited to, diabetes, amyotrophic lateral sclerosis, myasthenia gravis, diabetic neuropathy or lupus. In related embodiments, the combined stem cell populations of the invention may be used to treat immune-related disorders, such as chronic or acute allergies.

Combined stem cell populations may also be administered to a nominally healthy individual to increase the individual's overall health and well-being.

Therapeutic or prophylactic treatment of an individual with combined stem cell populations may be considered effective if the disease, disorder or condition is measurably improved in any way. Such improvement may be shown by a number of indicators. Measurable indicators include, for example, detectable changes in a physiological condition or set of physiological conditions associated with a particular disease, disorder or condition (including, but not limited to, blood pressure, heart rate, respiratory rate, counts of various blood cell types, levels in the blood of certain proteins, carbohydrates, lipids or cytokines or modulation expression of genetic markers associated with the disease, disorder or condition). Treatment of an individual with the stem cells or supplemented cell populations of the invention would be considered effective if any one of such indicators responds to such treatment by changing to a value that is within, or closer to, the normal value. The normal value may be established by normal ranges that are known in the art for various indicators, or by comparison to such values in a control. Introduction of a combined stem cell population of the invention for the purposes of engraftment, e.g., hematopoietic engraftment, would be considered successful if the individual to whom the combined stem cell population is introduced exhibits any indications of engraftment (e.g., markers of engrafted cells appearing in biopsy or tissue samples, or blood sample; detection of one or more biochemical functions performed by the engrafted cells, etc.). In medical science, the efficacy of a treatment is also often characterized in terms of an individual's impressions and subjective feeling of the individual's state of health. Improvement therefore may also be characterized by subjective indicators, such as the individual's subjective feeling of improvement, increased well-being, increased state of health, improved level of energy, or the like, after administration of the stem cells or supplemented cell populations of the invention.

5.6 Stem Cell Bank

The methods described above, particularly the in vitro method (see Section 5.1.1) may be performed on individual units of, for example, placental perfusate, placental stem cells, cord blood, cord blood stem cells, and the like, to produce combined stem cell populations for the treatment of an individual in need of stem cells. As such, the assay may be used as part of a method of stem cell banking or blood banking, including a cord blood banking, wherein providing stem cells is at least a part of said banking. The assay may be performed on each of a plurality of units of placental stem cells, and stem cells from a second source, used or provided by a blood bank, stem cell registry, or similar operation.

For example, in one embodiment, the invention provides a method of stem cell banking comprising providing a plurality of units of combined stem cell populations comprising a number of placental stem cells and stem cells from a second source, wherein said combined stem cell populations exhibit improved or enhanced engraftment compared to a number of said placental stem cells or of said stem cells from a second source, equivalent to the number of cells in said combined stem cell population, alone. In a specific embodiment, said combined stem cell populations are generated by a method comprising providing a plurality of units of placental stem cells; providing a second plurality of stem cells from a second source; matching each said units of placental stem cells with a unit of stem cells from a second source; and identifying a ratio of said placental stem cells to said stem cells from a second source in a total number of cells that, when combined for a time and under conditions sufficient to allow the formation of colony-forming units, produces a greater number of colony-forming units than a number of said placental stem cells or of said stem cells from a second source, equivalent to said total number of cells, alone. In a specific embodiment, said stem cells from a second source are cord blood or placental blood stem cells. In another specific embodiment, said stem cells from a second source are peripheral blood stem cells. In another specific embodiment, said stem cells from a second source are bone marrow stem cells. In another specific embodiment, said placental stem cells and said stem cells from a second source are randomly matched. In another specific embodiment, said placental stem cells and said stem cells from a second source are matched based on a characteristic of said unit of placental stem cells and of said unit of stem cells from a second source. In a more specific embodiment, said characteristic is the number of total nucleated cells in said unit of placental stem cells and in said unit of stem cells from a second source. In another more specific embodiment, said characteristic is the number of stem cells in said unit of placental stem cells and in said unit of stem cells from a second source. In another more specific embodiment, said characteristic is an immunological marker displayed by said placental stem cells and by said stem cells from a second source.

The invention further provides a bank of placenta-derived stem cells, e.g., a bank of units of placenta-derived stem cells and stem cells from a second source, wherein a number of said placenta-derived stem cells and stem cells from a second source are provided together in a ratio that produces more colony-forming units in a total number of cells, under conditions that allow the formation of colony-forming units, than a number of placental stem cells or said number of stem cells from a second source, equivalent to said total number of cells, alone. In a preferred embodiment, the bank comprises a plurality of units of placenta-derived stem cells that are matched, or otherwise identified as combinable with, one or more units of stem cells from a second source in ratios, specific to the respective units, that, when the units are combined, show greater numbers of colony-forming units in a colony-forming unit assay, or improved engraftment when transplanted into a recipient, as compared to an equivalent number of placenta-derived stem cells or stem cells from a second source, alone. The bank can comprise separate, matched units of placenta-derived stem cells and stem cells from a second source, or units of combined stem cell populations.

Placenta-derived stem cells contained within such a bank, or within units of combined stem cell populations within such a bank, can be, for example, cells contained within perfusate obtained directly from a placenta, placenta-derived stem cells isolated from placental perfusate or enzymatic digestion of placenta and contained within a nucleated cell fraction, a population of placenta-derived stem cells isolated from the remainder of placenta cells according to, e.g., one or more cell surface markers, or a population of stem cells cultured and/or expanded from any of the foregoing. Stem cells from a second source can be contained within a tissue homogenate or other collection of tissue-specific cells, e.g., whole umbilical cord blood or placental blood, stem cells isolated from the second source to any degree, or stem cells cultured and/or expanded from any of the foregoing.

Preferably, the placental stem cells and stem cells from a second source are derived from the same individual. In a specific embodiment, said stem cells from a second source are cord blood and/or placental blood stem cells from the placenta from which the placental stem cells are obtained or derived. In a preferred embodiment, the bank comprises a plurality of units of combined stem cell populations comprising placental stem cells and stem cells from umbilical cord blood or placental blood units, from the same individual, in ratios, specific to the respective units, that produce greater numbers of colony-forming units in a colony-forming unit assay, or improved engraftment when transplanted into a recipient, for a total number of cells, compared to a number of placenta-derived stem cells or stem cells from a second source, equivalent to said total number of cells, alone.

Preferably, placenta-derived stem cells in the stem cell bank are characterized by at least one HLA marker. In a preferred embodiment, the bank comprises a plurality of units of HLA-characterized placenta-derived stem cells. In one embodiment, the invention provides a stem cell bank comprising a plurality of units of placenta-derived stem cells, wherein said placenta-derived stem cells are identified by at least one HLA marker. In a specific embodiment, said placenta-derived stem cells are isolated from placental perfusate. In another specific embodiment, said placenta-derived stem cells are contained within a population of nucleated cells isolated from placental perfusate. In another specific embodiment, said placenta-derived stem cells are $CD34^+$ stem cells. In another specific embodiment, said placenta-derived stem cells are positive for CD105 or CD73, or bind antibodies SH2, SH3 and/or SH4. In another specific embodiment, said placenta-derived stem cells are positive for OCT-4 and/or HLA-G.

In one embodiment, the stem cell bank of the invention comprises a plurality of units of blood or blood-derived stem cells, e.g., placental blood or umbilical cord blood, or stem cells obtained from umbilical cord or placental blood. Preferably, at least one, and preferably a majority, of the units of blood or blood-derived stem cells contained within the stem cell bank are, or can be, HLA-matched to at least one, or preferably a majority, of the units of placenta-derived stem cells contained within the bank. Thus, in another specific embodiment, said stem cell bank additionally comprises a plurality of units of blood or blood-derived stem cells. In another specific embodiment, at least one unit of said plurality of units of blood or blood-derived stem cells is identified by at least one HLA marker shared by one of said plurality of units of placenta-derived stem cells. In another specific embodiment, a majority of units within said plurality of units of placental blood or umbilical cord blood is identified by an HLA marker shared by a majority of units within said plurality of units of placenta-derived stem cells.

The units of placenta-derived stem cells and units of blood-derived stem cells contained within the stem cell bank are preferably indexed and cross-matched for easy identification and combination to introduce into a specific individual. For example, a specific individual having a particular HLA marker, or HLA marker profile, can be matched to one or more units of placenta-derived stem cells and, preferably, one or more units of blood-derived stem cells, e.g., umbilical cord blood or placental blood. Preferably, the placenta-derived stem cells and blood stem cells are combined to form a combined stem cell population of the invention prior to administration to said individual. Such a combined stem cell population may be produced according to the methods described elsewhere herein.

The stem cell bank may comprise placenta-derived stem cells and/or matched units of blood obtained from any number of individuals. In various embodiments, the stem cell bank of the invention may comprise units of placental stem cells and/or units of blood, e.g., placental blood and/or umbilical cord blood, obtained from at least 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 700000, 800000, 900000 or 1000000, or more, individuals.

5.7 Kits

The invention further provides kits that can be used to identify and/or prepare the combined stem cell populations of the invention. Such kits enable the user to determine an appropriate ratio of placental stem cells and stem cells from a second source to use to prepare a combined stem cell population. Such kits can be used to prepare combined stem cell populations that reflect the physiological status of the individual unit or units of placental stem cells, and stem cells from a second source, used to make the combined stem cell populations. In particular, such kits enable a user to perform a colony-forming unit assay using placental stem cells and stem cells from a second source.

Thus, in one embodiment, the invention provides a kit comprising, in a sealed container, a population of placental stem cells and a plurality of containers suitable for performing a colony-forming assay. In a specific embodiment, said plurality of containers is a plurality of wells in a tissue culture plate. Said plate may comprise at least 8, at least 12, at least 24, at least 48, at least 96, or at least 128 wells.

In another specific embodiment, said kit comprises a set of instructions for the co-culture of placental stem cells and stem cells from a second source. In a more specific embodiment, said instructions comprise instructions for culturing said placental stem cells and said stem cells from a second source for the production of colony-forming units. In another more specific embodiment, said instructions comprise instructions for co-culturing said placental stem cells and said stem cells from a second source in a plurality of ratios, and for selecting one of said plurality of ratios.

In another specific embodiment, said kit comprises one or more containers of medium suitable for the isolation of stem cells. In another specific embodiment, said kit contains one or more containers of medium suitable for the culture and/or differentiation of stem cells into colony-forming units. In a more specific embodiment, said medium is a methylcellulose-based or starch-based medium. In another more specific embodiment, said medium is a culture medium suitable for culturing stem cells. In an even more specific embodiment, said medium is Methocult GF$^+$ H4435 medium, RPMI 1640 medium supplemented with 2% fetal calf serum and 1% Stemspan CC100 cytokine cocktail, Dulbecco's Modified Eagle's Medium (DMEM) or Iscove's Modified Dulbecco's Medium (IMDM).

In other specific embodiments, the kit comprises a scoring grid, wherein said scoring grid facilitates the counting of colony-forming units. In another more specific embodiment, said kit comprises a hemacytometer.

In another specific embodiment, the kit comprises a container suitable for combining and storing placental stem cells and stem cells from a second source in a ratio identified as described above. In more specific embodiments, said container is a blood bag.

In various other embodiments, the kit comprises one or more of a disposable (e.g., gloves, towelettes, and the like); a log for recording results; labels for containers, etc.

In another specific embodiment, said kit comprises statistical software for determining which of a plurality of ratios of placental stem cells to stem cells from a second source yields a significantly higher number of colony-forming units than any other of said plurality of ratios.

6. EXAMPLES 6.1 Example 1

In Vitro Colony Forming Unit Assay

Total nucleated cells are isolated from a unit of cord blood by Hetastarch separation. Total nucleated placental cells are obtained from 750 milliliters of placental perfusate by Ficoll separation. The total nucleated cells from placenta and cord blood are combined in triplicate in 35 mm culture dishes in Methocult GF$^+$ H4435 medium (Stem Cell Technologies, Vancouver, Canada), or RPMI 1640 medium supplemented with 2% fetal calf serum and 1% Stemspan CC100 cytokine cocktail (Stem Cell Technologies, Vancouver, Canada). Cells are combined in at least two ratios (e.g., $2\times10^5$:$2\times10^5$; $1\times10^5$: $3\times10^5$; $3\times10^5$:$1\times10^5$), and are cultured for 14 days. The morphology of the cells is then examined under phase contrast microscope, and the total number of colony-forming units (e.g., CFU-GM, CFU-L, CFU-M, CFU-G, CFU-DC, CFU-GEMM, CFU-E) are recorded. A determination is then made as to which ratio produces the highest number of colony-forming units.

6.2 Example 2

Co-Culture Assay Using Hematopoietic Stem Cells

Ten HLA/donor matched placental perfusate and cord blood units were thawed and total nucleated cells (TNC) were counted on a Cell-Dyn 1700 (Abbott Laboratories, Abbott Park, Ill.). The CFU assays of the co-culture experiments were studied in triplicate in 35 mm dishes in MethoCult GF+ H4435 Medium (StemCell Technologies, Vancouver, Canada). Mononuclear cells were seeded as follows: placental perfusate-derived stem cells (PP) alone at 50 (low seeding group), 250 (medium seeding group) and 5000 (high seeding group)×10³/mL/dish; cord blood-derived stem cells (CB) alone at 50×10³/mL/dish; and placental perfusate-derived stem cells and cord blood-derived stem cells in co-culture, with 50×10³/mL/dish cord-blood-derived cells in combination with 50, 250 and 5000×10³/mL/dish placental perfusate-derived stem cells. Colony forming unit assays were read on day 14 after seeding. The increase in the number of total colony-forming units was calculated based on the formula: % increase in total colony-forming units=CB/PP−(CB+PP)/(CB/PP)×100.

A total of 10 matched CB and PP samples were co-cultured. In 4 of the 10 co-cultures, total CFU activity increased in counts per dish as compared to CB or PP culture alone. The percentage increase of total colony-forming unit activity varied from 7.1% to 43.1% in the low seeding group, 14.9% to 42.1% in the medium seeding group, and 24.4% to 43.8% in the high seeding group.

6.3 Example 3

Pre-Clinical Studies to Evaluate the Hematopoietic Reconstitution Activity of Human Placenta Perfusate and Umbilical Cord Blood by Accessing SCID-Repopulating Cell Activity

6.3.1 Introduction

The stem cell properties of cells present in the UCB and HPSC were evaluated using quantitative assessments in a xenogeneic transplant model using immunodeficient NOD/SCID mice. Reported herein are results of the initial experiments to determine the frequency and absolute number of NOD/SCID repopulating cells in UCB and HPSC by limiting dilution transplant studies.

6.3.2 Materials and Methods

6.3.2.1 Collection and Cryopreservation of UCB Units

Briefly, after informed consent of the mother was obtained, the UCB were harvested at hospital in a triple-bag system containing citrate/phosphate/dextrose solution. The units were stored and processed at room temperature within 48 hours of blood collection. A Hetastarch-based method was used to perform volume reduction and RBC depletion. The final TNC were frozen in a cryobag containing 40 mL of 10% DMSO and autologous plasma in LN2 tank in vapor phase.

6.3.2.2 Placental Perfusion and Cryopreservation of HPSC Units

Placental stem cells were collected by placental perfusion according to the methods disclosed in United States Application Publication Nos. 2002/0123141 and 2003/0032179, each of which is incorporated herein by reference in its entirety. Briefly, placentas from the umbilical cord blood donors were drained of umbilical cord and perfused with 0.9% NaCl solution at controlled pressure. A total of 750 mL perfusate was obtained. The cells were concentrated and separated by gradient separation (Ficoll-Hypaque) to deplete RBC and cell debris.

6.3.2.3 Cell Counting and Viability

Cell counts were performed with automated cell analyzers (Cell-Dyn 1700 or Cell-Dyn3200, Abbott; Wiesbaden, Germany) and by manual counting. The viability of the cells was determined using trypan blue exclusion.

6.3.2.4 Phenotyping of Umbilical Cord Blood (UCB) and Placental Perfusate (HPSC) Units Single donor matching units of UCB and HPSC were maintained in liquid nitrogen until the time of use. On the day of transplant, the units were thawed. The viability of freshly thawed UCB and HPSC units was determined using trypan blue. Post-thaw recovery of total nucleated cell counts was also performed. Prior to transplant, an aliquot (0.5 ml) of freshly thawed cells was then used for FACS analysis for the following cell surface markers: CD34, CD38, CD33, CD14, CD7, CD3, CD56, CD10 and CD19.

6.3.2.5 Limiting Dilution NOD/SCID Repopulating Cell Assay

Quantitative studies using limiting dilution SCID repopulating cell (SRC) assays were carried out using NOD/SCID mice at 8-10 weeks of age. The mice were irradiated at 325-350 cGy with irradiation from a linear accelerator at an exposure rate of 20 cGy/min prior to transplantation. Mice were then transplanted intravenously via the lateral tail vein with 200 μl of cells from cord blood or placental perfusate or the combination of cord blood and placental perfusate. Transplants comprised approximately $2$-$10 \times 10^5$ stem cells per kg (non-expanded) or $1$-$2 \times 10^6$ stem cells per kg (expanded). Four cell doses were used in order to calculate the frequency of repopulating cells and 6 mice per group were transplanted. Mice were then analyzed for human cell engraftment at three weeks post transplant and at 10 weeks post transplant. Cells were obtained from 25 μl of aspirated bone marrow harvested from the femur and then analyzed by FACS analysis for human lympho-myeloid engraftment. For each aspiration a tuberculin syringe with a 28-gauge needle was prepared containing approximately 30-40 uL of PBS. At 10 weeks, mice were sacrificed and cells harvested from both femurs, both tibiae, and the thymus for engraftment analysis. Additionally, in the second experiment carried out, necropsy was performed for all mice in the highest cell dose group and tissues collected for histology and presence of human cells. The tissues collected included: spleen, liver, lung, brain, heart, skeletal muscle, kidney and thymus. Engraftment was defined as ≧0.5% CD45+ cells.

6.3.3 Results

6.3.3.1 TNC, Viability and TNC Recovery of HPSC and UCB Units Used in Experiments Two matching units of HPSC and their matching UCB units were used independently for each experiment. Table 1 shows the TNC and post-thaw viability and TNC recovery rate of these cells. The two UCB units have TNC of $1237 \times 10^6$ and $778 \times 10^6$ and viability of 82% and 83%, respectively. HPSC units have a relatively lower TNC counts ($752.5 \times 10^6$ and $661.5 \times 10^6$) and viability (67% and 66% respectively) compared to the UCB units.

TABLE 1

TNC and viability of two matching placenta and UCB units used in NOD/SCID BTM engraftment experiments

|  | Exp-1 UCB | Exp-1 PP | Exp-2 UCB | Exp-2 PP |
|---|---|---|---|---|
| Prefreeze TNC ($\times 10^6$) | 1237 | 752.5 | 778.0 | 661.5 |
| Post-thaw Viability | 83% | 67% | 82% | 66% |
| Post-thaw TNC Recovery | 99% | 53% | >100% | >100% |

6.3.3.2 Phenotypic Analysis of UCB and HPSC

Table 2 outlines the results of the phenotypic analysis of the cord blood and placental perfusate cells prior to transplant. As expected, there was variability between the cord blood donors in experiment 1 and 2 with respect to the percent of CD34+ cells, with 0.56% of the cells being CD34+ in experiment 1 versus 1.67% CD34+ cells in experiment 2. These differences reflect the natural variability in TNC and numbers of CD34+ cells in umbilical cord blood between donors. In either case, the percent of CD34+ cells was greater in the cord blood than the placental perfusate. The cord blood was lower in the myeloid markers (CD33 and CD14), but higher in lymphoid markers (CD3 and CD7). A significantly higher number of cells in HPSC express CD10 than in cord blood.

TABLE 2

FACS analysis of matching UCB and HPSC units used in the NOD/SCID mice BTM engraftment experiments

|  | Exp-1 UCB | Exp-1 PP | Exp-2 UCB | Exp-2 PP |
| --- | --- | --- | --- | --- |
| CD34+ | 0.56% | 0.28% | 1.67% | 0.46% |
| CD34+CD38+ | 0.56% | 0.28% | 1.67% | 0.46% |
| CD33+ | 26.0% | 60% | 28.00% | 76.00% |
| CD14+ | 17.0% | 46% | 22.40% | 58.40% |
| CD7+ | 38.5% | 10.5% | 63.00% | 18.00% |
| CD3+ | 35.2% | 11.8% | 72.00% | 29.00% |
| CD56+ | 7.7% | 3.7% | 16.50% | 12.00% |
| CD10+ | 16.8% | 53.0% | 9.50% | 59.00% |
| CD19+ | 15.6% | 11.0% | 8.80% | 13.00% |

6.3.3.3 Engraftment of Human Cells in NOD/SCID Mice

Table 3 shows the cell doses of TNC infused to NOD/SCID mice in two independent experiments (Experiment 1 and 2). In both cases, equivalent numbers of CD34+ cells from UCB or HPSC were used in all mice received the UCB or HPSC. The TNC cell doses required for that number of CD34+ cells were infused to the mice accordingly. Six mice were used per dosage group.

TABLE 3

Cell dose of TNC transplantation in NOD/SCID mice

| CD34 equivalent | TNC/mouse: UCB | PP | UCB + PP | Mice/grp |
| --- | --- | --- | --- | --- |
| A. Experiment 1 | | | | |
| $1.5 \times 10^5$ | $15 \times 10^6$ | $15 \times 10^6$ | $30 \times 10^6$ | 6 |
| $3 \times 10^4$ | $3 \times 10^6$ | $3 \times 10^6$ | $6 \times 10^6$ | 6 |
| $6 \times 10^3$ | $6 \times 10^5$ | $6 \times 10^5$ | $1.2 \times 10^6$ | 6 |
| $1.2 \times 10^3$ | $1.2 \times 10^5$ | $1.2 \times 10^5$ | $2.4 \times 10^5$ | 6 |
| B. Experiment 2 | | | | |
| $2.4 \times 10^5$ | $24 \times 10^6$ | $24 \times 10^6$ | $48 \times 10^6$ | 6 |
| $8 \times 10^4$ | $8 \times 10^6$ | $8 \times 10^6$ | $16 \times 10^6$ | 6 |
| $1.1 \times 10^4$ | $1.1 \times 10^6$ | $1.1 \times 10^6$ | $2.4 \times 10^6$ | 6 |
| $8.9 \times 10^3$ | $8.9 \times 10^5$ | $8.9 \times 10^5$ | $1.8 \times 10^6$ | 6 |

FIG. 1 shows the summary of FACS analysis of engrafted human cells in mice bone marrow using CD45 antibodies in two independent experiments. At week 3 and week 10, mice bone marrow aspirates were analyzed for the presence of human CD45+ cells by FACS. Very low or undetectable numbers of human CD45+ cells were found in mice receiving placental cells alone in both time points in any cell doses. In contrast, at both time points, human cell engraftment was seen in mice transplanted with cord blood alone and with the combination of cord blood and placental perfusate. At 3 weeks, there was no significant difference seen in the level of human engraftment between the cord blood and combined cord blood and placental perfusate. However, at 10 weeks, the degree of human cell engraftment was significantly enhanced in mice receiving both cord blood cells and placental perfusate ($p=0.3$ in experiment 1 and $p=0.0002$ in experiment 2), as compared to engraftment in mice receiving umbilical cord blood stem cells or placental stem cells alone, indicating that placental stem cells enhance engraftment of the stem cells from a second source, e.g., umbilical cord blood.

To determine if the human engraftment cell included lymphomyeloid lineages, FACS analysis was also used to analyze co-expression of CD19, CD33 and CD7 in CD45+ cells from mouse bone marrow. The results from this experiment are shown in FIG. 2. These results show that the marrow of mice receiving both UCB and UCB+HPSC contained engrafted lymphoid and myeloid cells.

6.3.3.4 SCID Repopulating Cell (SRC) Frequency

The SCID Repopulating Cell frequency is the ratio of primitive hematopoietic stem cells, able to engraft and repopulate the hematopoietic system of an individual, to the total number of cells transplanted. The ratio provides an indication of the relative ability of a cell population to provide engraftable cells to, for example, an irradiated individual. Table 4 lists the SRC calculations from experiment 2 (see above). These numbers were calculated by limiting dilution transplants and application of the L-Calc software from StemCell Technologies. These studies did not demonstrate an enhancement of the SRC frequency, but as noted above, did show significant enhancement of overall human engraftment upon co-infusion of cord blood and placental perfusate. Thus, the data, in this instance, indicate that co-infusion of the placental perfusate with the UCB enhances stem cell engraftment, rather than increasing the overall number of stem cells.

TABLE 4

Estimation of SRC frequency from UCB and HPSC

|  | Frequency | Range |
| --- | --- | --- |
|  | WK-3 | WK-3 |
| UCB | 1/17,791,258 | 12,060,000 to 26,245,000 |
| PP | NA | NA |
| UCB + PP | 1/28,728,138 | 19,782,000 to 41,719,000 |
|  | WK-10 | WK-10 |
| UCB | 1/2,859,018 | 1,867,000 to 4,376,000 |
| PP | NA | NA |
| UCB + PP | 1/7,864,065 | 5,186,000 to 11,923,000 |

6.3.3.5 Engraftment of Human Cells in Non-Bone Marrow Tissues

To determine if human cells from UCB, HPSC or UCB+HPSC are engrafted in mouse tissues other than the bone marrow, the presence of human cells in experimental mouse thymus was determined by FACS analysis, and immunohistochemical staining was performed on mouse spleen tissue.

In experiment 1, FACS analysis of cells from mouse thymus showed that one mouse out of six co-infused with UCB and HPSC showed 0.8% human CD45+ cells. In experiment 2, one mouse out of six infused with UCB (dose 2) showed 8% of CD45+ cells, but no CD3+ or CD7+ cells. However, in the UCB+HPSC group, all six mice showed human engraftment with 3-23% CD45+ cells and one of these mice has shown CD3/CD7 positive cells.

Thin sections of the mice spleen were examined to detect the presence of human cells by staining with anti-vimentin and anti-CD45 antibodies that recognize human but not mouse proteins. Smooth muscle actin antibodies that recognize both human and mouse proteins were used as a positive control and IgG1 and IgG2a isotypes were used as negative controls. The results of the staining from each engraftment group are shown in Table 5.

TABLE 5

Detection of human cells in the spleen of NOD/SCID mice by immunohistochemstry

| Mouse Number | Product | Vimentin | CD45 | Smooth muscle actin | IgG1 | IgG2a |
|---|---|---|---|---|---|---|
| 304 | UCB-1 & PP-1 | 3+ | 2+ | 2+ | − | − |
| 305 | UCB-1 & PP-1 | 2+ | 1+ (few) | 2+ | − | − |
| 306 | UCB-1 & PP-1 | 3+ | 2+ | 2+ | − | − |
| 307 | UCB-1 & PP-1 | 3+ | 2+ | 2+ | − | − |
| 308 | UCB-1 & PP-1 | 3+ | 2+ | 2+ | − | − |
| 350 | PP-1 | − | − | 2+ | − | − |
| 351 | PP-1 | − | − | 2+ | − | − |
| 352 | PP-1 | − | − | 2+ | − | − |
| 353 | PP-1 | − | − | 2+ | − | − |
| 354 | PP-1 | ± (very few) | − | 2+ | − | − |
| 355 | PP-1 | − | − | 2+ | − | − |
| 370 | UCB-1 | 2+ | − | 2+ | − | − |
| 371 | UCB-1 | 1+ (few) | − | 2+ | − | − |
| 372 | UCB-1 | 2+ | 1+ (few) | 2+ | − | − |
| 373 | UCB-1 | ± (very few) | − | 2+ | − | − |
| 374 | UCB-1 | 1+ (few) | − | 2+ | − | − |
| 375 | UCB-1 | 1+ (few) | − | 2+ | − | − |
| Human tonsil | NA | 3+ | 3+ | 2+ | − | − |

Cells in the mouse spleen expressing human vimentin, a mesenchymal cell marker, were detectable in all mice receiving UCB cells alone. Vimentin staining was barely detectable in the mice receiving HPSC alone. However, significantly higher levels of vimentin staining were detected in the mice receiving both UCB and HPSC cells. Similar results were found when the spleen tissue was stained with antibodies to CD45, a hematopoietic cell marker. Smooth muscle actin (positive control) staining of the mouse spleen showed a uniform level of staining on all tissues. The isotype negative control antibodies did not stain the tissues.

6.3.4 Discussion

In these experiments, co-infusion of placental cells with cord blood cells from the same donor was shown to enhance the level of human stem cell engraftment in mice at 10 weeks over infusion of cord blood or placental cells alone. The enhanced human cell engraftment in NOD/SCID mice was also found in tissues including thymus and spleen. The engrafted cells are shown to include both myeloid and lymphoid cells. Engrafted human cells stained positive with vimentin in mouse spleens, indicating that the engraftment of human stem cells is enhanced by the UCB-HPSC co-infusion.

6.4 Example 4

Engraftment in NOD/SCID Mice

A dose range pilot study was performed in which combinations of human umbilical cord blood cells and placental cells were administered to sub-lethally-irradiated NOD/SCID mice in different ratios, and in which the degree of engraftment of, and repopulation by, human cells was determined.

Six groups of NOD/SCID mice, a model of human transplant engraftment, were sublethally irradiated at 400 cGy and dosed intravenously with one of three doses of cord blood cells and placental cells, based on the number of live total nucleated cells, at either a 3:1 or 1:1 ratio of cord blood cells to placental cells. FACS analysis was performed on the cells following combination and injection. Mice were monitored for engraftment of human cells by blood and bone marrow sampling at 10 weeks after administration.

Mice were administered one of the combinations of cord blood calls and placental cells shown in Table 6:

TABLE 6

Combinations of umbilical cord cells and placental cells administered to NOD/SCID mice
Quantitative SCR Assay in NOD/SCID Mice
With Cord Blood Cells and Placental Cells*

| Group | Cell Ratio | Cord Blood Cells (Live TNC) | Placental Cells (Live TNC) | Total Cells (Live TNC) | Dose Volume (μL) | Numer of Mice (Males) |
|---|---|---|---|---|---|---|
| | | | Subset A: | | | |
| 1 | 1:1 | $4.5 \times 10^6$ | $4.5 \times 10^6$ | $9 \times 10^6$ | 200 | 10 |
| 2 | 1:1 | $9 \times 10^6$ | $9 \times 10^6$ | $18 \times 10^6$ | 200 | 10 |
| 3 | 1:1 | $18 \times 10^6$ | $18 \times 10^6$ | $36 \times 10^6$ | 200 | 10 |
| | | | Subset B: | | | |
| 1 | 3:1 | $4.5 \times 10^6$ | $1.5 \times 10^6$ | $6 \times 10^6$ | 200 | 10 |
| 2 | 3:1 | $9 \times 10^6$ | $3 \times 10^6$ | $12 \times 10^6$ | 200 | 10 |
| 3 | 3:1 | $18 \times 10^6$ | $6 \times 10^6$ | $24 \times 10^6$ | 200 | 10 |

*Cell ratio subsets contained single units at each dose level (i.e., groups 1 and 4 used the same unit, groups 2 and 5 used the same unit, and groups 3 and 6 used the same unit). At the highest does, pooling was required.

Materials and Methods

Animals were handled in accordance with DHHS Publication No. (NIH) 86-23 (Revised, 1985) and the U.S. Department of Agriculture through the Animal Welfare Act (7 U.S.C. 2131), 1985 and Animal Welfare Standards incorporated in 9 C.F.R. Part 3, 1991.

NOD/SCID male mice (Taconic Laboratories, Germantown, N.Y.), all between 7 and 10 weeks old, were sublethally irradiated at 400 cGy using a $^{137}$Cesium source at a rate of about 171 cGy/min. Unanesthetized animals were placed into a Mark I Model 68A Cesium irradiator for the 2.34 minute irradiation interval.

Human placental cells and umbilical cord blood cells were isolated by positive pressure collection (PPC) or negative pressure collection (NPC), and were cryopreserved prior to administration. Cells were thawed in a 37° C. water bath and diluted, then stored on wet ice. The diluent for the cells comprised 5% dextran (Baxter) and 2.5% human serum albumin (Bayer). Cells were counted and assayed for viability. Cells were administered in a single dose through the tail vein of each mouse. The mice were housed under standard conditions and sacrificed at 10 weeks post-irradiation to analyze engraftment.

FACS analysis of marrow and thymus was performed for evidence of human cell engraftment, by assessment for frequency of $CD45^+$ cells, as well as frequency of $CD34^+$, $CD38^+$, $CD19^+$, $CD33^+$, $CD7^+$ and $CD3^+$ cells. Cells were counted and about 500,000 cells were stained per well, at two wells per sample. Mouse Fc block (purified mouse IgG) was added at 1 µg per million cells, to reduce non-specific binding. Antibodies were added at about 1 µg per million cells. One well contained antibodies for CD45, CD34, CD38 and CD19, and the second contained antibodies for CD45, CD33, CD7 and CD3. Isotype controls for each antibody were also used, at about 1 µg per million cells. Following antibody staining, the cells were incubated for 30 minutes at 2-8° C., washed three times with phosphate buffered saline, 1% bovine serum albumin and 0.05% sodium azide, fixed with 1% paraformaldehyde, and stored in the dark at 2-8° C. until analysis. Samples were analyzed by a Becton-Dickinson FACSCalibur with forward- and side-scatter gates set to exclude debris and clumps. Optimal voltage settings and compensations were determined by isotype controls.

Vimentin immunostaining was performed on paraffin sections of mouse sternum using a human-specific vimentin antibody. Scoring was performed semi-quantitatively using the following scale:

| | |
|---|---|
| Score = 0: | No positive cells |
| Score = 0.5: | One or two positive cells, likely positive but cannot be ruled out as background |
| Score = 1: | 2-20 scattered positive cells |
| Score = 2: | Approximately 20-100 scattered or clustered positive cells throughout the tissue |
| Score = 3: | More than 100 positive cells, but making up less than 50% of tissue |
| Score = 4: | More than 50% of marrow cells are positive. |

Results:

Repopulation data are summarized in Table 7, and FACS data is summarized in Table 8. Repopulation was evident to some degree in all animal groups, and the effect appeared to be dose-dependent. The mean percentage of cells positive for each marker was compared at the two different ratios. CD7, CD33, and CD34 showed statistically significant differences between the two ratios, with the 1:1 ratio showing a lower percentage of positive cells than the 3:1 ratio Vimentin staining. Almost all of the sternum sections were composed of 5-6 marrow cavities roughly rectangular in shape, showing some variation in size and shape and surrounded by bony and cartilage tissue. All vimentin positive cells were seen within the bone marrow along with outer erythroid and myeloid precursors in various stages or maturation. No vimentin positive cells were observed in the negative control. Each marrow cavity was scored individually. Generally, the vimentin score correlated well with the dose of cells injected. Both Groups 3 and 6, having the highest number of stem cells, had similar high scores of 3.4. At low and medium dose levels, there was a slight difference between the groups injected with the same number of cells. For example, the mean score for Group 4 (3:1 ratio cord blood cells to placental cells) was slightly higher than Group 1 (1:1 ratio), and the mean score for Group 5 (3:1 ratio) was slightly higher than group 2 (1:1).

Conclusions

Flow cytometry and immunohistochemical evaluations of bone marrow demonstrated substantial repopulation in a cell dose-dependent manner. Differences between the two cell ratios rose to the level of statistical significance for CD7, CD33 and CD34 engraftment. Where significant differences existed, animal receiving 3:1 cord blood to placental cell ratio had a higher degree of repopulation than animals treated with a 1:1 ratio.

TABLE 7

Bone Marrow Repopulation

| Group | Tibia | Femur |
|---|---|---|
| 1 | 9/10 | 6/10 |
| 2 | 6/7 | 5/7 |
| 3 | 9/9 | 9/9 |
| 4 | 4/10 | 5/10 |
| 5 | 7/7 | 7/7 |
| 6 | 9/9 | 9/9 |

Numerator indicates the number of animals per group in which the percentage of CD45+ cells was greater than or equal to 0.5%. Denominator indicates the number of animals per group in which flow cytometry was performed.

TABLE 8

Summary of FACS analysis results.
SUMMARY OF FACS ANALYSIS BY TREATMENT GROUP

| | CD34 | | | CD45 | | | CD19 | | | CD38 | | | CD33 | | | CD3 | | | CD7 | | |
|---|---|---|---|---|---|---|---|---|---|---|---|---|---|---|---|---|---|---|---|---|---|
| Group | T | F | A | T | F | A | T | F | A | T | F | A | T | F | A | T | F | A | T | F | A |
| 1 | 0.0 | 0.0 | 0.0 | 2.2 | 0.8 | 1.5 | 0.1 | 0.1 | 0.1 | 0.0 | 0.0 | 0.0 | 0.1 | 0.0 | 0.1 | 0.0 | 0.0 | 0.0 | 0.0 | 0.0 | 0.0 |
| 2 | 1.1 | 0.6 | 0.9 | 8.0 | 7.3 | 7.7 | 6.6 | 5.8 | 6.2 | 7.8 | 6.6 | 7.2 | 0.6 | 0.6 | 0.6 | 0.0 | 0.0 | 0.0 | 0.0 | 0.0 | 0.0 |
| 3 | 4.9 | 7.4 | 6.2 | 35.1 | 34.8 | 35.0 | 30.6 | 34.4 | 32.5 | 37.5 | 42.3 | 39.9 | 5.2 | 7.1 | 6.2 | 0.0 | 0.0 | 0.0 | 0.0 | 0.2 | 0.1 |
| 4 | 1.2 | 0.9 | 1.1 | 4.8 | 1.5 | 3.2 | 3.9 | 0.3 | 2.1 | 5.5 | 1.2 | 3.4 | 2.4 | 1.7 | 2.1 | 0.0 | 0.0 | 0.0 | 0.3 | 0.4 | 0.4 |
| 5 | 2.6 | 2.8 | 2.7 | 13.1 | 10.1 | 11.6 | 10.4 | 5.2 | 7.8 | 15.6 | 10.6 | 13.1 | 2.0 | 2.7 | 2.4 | 0.0 | 0.0 | 0.0 | 0.4 | 0.4 | 0.4 |
| 6 | 10.2 | 10.7 | 10.5 | 47.9 | 46.6 | 47.3 | 35.9 | 35.6 | 35.8 | 51.0 | 51.8 | 51.4 | 11.0 | 10.4 | 10.7 | 0.0 | 0.0 | 0.0 | 1.2 | 1.1 | 1.2 |

T - Tibia; F = Femur; A = Average of Tibia and Femur. Numbers indicate the percentage of cells staining positive for the indicated human cell surface marker

6.5 Example 5

Hematopoietic Reconstitution in NOD/SCID Mice

Colony formation assays performed with CD34+ placenta-derived stem cells (HPDSC) have demonstrated the presence of functional hematopoietic stem and progenitor cells in placental perfusate. In addition, there is data suggesting that HPDSC contains other novel stem cell populations with more immature characteristics compared to umbilical cord blood (UCB).

An experiment was carried out to determine the engraftment potential of placental perfusate stem cells in a xenogenic transplant model using immunodeficient NOD/SCID mice. The first part of the study evaluated the engraftment potential of placental perfusate cells and umbilical cord blood cells alone or in combination, with control groups receiving purified CD34+ cells. The second part of the study evaluated whether the influence of placental perfusate stem cells on enhanced engraftment is due to increased numbers of repopulating cells or the presence of facilitator cells. In this experiment, three groups of mice received either UCB alone, HPDSC alone, or a combination of HPDSC and UCB. Mice received the same number of CD34+ cells in each group. Separate groups of mice also received a combination of HPDSC and UCB, in which either the HPDSC or UCB cells had been irradiated to prevent repopulating ability, but to preserve any facilitator effect. Because there is known variability in the SCID repopulating ability between individual units of cord blood and placental perfusate, multiple pooled units were used in these experiments.

Methods and Experimental Design

Male NOD/SCID mice 8-10 weeks old were obtained from Jackson Laboratory. Mice were handled aseptically and housed in micro isolator cages in accordance with standard laboratory practice. Mice were offered water and food ad libitum.

Frozen bags of HPDSC and frozen bags of human umbilical cord blood (UCB) were supplied by Celgene Cellular Therapeutics.

On the day of transplantation, HPDSC and UCB units were removed from liquid nitrogen and thawed. After washing, total nucleated cells number (TNC) and viability was determined for each unit. In the second repopulation study part, HPDSC and UCB cells were thawed and prepared in a manner similar to that of the first part, except that HPDSC or UCB cells were irradiated in some of the dose groups. Combinations of HPDSC and UCB cell preparations were prepared by mixing appropriate amounts of HPDSC and UCB cells.

Cell counts were performed with automated cell analyzers (Cell-Dyne 1700 or Cell Dyne 320, Abbot; Wiesbaden, Germany). The viability of cell preparation was determined by Trypan Blue exclusion method.

SCID repopulating cell assays were carried out in NOD/SCID mice at 8-10 weeks of age. The mice were irradiated at 325-350 cGy with irradiation from linear accelerator at an exposure rate of 20 cGy/min prior to transplantation. Mice were then transplanted intravenously via lateral tail vain with 200 μL of UCB or human placental perfusate cells or combination of UCB and human placental perfusate cells. Engraftment analysis was performed at 4 weeks and 12 weeks after transplant.

Analysis of engraftment of human cells was performed by flow cytometric analysis. In brief, samples were stained with an antibody, fixed with 1% paraformaldehyde, and analyzed by using Becton Dickson FACSCalibur for human CD45 and panel of other lineage cell surface markers, including CD34, CD7, CD33, CD10, CD7 and CD3. Optimal voltage settings and compensations were determined by isotype control. Four weeks engraftment analysis was performed with bone marrow aspirate obtained from anesthetized mice and at 12 weeks animals were sacrificed and bone marrow cells were flushed from femurs and tibias. Mice were considered engrafted if the percentage of human CD45 was >0.5%.

Experimental Design. On the day of transplantation animals were irradiated and randomized into different treatment groups, as shown in Tables 9 and 10:

TABLE 9

Repopulation study Part (A)

| Group | Mice/Group | Dose volume | CD34#/mouse ACTUAL |
|---|---|---|---|
| UCB | 13 | 200 | $1 \times 10^5$ |
| HPDSC | 13 | 200 | $5.1 \times 10^4$ |
| UCB + HPDSC | 13 | 200 | $1 \times 10^5 + 5.1 \times 10^4$ |
| Control Hi | 6 | 200 | $2.5 \times 10^5$ |
| Control Lo | 5 | 200 | $1.25 \times 10^5$ |

TABLE 10

Repopulation study Part (B)

| Group | Mice/Group | CD34#/mouse - Estimated | CD34#/mouse ACTUAL | TNC/mouse - ACTUAL($10^6$) |
|---|---|---|---|---|
| UCB | 15 | $3.0 \times 10^5$ CD34/mouse | $2.7 \times 10^5$ CD34/mouse | 28.4 |
| PP1 | 15 | $3.0 \times 10^5$ CD34/mouse | $2.6 \times 10^5$ CD34/mouse | 17.72 |
| UCB + PP1 (same total CD34 cell dose) | 15 | $3.0 \times 10^5$ CD34/mouse (1.5 + 1.5) | $2.7 \times 10^5$ CD34/mouse (1.4 + 1.3) | 14.8 + 8.86 |
| UCB$^{irr}$ + PP1 (same total CD34 cell dose) | 15 | $3.0 \times 10^5$ CD34/mouse (1.5 + 1.5) | $2.7 \times 10^5$ CD34/mouse (1.4 + 1.3) | 14.8 + 8.86 |
| UCB + PP1$^{irr}$ (same total CD34 cell dose) | 15 | $3.0 \times 10^5$ CD34/mouse (1.5 + 1.5) | $2.7 \times 10^5$ CD34/mouse (1.4 + 1.3) | 14.8 + 8.86 |
| Control | 5 | $3.0 \times 10^5$ CD34/mouse | | |

Irr = irradiated cells

Results

Post thaw cell viability. Post thaw cell viability of UCB and HPDSC was more than 70% for the units used in repopulation study.

Human Cell Engraftment in NOD/SCID Mice. Human cell engraftment (>0.5% CD45) was observed in all groups 4 weeks post infusion, including HPDSC alone, with 2 out of 6 mice positive for engraftment in the UCB group (mean CD45% of 0.62%), 2 out of 8 mice in the HPDSC group (mean CD45% of 0.52%), and 8 out of 9 mice in the group that received both UCB and HPDSC (mean CD45% of 2.84%). There was a significant increase in human engraftment observed when comparing either the HPDSC group alone to the UCB+HPDSC group (p=0.006) and the UCB group to the UCB+HPDSC group (p=0.02). At 12 weeks post transplant, sustained engraftment in the HPDSC group alone was not observed with only 1 out of 8 animals engrafted at >0.5% CD45. In contrast, although there was no statistical difference observed in the overall level of human engraftment between mice that received UCB alone versus the UCB+HPDSC group (mean CD45% of 15.1% and 13.1%, respectively; p=0.82), only 3 out of 6 mice were engrafted in the UCB group as compared to 9 out of 9 mice in the UCB+HPDSC group. Mice engrafted with human cells also showed engraftment of lymphomyeloyid and other lineage cell types (Tables 11 and 12). These data indicate that co-infusion of HPDSC and UCB results in significant enhancement of both short- and longer-term human engraftment as compared to HPDSC or UCB alone.

TABLE 11

Percent engraftment of lymphomyeloid and other lineage markers cells in bone marrow of NOD/SCID mice after 4 weeks of intravenous transplantation of human placenta derived stem cells and umbilical cord blood alone or in combination

| Percent human cell Engraftment | UCB | HPDSC | UCB + HPDSC | Control (Hi) | Control(Low) |
| --- | --- | --- | --- | --- | --- |
| CD45 | 0.62 ± 0.92 | 0.52 ± 0.76 | 2.84 ± 1.89 | 1.33 ± 0.90 | 0.09 ± 0.14 |
| CD33 | 0.51 ± 0.78 | 0.43 ± 0.67 | 2.41 ± 1.52 | 0.91 ± 0.68 | 0.02 ± .05 |
| CD19 | 0.17 ± 0.24 | 0.15 ± 0.31 | 0.76 ± 1.0 | 0.44 ± 0.43 | 0.04 ± 0.08 |

TABLE 12

Percent engraftment of lymphomyeloid and other lineage markers cells in bone marrow of NOD/SCID mice after 12 weeks of intravenous transplantation of human placenta derived stem cells and umbilical cord blood alone or in combination.

| Percent human cell Engraftment | UCB | HPDSC | UCB + HPDSC | Control (Hi) | Control(Low) |
| --- | --- | --- | --- | --- | --- |
| CD45 | 15.0 ± 22.09 | 0.65 ± 1.51 | 13.09 ± 11.56 | 11.3 ± 8.11 | 0.04 ± 0.04 |
| CD34 | 3.67 ± 5.55 | 0.21 ± 0.54 | 3.21 ± 3.41 | 2.76 ± 2.08 | 0.01 ± 0.01 |
| CD33 | 6.33 ± 9.18 | 0.40 ± 1.04 | 5.61 ± 5.19 | 4.18 ± 3.56 | 0.01 ± 0.01 |
| CD19 | 9.96 ± 16.66 | 0.30 ± 0.70 | 8.52 ± 9.97 | 8.02 ± 5.67 | 0.02 ± 0.03 |
| CD10 | 12.02 ± 17.51 | 0.26 ± 0.59 | 8.74 ± 10.04 | 8.28 ± 5.60 | 0.02 ± 0.02 |
| CD7 | 1.05 ± 1.65 | 0.21 ± 0.32 | 1.01 ± 1.36 | 1.05 ± 0.78 | 0.01 ± 0.01 |
| CD3 | 0.14 ± 0.15 | 0.03 ± 0.03 | 0.10 ± 0.07 | 0.10 ± 0.06 | 0.02 ± 0.01 |

Facilitator effect. Enhanced human engraftment was seen in the UCB+HPDSC group as compared to the UCB or HPDSC group alone (Tables 13 and 14). Furthermore, although the group of mice that received irradiated HPDSC with UCB received half the number of functional CD34 cells per mice than the group of mice that received CB alone or CB+PP1, there was equivalent human engraftment in this group, suggesting a facilitator function of the HPDSC.

Delayed engraftment following cord blood transplantation remains a significant clinical problem, even in the case of double unit myeloablative cord blood transplantation, where the median time to neutrophil engraftment is about 23 days. These results also suggest clinical investigation of co-infusion of HPDSC with either single or double cord blood units for transplantation as a potential method to facilitate more rapid engraftment.

TABLE 13

Percent engraftment of lymphomyeloid and other lineage markers cells in bone marrow of NOD/SCID mice after 4 weeks of intravenous transplantation of human placenta derived stem cells and umbilical cord blood alone or in combination

| Percent human cell Engraftment | UCB | HPDSC | UCB + HPDSC | UCBirr + HPDSC | UCB + HPDSC irr | Control |
|---|---|---|---|---|---|---|
| CD45 | 11.0 ± 11.52 | 0.69 ± 0.70 | 6.84 ± 6.61 | 0.31 ± 0.48 | 16.48 ± 19.62 | 15.83 ± 11.25 |
| CD34 | 5.45 ± 5.50 | 0.34 ± 0.34 | 3.72 ± 3.82 | 0.08 ± 0.13 | 9.43 ± 13.99 | 6.90 ± 5.32 |
| CD33 | 5.94 ± 5.59 | 0.52 ± 0.59 | 5.17 ± 5.26 | 0.26 ± 0.44 | 11.79 ± 16.62 | 6.41 ± 5.10 |
| CD19 | 5.65 ± 8.07 | 0.09 ± 0.10 | 2.06 ± 1.92 | 0.06 ± 0.10 | 5.75 ± 5.86 | 8.23 ± 5.52 |

TABLE 14

Percent engraftment of lymphomyeloid and other lineage markers cells in bone marrow of NOD/SCID mice after 12 weeks of intravenous transplantation of human placenta derived stem cells and umbilical cord blood alone or in combination

| Percent human cell Engraftment | UCB | HPDSC | UCB + HPDSC | UCBirr + HPDSC | UCB + HPDSC irr | Control |
|---|---|---|---|---|---|---|
| CD45 | 41.86 ± 28.70 | 15.10 ± 23.75 | 48.29 ± 28.18 | 0.68 ± 0.66 | 51.62 ± 29.91 | 33.37 ± 19.18 |
| CD34 | 8.78 ± 6.20 | 2.48 ± 3.35 | 9.32 ± 7.70 | 0.08 ± 0.09 | 8.20 ± 6.38 | 10.29 ± 5.77 |
| CD33 | 7.98 ± 5.12 | 2.66 ± 4.01 | 8.32 ± 6.29 | 0.17 ± 0.20 | 6.16 ± 4.35 | 4.23 ± 2.72 |
| CD19 | 36.99 ± 25.69 | 13.48 ± 21.35 | 41.25 ± 0.49 | 0.49 ± 0.69 | 47.04 ± 27.07 | 28.31 ± 16.69 |

6.6 Example 6

Treatment of Amyotrophic Lateral Sclerosis Using a Combined Stem Cell Population Amyotrophic Lateral Sclerosis (ALS), also called Lou Gehrig's disease, is a fatal neurodegenerative disease affecting motor neurons of the cortex, brain stem and spinal cord. ALS affects as many as 20,000 Americans with 5,000 new cases occurring in the US each year. The majority of ALS cases are sporadic (S-ALS) while ~5-10% are hereditary (familial—F-ALS). ALS occurs when specific nerve cells in the brain and spinal cord that control voluntary movement gradually degenerate. The cardinal feature of ALS is the loss of spinal motor neurons which causes the muscles under their control to weaken and waste away leading to paralysis. ALS manifests itself in different ways, depending on which muscles weaken first. ALS strikes in mid-life with men being one-and-a-half times more likely to have the disease as women. ALS is usually fatal within five years after diagnosis.

ALS has both familial and sporadic forms, and the familial forms have now been linked to several distinct genetic loci. Only about 5-10% of ALS cases are familial. Of these, 15-20% are due to mutations in the gene encoding Cu/Zn superoxide dismutase 1 (SOD1). These appear to be "gain-of-function" mutations that confer toxic properties on the enzyme. The discovery of SOD mutations as a cause for ALS has paved the way for some progress in the understanding of the disease; animal models for the disease are now available and hypotheses are being developed and tested concerning the molecular events leading to cell death.

Presented below is an example method of treating an individual having ALS with A combined stem cell population. The method involves intravenous infusion through a peripheral, temporary angiocatheter.

An individual having ALS is first assessed by the performance of standard laboratory analyses. Such analyses may include a metabolic profile; CBC with differential; lipid profile; fibrinogen level; ABO rH typing of the blood; liver function tests; and determination of BUN/creatine levels. Individuals are instructed the day prior to the transplant to take the following medications: diphenhydramine (BENADRYL™), 25 mg t.i.d, and prednisone, 10 mg.

A combined stem cell population is produced from a unit of placental perfusate and a matched unit of cord blood (that is, the perfusate is taken from the same placenta from which the cord blood is obtained). Total nucleated cell populations from the perfusate and the cord blood are isolated, and samples of each are tested in vitro in a plurality of ratios to determine the ratio that produces the highest number of colony-forming units. The two populations are combined in approximately that ratio to create a combined stem cell population. This stem cell population is maintained for approximately two days prior to transplantation at a temperature of about 5° C.

The individual is transplanted at an outpatient clinical center that has all facilities necessary for intravenous infusion, physiological monitoring and physical observation. Approximately one hour prior to transplantation, the individual receives diphenhydramine (BENADRYL™), 25 mg×1 P.O., and prednisone, 10 mg×1 P.O. This is precautionary, and is meant to reduce the likelihood of an acute allergic reaction. At the time of transfusion, an 18 G indwelling peripheral venous line is placed into one of the individual's extremities, and is maintained open by infusion of D5 ½ normal saline+20 mEq KCl at a TKO rate. The individual is examined prior to transplantation, specifically to note heart rate, respiratory rate, temperature. Other monitoring may be performed, such as an electrocardiogram and blood pressure measurement.

The combined stem cell population is then infused at a rate of approximately $1\text{-}2\times10^9$ total nucleated cells per hour in a total delivered fluid volume of 60 ml. Based upon data from pre-clinical studies in mice, a total of $2.0\text{-}2.5\times10^8$ cells per kilogram of body weight should be administered. For example, a 70 kilogram individual would receive approximately $14\text{-}18\times10^9$ total nucleated cells. The individual should be monitored for signs of allergic response or hypersensitivity, which are signals for immediate cessation of infusion.

Post-infusion, the individual should be monitored in a recumbent position for at least 60 minutes, whereupon he or she may resume normal activities.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

What is claimed is:

1. A combined cell population comprising a number of cells in vitro, said number of cells comprising isolated nucleated placental cells that comprise placental stem cells, and comprising stem cells from a second source, wherein said combined cell population, when cultured for a time and under conditions that allow the formation of colony-forming units, produces more colony-forming units than a number of said isolated nucleated placental cells equivalent to the number of cells in the combined cell population or a number of said stem cells from a second source equivalent to the number of cells in the combined cell population, alone, and wherein said isolated nucleated placental cells are obtained by perfusion of a post-partum human placenta by passing a perfusion solution into one or both of the umbilical artery and umbilical vein of said placenta and isolation of said isolated nucleated placental cells from the perfusate, wherein said placenta has been drained of cord blood and flushed to remove residual blood; and wherein said nucleated placental cells are not obtained from cord blood.

2. The combined cell population of claim 1, wherein said isolated nucleated placental cells and stem cells from a second source show improved engraftment when introduced into a recipient compared to a number of isolated nucleated placental cells equivalent to the number of cells in the combined cell population, or a number of stem cells from a second source equivalent to the number of cells in the combined cell population, alone.

3. The combined cell population of claim 1 comprising said isolated nucleated placental cells and said stem cells from a second source in a ratio, out of a plurality of ratios, that, when cultured under conditions allowing the formation of colony forming units, produces the most colony forming units.

4. The combined cell population of claim 1, wherein said stem cells from a second source are cord blood stem cells, bone marrow stem cells, hematopoietic stem cells, or mesenchymal stem cells.

5. The combined cell population of claim 4, wherein said hematopoietic stem cells are cord blood hematopoietic stem cells.

6. The combined cell population of claim 4, wherein said hematopoietic stem cells are $CD34^+$ cells.

7. The combined cell population of claim 1, wherein said placental stem cells comprise $CD34^+$ cells.

8. The combined cell population of claim 1, wherein said placental stem cells comprise $CD34^+$ cells.

9. The combined cell population of claim 1, wherein said placental stem cells comprise cells that are $OCT4^+$ or $ABC-p^+$.

10. The combined cell population of claim 1, wherein said placental stem cells comprise cells that are $CD34^+$ and cells that are $OCT4^+$ or $ABC-p^+$.

11. The combined cell population of claim 1, wherein said placental stem cells are contained within placental perfusate substantially lacking red blood cells and cellular debris.

12. The combined cell population of claim 1, wherein said population comprises placental stem cells isolated from enzyme-digested placental tissue.

13. The combined cell population of claim 1, wherein said isolated nucleated placental cells and said stem cells from a second source are obtained from the same individual.

14. The combined cell population of claim 1, wherein said isolated nucleated placental cells and said stem cells from a second source are obtained from different individuals.

15. The combined cell population of claim 1, wherein said isolated nucleated placental cells are obtained from a plurality of placentas.

16. The combined cell population of claim 1, wherein said stem cells from a second source are obtained from a plurality of individuals.

17. A method of transplantation, comprising transplanting to a recipient a combined cell population comprising a number of isolated nucleated placental cells that comprise placental stem cells, and comprising stem cells from a second source, wherein said combined stem cell population, when transplanted, results in enhanced engraftment compared to transplantation of a number of isolated nucleated placental cells equivalent to the number of cells in the combined stem cell population, or stem cells from a second source equivalent to the number of cells in the combined stem cell population, alone, and
wherein said isolated nucleated placental cells are obtained by perfusion of a post-partum human placenta by passing a perfusion solution into one or both of the umbilical artery and umbilical vein of said placenta and isolation of said isolated nucleated placental cells from the perfusate; wherein said placenta has been drained of cord blood and flushed to remove residual blood; and wherein said nucleated placental cells are not obtained from cord blood.

18. The method of claim 17, wherein the combined cell population comprises said isolated placental cells and stem cells from a second source in a ratio that, when said combined cell population is cultured for a time and under conditions sufficient to allow formation of colony-forming units, produces a greater number of colony-forming units than a number of said nucleated placental cells equivalent to the number of cells in the combined cell population, or a number of said stem cells from a second source equivalent to the number of cells in the combined cell population, alone.

19. The method of claim 18, wherein said ratio is selected by selecting, within a plurality of ratios of said isolated nucleated placental cells and stem cells from a second source cultured for a time and under conditions sufficient to allow the formation of colony-forming units, a ratio that produces the greatest number of colony-forming units.

20. The method of claim 17, wherein said stem cells from a second source are cord blood stem cells, bone marrow stem cells, hematopoietic stem cells, or mesenchymal stem cells.

21. The method of claim 17, wherein said stem cells from a second source are hematopoietic stem cells.

22. The method of claim 21, wherein said hematopoietic stem cells are cord blood hematopoietic stem cells.

23. The method of claim 21, wherein said hematopoietic stem cells are $CD34^+$ cells.

24. The method of claim 18, wherein the placental perfusate cells comprise $CD34^+$ cells.

25. The method of claim 18, wherein the placental perfusate cells comprise cells that are $CD34^+$ and cells that are $OCT4^+$ or $ABC-p^+$.

26. The method of claim 18, wherein said isolated nucleated placental cells are contained within placental perfusate substantially lacking red blood cells and cellular debris.

27. The method of claim 18, wherein said composition comprises placental stem cells isolated from enzyme-digested placental tissue.

28. The method of claim 18, wherein said transplantation results in a statistically significantly enhanced engraftment of $CD34^+$ or $CD45^+$ cells in said recipient as compared to transplantation of a number of stem cells from a second source equivalent to the number of cells in the combined cell population alone.

29. The method of claim 18, wherein said transplantation results in a statistically significantly higher engraftment of $CD34^+$ or $CD45^+$ cells in said recipient as compared to transplantation of a number of cord blood stem cells equivalent to the number of cells in the combined cell population alone.

30. The method of claim 18, wherein the ratio of said isolated nucleated placental cells and said hematopoietic stem cells is from about 1:100 to about 100:1 at the time of transplantation, as determined by total numbers of nucleated cells.

31. The method of claim 30, wherein the ratio of said isolated nucleated placental cells and said hematopoietic stem cells is from about 1:10 to about 10:1 at the time of transplantation, as determined by the total numbers of nucleated cells.

32. A composition comprising a combined cell population in a container, wherein said combined stem cell population comprises a number of isolated nucleated placental cells comprising placental stem cells, and stem cells from a second source, wherein said composition produces detectably higher engraftment in an individual receiving the composition, compared to an individual who receives said number of isolated nucleated placental cells or said number of stem cells from a second source, alone, and
wherein said isolated nucleated placental cells are obtained by perfusion of a post-partum human placenta by passing a perfusion solution into one or both of the umbilical artery and umbilical vein of said placenta and isolation of said isolated nucleated placental cells from the perfusate; wherein said placenta has been drained of cord blood and flushed to remove residual blood; and wherein said nucleated placental cells are not obtained from cord blood.

33. The composition of claim 32, wherein the container is a bag, flask, or jar.

34. The composition of claim 32, wherein said isolated nucleated placental cells and said stem cells from a second source are contained together in a bag.

35. The composition of claim 32, wherein said isolated nucleated placental cells and said stem cells from a second source are contained separately within a bag.

36. The composition of claim 32, wherein said composition comprises one or more compounds that facilitate cryopreservation of the combined cell population.

37. The composition of claim 32, wherein said combined cell population is contained within a physiologically-acceptable aqueous solution.

38. The composition of claim 37, wherein said physiologically-acceptable aqueous solution is a 0.9% NaCl solution.

39. The composition of claim 33, wherein said bag is a sterile plastic bag.

40. The composition of claim 39, wherein said bag allows or facilitates intravenous administration of said combined cell population.

41. The composition of claim 32, wherein said combined cell population comprises isolated nucleated placental cells that are HLA-matched to said stem cells from a second source.

42. The composition of claim 32, wherein said combined cell population comprises isolated nucleated placental cells that are at least partially HLA-mismatched to said stem cells from a second source.

43. The composition of claim 32, wherein said isolated nucleated placental perfusate cells are derived from a plurality of donors.

44. The composition of claim 32, wherein said stem cells from a second source are derived from a plurality of donors.

45. The composition of claim 32, where said placental stem cells, said stem cells from a second source, or both have been passaged at least two times.

46. The composition of claim 32, where said placental stem cells, said stem cells from a second source, or both have been passaged at least five times.

47. The composition of claim 32, where said placental stem cells, said stem cells from a second source, or both have been passaged at least 10 times.

48. The composition of claim 32, where said placental stem cells, said stem cells from a second source, or both have been passaged at least 15 times.

49. The composition of claim 32, where said placental stem cells, said stem cells from a second source, or both have been passaged at least 20 times.

* * * * *

UNITED STATES PATENT AND TRADEMARK OFFICE
CERTIFICATE OF CORRECTION

PATENT NO.        : 7,700,090 B2                                                                Page 1 of 1
APPLICATION NO.   : 11/648802
DATED             : April 20, 2010
INVENTOR(S)       : Heidaran et al.

It is certified that error appears in the above-identified patent and that said Letters Patent is hereby corrected as shown below:

In claim 8, column 51, line 9, replace "$CD34^{+}$" with --$CD34^{-}$--

In claim 27, column 52, line 20, replace "composition" with --combined cell population--

Signed and Sealed this

Twenty-seventh Day of July, 2010

David J. Kappos
*Director of the United States Patent and Trademark Office*